United States Patent
Grønborg et al.

(10) Patent No.: US 9,845,344 B2
(45) Date of Patent: Dec. 19, 2017

(54) THERAPEUTIC USE OF A GROWTH FACTOR, NSG33

(75) Inventors: Mette Grønborg, Copenhagen (DK); Philip Kusk, Lynge (DK); Nikolaj Blom, Copenhagen (DK); Thomas Nordahl Petersen, Copenhagen (DK); Teit E. Johansen, Hørsholm (DK); Søren Brunak, Hellerup (DK); Lars U. Wahlberg, Asnæs (DK)

(73) Assignee: HOBA THERAPEUTICS APS, Copenhagen (DK)

( * ) Notice: Subject to any disclaimer, the term of this patent is extended or adjusted under 35 U.S.C. 154(b) by 1467 days.

(21) Appl. No.: 10/594,192

(22) PCT Filed: Mar. 30, 2005

(86) PCT No.: PCT/EP2005/051431
§ 371 (c)(1),
(2), (4) Date: Sep. 25, 2006

(87) PCT Pub. No.: WO2005/095450
PCT Pub. Date: Oct. 13, 2005

(65) Prior Publication Data
US 2007/0275026 A1 Nov. 29, 2007

Related U.S. Application Data

(60) Provisional application No. 60/575,086, filed on May 28, 2004.

(30) Foreign Application Priority Data

Mar. 30, 2004 (DK) ................... 2004 00510
May 28, 2004 (DK) ................... 2004 00843

(51) Int. Cl.
| | |
|---|---|
| *A61K 38/18* | (2006.01) |
| *C07K 14/475* | (2006.01) |
| *A01K 67/027* | (2006.01) |
| *A61K 38/17* | (2006.01) |
| *A61K 38/00* | (2006.01) |

(52) U.S. Cl.
CPC .......... *C07K 14/475* (2013.01); *A01K 67/027* (2013.01); *A61K 38/185* (2013.01); *A01K 2207/05* (2013.01); *A01K 2207/20* (2013.01); *A01K 2227/105* (2013.01); *A01K 2267/0356* (2013.01); *A61K 38/00* (2013.01); *A61K 38/17* (2013.01); *C12N 2799/027* (2013.01)

(58) Field of Classification Search
None
See application file for complete search history.

(56) References Cited

FOREIGN PATENT DOCUMENTS

| | | |
|---|---|---|
| WO | WO 93/22437 | 11/1993 |
| WO | WO 95/05452 | 2/1995 |
| WO | WO 97/44065 | 11/1997 |
| WO | WO 01/39786 A2 | 6/2001 |
| WO | WO 01/54474 A2 | 8/2001 |
| WO | WO 01/55301 A2 | 8/2001 |
| WO | WO 01/55440 A1 | 8/2001 |
| WO | WO 01/57190 A2 | 8/2001 |
| WO | WO 01/83510 A1 | 11/2001 |
| WO | WO 03/066877 A2 | 8/2003 |
| WO | WO 2004/035732 A2 | 4/2004 |
| WO | WO 2004/079014 A2 | 9/2004 |

OTHER PUBLICATIONS

Rudinger, In "Peptide Hormones" (Ed. J.A. Parsons), University Park Press, Baltimore, pp. 1-7 (1976).*
Jackowski, British Journal of Neurosurgery 9: 303-317 (1995).*
Grønborg et al., "Identification of secreted neurotrophic factors using bioinformatics combined with expression analysis", program No. 825.2, abstract viewer/itinerary planner, Washington, DC: Society for Neuroscience (2005).
Mu et al., "Gene expression in the developing mouse retina by EST sequencing and microarray analysis", *Nucl. Acids Res.*, 29(24):4983-4993 (2001).
Navarro-Galvel et al., "HNSG33 effects on survival and differentiation of human neural stem-cell derived neuronal and glial progeny", program No. 248.14, abstract viewer/intinerary planner, Washington, DC: Society for Neuroscience (2005).
Nishino et al., "Meteorin: a secreted protein that regulates glial cell differenctiation and promotes axonal extension", *EMBO J.*, 23(9):1998-2008 (2004).
Colton "Engineering challenges in cell-encapsulation technology" Trends Biotechnol. May 1996;14(5):158-162.
Communication from European Patent Office for EP 09 156 744.6-2403 dated Aug. 12, 2010.
International Search Report from PCT/EP2005/051431, dated Aug. 23, 2005.
GenBank, Accession No. AAM78739, Nov. 6, 2001.
GenBank, Accession No. AAM79723, Nov. 6, 2001.
GenBank, Accession No. ABB10367, Jan. 10, 2002.
GenBank, Accession No. ABB10537, Jan. 10, 2002.
GenBank, Accession No. ABA06589, Jan. 10, 2002.
GenBank, Accession No. ABA06759, Jan. 10, 2002.
GenBank, Accession No. ABB57447, Mar. 15, 2002.
GenBank, Accession No. ADP29324, Aug. 12, 2004.
GenBank, Accession No. BG806341, Dec. 21, 2001.

(Continued)

*Primary Examiner* — Robert C Hayes
(74) *Attorney, Agent, or Firm* — Dinsmore & Shohl LLP

(57) ABSTRACT

The present invention relates to the field of therapeutic use of proteins, genes and cells. More specifically the invention relates to therapy based on the biological function of a secreted therapeutic protein, NsG33, in particular for the treatment of disorders of the nervous system. NsG33 is a nerve survival and growth factor with antiapoptotic effects on a cell line with neuronal potential and with neuroprotective and/or neurogenesis effects on a neural precursor cell line and on primary striatal cultures. The invention also relates to novel bioactive NsG33 polypeptide fragments and the corresponding encoding DNA sequences.

7 Claims, 13 Drawing Sheets

(56) References Cited

OTHER PUBLICATIONS

GenBank, Accession No. CAB56188, Sep. 17, 1999.
GenBank, Accession No. AAH00662, Nov. 29, 2000.
GenBank, Accession No. NP_076947, Feb. 27, 2001.
GenBank, Accession No. AAK61247, Jun. 8, 2001.
GenBank, Accession No. AAH37181, Sep. 23, 2002.
GenBank, Accession No. AAH88383, Dec. 22, 2004.
Alexi et al, "Neuroprotective strategies for basal ganglia degeneration: Parkinson's and Huntington's diseases," *Progress in Neurobiology* 60(5): 409-470 (2000).
Gallagher et al., *Handbook of Psychology*, New York: John Wiley & Sons, Inc. p. 391 (2003).
Nielsen et al., "A Neural Network Method for Identification of Prokaryotic and Eukaryotic Signal Peptides and Prediction of Their Cleavage Sites," *International Journal of Neural Systems* 8(5 & 6): 581-599 (1997).
von Heijne, "A New Method for Predicting Signal Sequence Cleavage Sites," *Nucleic Acids Research* 14(11): 4683-4690 (1986).
Communication from European Patent Office for European Patent Application No. 10182987, dated Mar. 2, 2011, enclosing Extended European Search Report dated Feb. 15, 2011.
Fransen et al., "Molecular Cloning of a Novel Macrophaged Derived Cytokine (SMAF-1) and its Immunomodulating Capacities ," published at the Seventh Annual Conference of the International Cytokine Society, Hilton Head, SC USA, Dec. 5-9, 1999.

* cited by examiner

```
>IPI00031531.1        length = 293
# Measure  Position  Value  Cutoff  signal peptide?
  max. C     24      0.785   0.33    YES
  max. Y     24      0.746   0.32    YES
  max. S     11      0.989   0.82    YES
  mean S    1-23     0.846   0.47    YES
# Most likely cleavage site between pos. 23 and 24: ARA-GY
```

```
>IPI00031531.1
Prediction: Signal peptide
Signal peptide probability: 1.000
Signal anchor probability: 0.000
Max cleavage site probability: 0.832 between pos. 23 and 24
```

FIG. 2 human NsG33 (SEQ ID No 3)

| # Gene Ontology category | Odds |
|---|---|
| Signal_transducer | 0.538 |
| Receptor | 0.433 |
| Hormone | 1.173 |
| Structural_protein | 0.168 |
| Transporter | 0.230 |
| Ion_channel | 0.372 |
| Voltage-gated_ion_channel | 0.130 |
| Cation_channel | 0.215 |
| Transcription | 0.294 |
| Transcription_regulation | 0.152 |
| Stress_response | 0.340 |
| Immune_response | 0.186 |
| Growth_factor | 2.083 |
| Metal_ion_transport | 0.020 | human N-terminal peptide (SEQ ID No 19)

| # Gene Ontology category | Odds |
|---|---|
| Signal_transducer | 0.464 |
| Receptor | 0.296 |
| Hormone | 0.206 |
| Structural_protein | 0.987 |
| Transporter | 0.311 |
| Ion_channel | 0.147 |
| Voltage-gated_ion_channel | 0.157 |
| Cation_channel | 0.215 |
| Transcription | 0.311 |
| Transcription_regulation | 0.829 |
| Stress_response | 0.162 |
| Immune_response | 1.460 |
| Growth_factor | 8.142 |
| Metal_ion_transport | 0.061 | human C-terminal peptide (SEQ ID No 5)

| # Gene Ontology category | Odds |
|---|---|
| Signal_transducer | 0.242 |
| Receptor | 0.038 |
| Hormone | 0.303 |
| Structural_protein | 0.096 |
| Transporter | 0.231 |
| Ion_channel | 0.185 |
| Voltage-gated_ion_channel | 0.191 |
| Cation_channel | 0.215 |
| Transcription | 0.312 |
| Transcription_regulation | 0.295 |
| Stress_response | 0.145 |
| Immune_response | 0.157 |
| Growth_factor | 7.963 |
| Metal_ion_transport | 0.020 |

Fig 3a. CLUSTAL W (1.82) multiple sequence alignment

```
Mouse NsG33      HASAHASALLCALCCGLLAASAHAGYSEDRCSWRGSGLTQEPGSVGQLTLDCTEGAIEWL
Rat   NsG33      ---MLVAALLCALCCGLLAASARAGYSEDRCSWRGSGLTQEPGSVGQLTLDCTEGAIEWL
Human NsG33      -MGFPAAALLCALCCGLLAPAARAGYSEERCSWRGSGLTQEPGSVGQLALACAEGAVEWL
                  .:************.:*:*****:********************:* *:***:***

Mouse NsG33      YPAGALRLTLGGPDPGTRPSIVCLRPERPFAGAQVFAERMTGNLELLLAEGPDLAGGRCM
Rat   NsG33      YPAGALRLTLGGSDPGTRPSIVCLRPTRPFAGAQVFAERMAGNLELLLAEGQGLAGGRCM
Human NsG33      YPAGALRLTLGGPDPRARPGIACLRPVRPFAGAQVFAERAGGALELLLAEGPGPAGGRCV
                 ************.** :**.*.**** ************* ********* . *****:

Mouse NsG33      RWGPRERRALFLQATPHRDISRRVAAFRFELHEDQRAEMSPQAQGLGVDGACRPCSDAEL
Rat   NsG33      RWGPRERRALFLQATPHRDISRRVAAFQFELHEDQRAEMSPQAQGFGVDGACRPCSDAEL
Human NsG33      RWGPRERRALFLQATPHQDISRRVAAFRFELREDGRPELPPQAHGLGVDGACRPCSDAEL
                 *****************:********:***:** *.*:.***:*:**************

Mouse NsG33      LLAACTSDFVIHGTIHGVAHDTELQESVITVVVARVIRQTLPLFKEGSSEGQGRASIRTL
Rat   NsG33      LLTACTSDFVIHGTIHGVVHDMELQESVITVVATRVIRQTLPLFQEGSSEGRGQASVRTL
Human NsG33      LLAACTSDFVIHGIIHGVTHDVELQESVITVVAARVLRQTPPLFQAGRSGDQGLTSIRTP
                 **:********** ****.** **********.:**:*** ***: * * .:* :*:**

Mouse NsG33      LRCGVRPGPGSFLFMGWSRFGEAWLGCAPRFQEFSRVYSAALTTHLNPCEMALD
Rat   NsG33      LRCGVRPGPGSFLFMGWSRFGEAWLGCAPRFQEFSRVYSAALAAHLNPCEVALD
Human NsG33      LRCGVHPGPGTFLFMGWSRFGEARLGCAPRFQEFRRAYEAARAAHLHPCEVALH
                 *****:****.***********  **********  *.*.**  ::**:***:**.
```

Fig 3b. CLUSTAL W (1.82) multiple sequence alignment

```
Mouse      --MLVATLLCALCCGLLAASAHAGYSEDRCSWRGSGLTQEPGSVGQLTLDCTEGAIEWLY  58
Rat        --MLVAALLCALCCGLLAASARAGYSEDRCSWRGSGLTQEPGSVGQLTLDCTEGAIEWLY  58
Human      MGFPAAALLCALCCGLLAPAARAGYSEERCSWRGSGLTQEPGSVGQLALACAEGAVEWLY  60
             .*:************.:*:*****:********************:* *:***:****

Mouse      PAGALRLTLGGPDPGTRPSIVCLRPERPFAGAQVFAERMTGNLELLLAEGPDLAGGRCMR 118
Rat        PAGALRLTLGGSDPGTRPSIVCLRPTRPFAGAQVFAERMAGNLELLLAEGQGLAGGRCMR 118
Human      PAGALRLTLGGPDPRARPGIACLRPVRPFAGAQVFAERAGGALELLLAEGPGPAGGRCVR 120
           ***********.** :**.*.**** ************* ********* . *****:*

Mouse      WGPRERRALFLQATPHRDISRRVAAFRFELHEDQRAEMSPQAQGLGVDGACRPCSDAELL 178
Rat        WGPRERRALFLQATPHRDISRRVAAFQFELHEDQRAEMSPQAQGFGVDGACRPCSDAELL 178
Human      WGPRERRALFLQATPHQDISRRVAAFRFELREDGRPELPPQAHGLGVDGACRPCSDAELL 180
           ****************:********:***:** *.*:.***:*:****************

Mouse      LAACTSDFVIHGTIHGVAHDTELQESVITVVVARVIRQTLPLFKEGSSEGQGRASIRTLL 238
Rat        LTACTSDFVIHGTIHGVVHDMELQESVITVVATRVIRQTLPLFQEGSSEGRGQASVRTLL 238
Human      LAACTSDFVIHGIIHGVTHDVELQESVITVVAARVLRQTPPLFQAGRSGDQGLTSIRTPL 240
           *:********** ****.** **********.:**:*** ***: * * .:* :*:** *

Mouse      RCGVRPGPGSFLFMGWSRFGEAWLGCAPRFQEFSRVYSAALTTHLNPCEMALD 291
Rat        RCGVRPGPGSFLFMGWSRFGEAWLGCAPRFQEFSRVYSAALAAHLNPCEVALD 291
Human      RCGVHPGPGTFLFMGWSRFGEARLGCAPRFQEFRRAYEAARAAHLHPCEVALH 293
           ****:****.***********  **********  *.*.**  ::**:***:**.
```

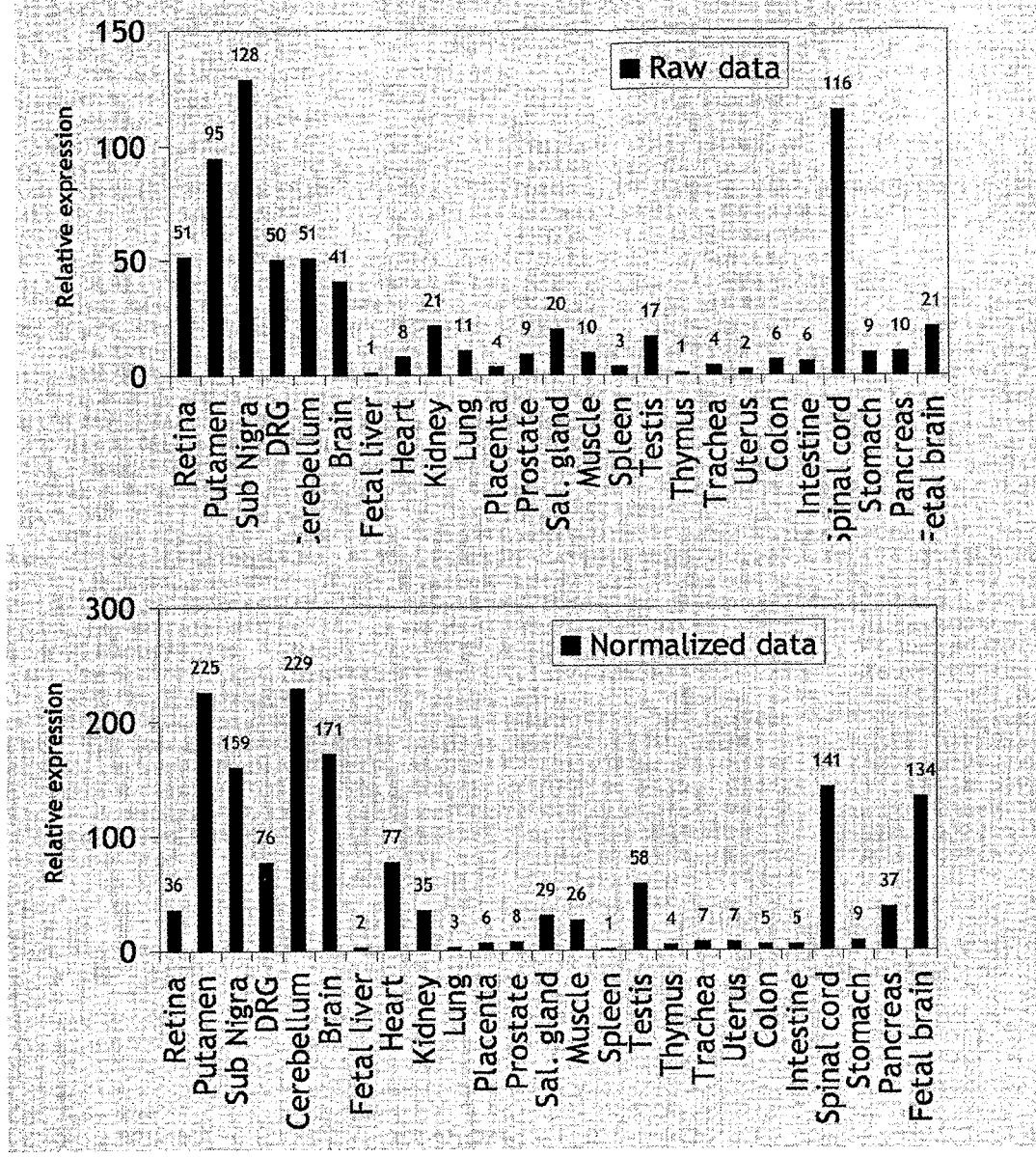

```
scoring matrix: BLOSUM50, gap penalties: -12/-2
42.3% identity;         Global alignment score: 747

10        20        30        40        50  *
Innog.  MRGAARAAWGRAGQPWPRPPAPGPPPPPLPLLLLLLAGLLGGAG-AQYSSDRCSWKGSGL
                                   :  ::  :  :::. :.  : ::  .::::.::::
NsG33   -----------------------MGFPAAALLCALCCGLLAPAARAGYSEERCSWRGSGL
                                           10        20        30

60        70   *    80        90       100      *110
Innog.  THEAHRKEVEQVYLRCAAGAVEWMYPTGALIVNLR-PNTFSPARHLTVCIRSFTDSSGAN
        :.:      :  :. : ::  ::::::.::.:::   ...:   :.    ::    .:.:         .::.
NsG33   TQEPGS--VGQLALACAEGAVEWLYPAGALRLTLGGPDPR--ARPGIACLRPVRPFAGAQ
          40        50        60        70        80        90

120       130       140   *    150       160       170
Innog.  IYLEKTG-ELRLLVPDGDGRPGRVQC--FG-LEQGGLFVEATPQQDIGRRTTGFQYELVR
        ..  :...:  :.::.  .: :  :.    .:     :.  .::..:::.:::.::...:..::  .
NsG33   VFAERAGGALELLLAEGPG-PAGGRCVRWGPRERRALFLQATPHQDISRRVAAFRFELRE
             100       110       120       130       140       150

180       190       200       210       220
Innog.  RHRAS---DLHELSAP--CRPCSDTEVLLAVCTSDFAVRGSIQQVTHEPERQDSAIHLRV
        :       . :  :..  ::::::.:.:::.:::::::...:   :. :::. :  :..:.: . .
NsG33   DGRPELPPQAHGLGVDGACRPCSDAELLLAACTSDFVIHGIIHGVTHDVELQESVITVVA
                  160       170*   *  180    *    190       200       210

230       240       250       260       270       280
Innog.  SRLYRQKSRVFEPVPEGDGHWQG--RVRTLLECGVRPGHGDFLFTGHMHFGEARLGCAPR
        .:. ::    ..:.    ::      ::    .::  :.::::.:: :  :::   :.::::::::::::
NsG33   ARVLRQTPPLFQAGRSGD---QGLTSIRTPLRCGVHPGPGTFLFMGWSRFGEARLGCAPR
                  220       230        240    *    250       260        *

290       300    *  310
Innog.  FKDFQRMYRDAQERGLNPCEVGTD
        :...:.  :.  :.         :.:::::.
NsG33   FQEFRRAYEAARAAHLHPCEVALH
            270       280       290
```

```
  1 ccacgcgtcc gcccacgcgt ccgcgcttct ttgcgcgctc tgttgcggcc tcctggccgc gtccgctcac gctgctact cggaagaccg ctgcagctgg
    >>...  h   a   s   a   h   a   s   a   l   l   c   a   l   c   c   g   l   l   a   a   s   a   h   a   g   y   s   e   d   r   c   s   w
    ^                                                                         .CDS............................................................
101 aggggcagcg gtttgaccca ggagcctggc agcgtgggc agctgaccct ggactgtact gaggcgcta tcgagtggct gtaccagct gggggcctgc
    ^   r   g   s   g   l   t   q   e   p   g   s   v   g   q   l   t   l   d   c   t   e   g   a   i   e   w   l   y   p   a   g   a   l
                                                                              .CDS............................................................
201 gcctgaccct gggcgcccc gatccgggca cacggcccag catcgtctgt ctgcccag agcggcctt cgctggtgcc caggtcttcg ctgaacgtat
    ^   r   l   t   l   g   g   p   d   p   g   t   r   p   s   i   v   c   l   r   p   e   r   p   f   a   g   a   q   v   f   a   e   r
                                                                              .CDS............................................................
301 gaccggcaat ctagagttgc tactggccga ggcccggac ctggctgggg gccgctgcat gcgctgggt gccgcgagc gccgagccct tttcctcag
    m   t   g   n   l   e   l   l   l   a   e   g   p   d   l   a   g   r   c   m   r   w   g   p   r   e   r   r   a   l   f   l   q
    ^                                                                         .CDS............................................................
401 gccacaccac accggcgacat cagccgcaga gttgctgcct tccgtttga actgcacgag cagaaatgtc tcccaggct caaggtcttg
    ^   a   t   p   h   r   d   i   s   r   r   v   a   a   f   r   f   e   l   h   e   d   q   r   a   e   m   s   p   q   a   q   g   l
                                                                              .CDS............................................................
501 gtgtggatgg tgcctgcagg ccctgcagtg atgccgagct cctcctggct gcatgcacca gtgatttgt gatccacggg accatccatg gggtcgccca
    ^   g   v   d   g   a   c   r   p   c   s   d   a   e   l   l   l   a   a   c   t   s   d   f   v   i   h   g   t   i   h   g   v   a
                                                                              .CDS............................................................
601 tgacacagag ctgcaagaat cagtcatcac tgtggtggt gctcgtgtca tccgccagac actgccactg ttcaaggaag ggagctcgga gggccaagc
    ^   h   d   t   e   l   q   e   s   v   i   t   v   v   v   v   a   r   v   i   r   q   t   l   p   l   f   k   e   g   s   s   e   g
                                                                              .CDS............................................................
701 cgggcctcca ttcgtacctt gctgcctgt ctggccagg ctggccgtc ctggcccagg ctccttcctc ttcatgggct ggagccgatt tgccgtgggct
    ^   r   a   s   i   r   t   l   l   r   c   g   v   r   p   g   p   g   s   f   l   f   m   g   w   s   r   f   g   e   a   w   l   g
                                                                              .CDS............................................................
801 gtgctccccg cttccaagag ttcagccgtg tctattcagc tgctctcacg accatgtga gatgcactg gactgagaga cctggagca
    ^   c   a   p   r   f   q   e   f   s   r   v   y   s   a   a   l   t   h   l   n   p   c   e   m   a   l   d   -
                                                                              .CDS.................>>
901 agccctgat ggaccttctt ctggagatgg gtgttgggg agggtgatgg gagggtgggt gagaagggt tggctcggat ggcatcctgg tacccacagt
1001 gagctggtag aatactaagt aatctggacc ataaaaaaa aaaaaaaa
```

```
  1 atgctggtag cggcgcttct ctgcgcgctg tgctgcggcc tcttggctgc gtcgctcga gctggctact ccgaggaccg ctgcagctgg agggcagcg
    >>...  m  l  v     a  a  l     l  c  c  g     l  l  a     a  s  r     a  g  y     s  e  d     r  c  s  w     r  g  s
    ...CDS........................................................................................................>

101 gtttgaccca ggaacctggc agcgtgggc agctgacccct ggattgtact gagggtgcta tcgagtggct gtatccagct ggggcgctgc gcctgactct
    >...  g  l  t     q  e  p  g     s  v  g     q  l  t     l  d  c  t     e  g  a     i  e  w     l  y  p  a     g  a  l  r  l  t
    ...CDS........................................................................................................>

201 aggcggctct gatccgggca cgcggggca catcgtctgt ctgcgcccaa cacggccctt cgctggtgcc caggtcttcg ctgaacggat ggccggcaac
    ...  g  g  s     d  p  g     t  r  p     s  i  v  c     l  r  p     t  r  p     f  a  g  a     q  v  f     a  e  r  m  a  g  n
    ...CDS........................................................................................................>

301 ctagagttgc tactggccga gggccaaggc gctgctggga gccgctgcat gcgctggggt cctcgcgagc gccagccct tttcctgcag gccacgccac
    >...  l  e  l  l  a     e  g  q     g  l  a  g     r  c  m  r  w  g     p  r  e     r  r  a     l  f  l  q     a  t  p
    ...CDS........................................................................................................>

401 accggacat cagccgcaga gttgctgcct tccaatttga actgcacgag gaccaacgtg cagaaatgtc tcccaggcc caaggtttg gtgtggatgg
    >...  h  r  d  i  s  r  r     v  a  a     f  q  f  e  l  h  e     d  q  r     a  e  m     s  p  q  a     q  g  f     g  v  d
    ...CDS........................................................................................................>

501 tgcctgcagg ccctgcagtg atgccgagct ccttctgact gcatgcacca gtgactttgt gatcactggg accatccatg ggtcgtcca tgacatggag
    >...  a  c  r  p  c  s     d  a  e     l  l  l  t     a  c  t     s  d  f  v  i  h  g     t  i  h     g  v  v     h  d  m  e
    ...CDS........................................................................................................>

601 ctgcaagaat cagtcatcac tgtggtggcc actcgtgtca tccgccagac actgcaccactg ttccaggaag ggagctcgga gggccgggc caggcctccg
    >...  l  q  e     s  v  i  t     v  v  a     t  r  v     i  r  q  t  l  p  l     f  q  e     g  s  s     e  g  r  g     q  a  s
    ...CDS........................................................................................................>

701 ttcgtaccctt gttgcctgt ggtgtcgtc ctggccagg ctccttcctc ttcatgggct ggagccgatt tggcgaagct tggctggct gcgctccccg
    >...  v  r  t     l  l  r  c     g  v  r     p  g  p     g  s  f  l     f  m  g     w  s  r     f  g  e  a     w  l  g     c  a  p
    ...CDS........................................................................................................>

801 cttccaagag ttcagccgtg tctattcagc tgctctcgcg gcccacctca accatgtga ggtggcactg gactgagaga cctggagca agccctggat
    >...  r  f  q  e     f  s  r     v  y  s     a  a  l  a     a  h  l     n  p  c     e  v  a  l     d  -
    ...CDS........................................................................>>

901 ggatcttcct ctggggatgg ggtgttgggg aggggtgata ggagggtggg tgggaaggt tggaagggt gtggctcaga tggcatcctg gtacccacag tgaggtggta 1001 gaatactaaa taacctggat cacacc
```

Fig 8

SEQUENCE LISTING

<160> NUMBER OF SEQ ID NOS: 60

<210> SEQ ID NO 1
<211> LENGTH: 2508
<212> TYPE: DNA
<213> ORGANISM: Homo sapiens

<400> SEQUENCE: 1

```
actggccgac acgccgcagg ccccgccccc ttcccgaccc gctccaaggc ggccccggcg      60
ctggggctgc gcggcaggcg gagcggccgc gggcttgggg gcttcgccgg ggccgggcgg     120
ccggcgcccc cggctgctcc cgccgccgcc cggaccccgcg ccccgccggg gcagcggtgg     180
tgagagcccc gactccccgg acgccgcccg ccgtgccatg gggttcccgg ccgcggcgct     240
gctctgcgcg ctgtgctgcg gcctcctggc cccggctgcc cgcgccggct actccgagga     300
gcgctgcagc tggaggggca ggtacggtcc ggggggctgt ccccgcactt aggacgggt     360
```

```
gcgctgcggc taggacccc caggcgcccc tcggagcgcg cagagcgctg ggccggtttc    420
cccatccgcg aggcggcctc gggagggagc gggggctgcg ccgggcgggg acccgccccc    480
gtctcagcgc cccgtcccgt cctgtcccca gcggcctcac ccaggagccc ggcagcgtgg    540
ggcagctggc cctggcctgt gcggaggcg cggttgagtg gctgtacccg gctggggcgc    600
tgcgcctgac cctgggcggc cccgatccca gagcgcggcc cggcatcgcc tgtctgcggc    660
cggtgcggcc cttcgcgggc gcccaggtct tcgcggagcg cgcaggggc gccctggagc    720 tgctgctggc cgagggcccg ggcccggcag ggggccgctg cgtgcgctgg ggtccccgcg    780
agcgccgggc cctcttcctg caggccacgc cgcaccagga catcagccgc cgcgtggccg    840
ccttccgctt tgagctgcgc gaggacgggc gccccgagct gccccgcag gcccacggtc    900 tcggcgtaga cggtgagtgg cggtctggtt gggacagggt gggagtcccg aagtcttacc    960
ctgcctgggc ttggcgggaa tgtgccttgt cggccccact gcagaaggaa aaagtgagct   1020 acaaggttg gatgggcttg tcaggccaca cagcctggga ctgctgggga gggatggcct   1080
ccccgccctc ccttcccgat tcatctctgg aaagagctgg caggggcaga gtggagggaa   1140
ggggaggccg ggcccagcaa tcctgggcct ctggtccctg aacggttggg ggaagagatg   1200
gtggggacag aatcgaagcc tccggccaaa gctgtccggg gctccctggc ccagcggtga   1260
cctctctccc ctccccagc caaccaaca aaagtccagt gtgcagcccg gtcaccatgg   1320
agacgccgct cgcctccctg cagggcacca ggcccagctc ttgcttggct ctcctggagc   1380
ttggcgcctg accctgaaag ggatgggctc tcgctattct gccccctggc cctgggccag   1440
ggaccccaga ccaccttcc tctgccccca cttcctatca ccctagctgg gctgctgctc   1500
ttcagacctc agatccggga aactagaggg gtcccagatg ctggggtgca tatgtcagat   1560
gggagtgcag gagggcggcc caggacagct gatcgctagg catggcccc aggcccacgt   1620 ctgtgtgcat tcctgccttg gaggtacgcg cctgcaagtg tgtttcctga gtacaggtgt   1680
cgccgagggc gtgcacatct gctgtgtagc tctctgggac cccaggtgc catcaggccc   1740 tgagcgtggg ctctgctcat ttgcctgctg cctcctgccg cttgtgcgga caagggacgg   1800 ggcctgggggt gatgccggga gagggcaggg cctctcctca ccaccccctc tgcatgccag   1860
gtgcctgcag gccctgcagc gacgctgagc tgctcctggc cgcatgcacc agcgacttcg   1920
gtgagtgtcc ccgccatggg gggagcctgg agcctgcctt cccctgaatg cctaccgcag   1980
ccacatgcct ccccacagta attcacggga tcatccatgg ggtcacccat gacgtggagc   2040
tgcaggagtc tgtcatcact gtggtggccg cccgtgtcct ccgccagaca ccgccgctgt   2100
tccaggcggg gcgatccggg gaccaggggc tgacctccat tcgtacccca ctgcgctgtg   2160
gcgtccaccc gggcccaggc accttcctct tcatgggctg gagccgcttt ggggaggccc   2220
ggctgggctg tgccccacga ttccaggagt tccgccgtgc ctacgaggct gcccgtgctg   2280
cccacctcca cccctgcgag gtggcgctgc actgaggggc tgggtgctgg ggagggctg   2340 gtaggaggga gggtgggccc actgctttgg aggtgatggg actatcaata agaactctgt   2400
tcacgcaagc tgctgtggac ctggtctcct gtgtccagcc cagccttggg cctgcctcgc   2460
agctgtgagg atggctccaa ttcctgcctc ctggcgggag actgaggc                2508

<210> SEQ ID NO 2
<211> LENGTH: 1109
<212> TYPE: DNA
<213> ORGANISM: Homo sapiens
<220> FEATURE:
```

<221> NAME/KEY: CDS
<222> LOCATION: (118)..(999)

<400> SEQUENCE: 2

```
gcttcgccgg ggccgggcgg ccggcgcccc cggctgctcc cgccgccgcc cggacccgcg      60
ccccgccggg gcagcggtgg tgagagcccc gactccccgg acgccgcccg ccgtgcc        117
```

| | | | | | | | | | | | | | | | | |
|---|---|---|---|---|---|---|---|---|---|---|---|---|---|---|---|---|
| atg | ggg | ttc | ccg | gcc | gcg | gcg | ctg | ctc | tgc | gcg | ctg | tgc | tgc | ggc | ctc | 165 |
| Met | Gly | Phe | Pro | Ala | Ala | Ala | Leu | Leu | Cys | Ala | Leu | Cys | Cys | Gly | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctg | gcc | ccg | gct | gcc | cgc | gcc | ggc | tac | tcc | gag | gag | cgc | tgc | agc | tgg | 213 |
| Leu | Ala | Pro | Ala | Ala | Arg | Ala | Gly | Tyr | Ser | Glu | Glu | Arg | Cys | Ser | Trp | |
| | | | 20 | | | | | 25 | | | | | 30 | | | |

| | | | | | | | | | | | | | | | | |
|---|---|---|---|---|---|---|---|---|---|---|---|---|---|---|---|---|
| agg | ggc | agc | ggc | ctc | acc | cag | gag | ccc | ggc | agc | gtg | ggg | cag | ctg | gcc | 261 |
| Arg | Gly | Ser | Gly | Leu | Thr | Gln | Glu | Pro | Gly | Ser | Val | Gly | Gln | Leu | Ala | |
| | | 35 | | | | | 40 | | | | | 45 | | | | |

| | | | | | | | | | | | | | | | | |
|---|---|---|---|---|---|---|---|---|---|---|---|---|---|---|---|---|
| ctg | gcc | tgt | gcg | gag | ggc | gcg | gtt | gag | tgg | ctg | tac | ccg | gct | ggg | gcg | 309 |
| Leu | Ala | Cys | Ala | Glu | Gly | Ala | Val | Glu | Trp | Leu | Tyr | Pro | Ala | Gly | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| ctg | cgc | ctg | acc | ctg | ggc | ggc | ccc | gat | ccc | aga | gcg | cgg | ccc | ggc | atc | 357 |
| Leu | Arg | Leu | Thr | Leu | Gly | Gly | Pro | Asp | Pro | Arg | Ala | Arg | Pro | Gly | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gcc | tgt | ctg | cgg | ccg | gtg | cgg | ccc | ttc | gcg | ggc | gcc | cag | gtc | ttc | gcg | 405 |
| Ala | Cys | Leu | Arg | Pro | Val | Arg | Pro | Phe | Ala | Gly | Ala | Gln | Val | Phe | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| gag | cgc | gca | ggg | ggc | gcc | ctg | gag | ctg | ctg | ctg | gcc | gag | ggc | ccg | ggc | 453 |
| Glu | Arg | Ala | Gly | Gly | Ala | Leu | Glu | Leu | Leu | Leu | Ala | Glu | Gly | Pro | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| ccg | gca | ggg | ggc | cgc | tgc | gtg | cgc | tgg | ggt | ccc | cgc | gag | cgc | cgg | gcc | 501 |
| Pro | Ala | Gly | Gly | Arg | Cys | Val | Arg | Trp | Gly | Pro | Arg | Glu | Arg | Arg | Ala | |
| | | 115 | | | | | 120 | | | | | 125 | | | | |

| | | | | | | | | | | | | | | | | |
|---|---|---|---|---|---|---|---|---|---|---|---|---|---|---|---|---|
| ctc | ttc | ctg | cag | gcc | acg | ccg | cac | cag | gac | atc | agc | cgc | cgc | gtg | gcc | 549 |
| Leu | Phe | Leu | Gln | Ala | Thr | Pro | His | Gln | Asp | Ile | Ser | Arg | Arg | Val | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| gcc | ttc | cgc | ttt | gag | ctg | cgc | gag | gac | ggg | cgc | ccc | gag | ctg | ccc | ccg | 597 |
| Ala | Phe | Arg | Phe | Glu | Leu | Arg | Glu | Asp | Gly | Arg | Pro | Glu | Leu | Pro | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cag | gcc | cac | ggt | ctc | ggc | gta | gac | ggt | gcc | tgc | agg | ccc | tgc | agc | gac | 645 |
| Gln | Ala | His | Gly | Leu | Gly | Val | Asp | Gly | Ala | Cys | Arg | Pro | Cys | Ser | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| gct | gag | ctg | ctc | ctg | gcc | gca | tgc | acc | agc | gac | ttc | gta | att | cac | ggg | 693 |
| Ala | Glu | Leu | Leu | Leu | Ala | Ala | Cys | Thr | Ser | Asp | Phe | Val | Ile | His | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| atc | atc | cat | ggg | gtc | acc | cat | gac | gtg | gag | ctg | cag | gag | tct | gtc | atc | 741 |
| Ile | Ile | His | Gly | Val | Thr | His | Asp | Val | Glu | Leu | Gln | Glu | Ser | Val | Ile | |
| | | 195 | | | | | 200 | | | | | 205 | | | | |

| | | | | | | | | | | | | | | | | |
|---|---|---|---|---|---|---|---|---|---|---|---|---|---|---|---|---|
| act | gtg | gtg | gcc | gcc | cgt | gtc | ctc | cgc | cag | aca | ccg | ccg | ctg | ttc | cag | 789 |
| Thr | Val | Val | Ala | Ala | Arg | Val | Leu | Arg | Gln | Thr | Pro | Pro | Leu | Phe | Gln | |
| | 210 | | | | | 215 | | | | | 220 | | | | | |

| | | | | | | | | | | | | | | | | |
|---|---|---|---|---|---|---|---|---|---|---|---|---|---|---|---|---|
| gcg | ggg | cga | tcc | ggg | gac | cag | ggg | ctg | acc | tcc | att | cgt | acc | cca | ctg | 837 |
| Ala | Gly | Arg | Ser | Gly | Asp | Gln | Gly | Leu | Thr | Ser | Ile | Arg | Thr | Pro | Leu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cgc | tgt | ggc | gtc | cac | ccg | ggc | cca | ggc | acc | ttc | ctc | ttc | atg | ggc | tgg | 885 |
| Arg | Cys | Gly | Val | His | Pro | Gly | Pro | Gly | Thr | Phe | Leu | Phe | Met | Gly | Trp | |
| | | | | 245 | | | | | 250 | | | | | 255 | | |

| | | | | | | | | | | | | | | | | |
|---|---|---|---|---|---|---|---|---|---|---|---|---|---|---|---|---|
| agc | cgc | ttt | ggg | gag | gcc | cgg | ctg | ggc | tgt | gcc | cca | cga | ttc | cag | gag | 933 |
| Ser | Arg | Phe | Gly | Glu | Ala | Arg | Leu | Gly | Cys | Ala | Pro | Arg | Phe | Gln | Glu | |
| | | | 260 | | | | | 265 | | | | | 270 | | | |

| | | | | | | | | | | | | | | | | |
|---|---|---|---|---|---|---|---|---|---|---|---|---|---|---|---|---|
| ttc | cgc | cgt | gcc | tac | gag | gct | gcc | cgt | gct | gcc | cac | ctc | cac | ccc | tgc | 981 |
| Phe | Arg | Arg | Ala | Tyr | Glu | Ala | Ala | Arg | Ala | Ala | His | Leu | His | Pro | Cys | |

-continued

```
                275                 280                 285
gag gtg gcg ctg cac tga ggggctgggt gctggggagg ggctggtagg            1029
Glu Val Ala Leu His
    290 agggagggtg ggcccactgc tttggaggtg atgggactat caataagaac tctgttcacg   1089 caaaaaaaaa aaaaaaaaa                                                1109
```

<210> SEQ ID NO 3
<211> LENGTH: 293
<212> TYPE: PRT
<213> ORGANISM: Homo sapiens

<400> SEQUENCE: 3

```
Met Gly Phe Pro Ala Ala Ala Leu Leu Cys Ala Leu Cys Cys Gly Leu
1               5                   10                  15

Leu Ala Pro Ala Ala Arg Ala Gly Tyr Ser Glu Glu Arg Cys Ser Trp
            20                  25                  30

Arg Gly Ser Gly Leu Thr Gln Glu Pro Gly Ser Val Gly Gln Leu Ala
        35                  40                  45

Leu Ala Cys Ala Glu Gly Ala Val Glu Trp Leu Tyr Pro Ala Gly Ala
    50                  55                  60

Leu Arg Leu Thr Leu Gly Gly Pro Asp Pro Arg Ala Arg Pro Gly Ile
65                  70                  75                  80

Ala Cys Leu Arg Pro Val Arg Pro Phe Ala Gly Ala Gln Val Phe Ala
                85                  90                  95

Glu Arg Ala Gly Gly Ala Leu Glu Leu Leu Ala Glu Gly Pro Gly
            100                 105                 110

Pro Ala Gly Gly Arg Cys Val Arg Trp Gly Pro Arg Glu Arg Arg Ala
        115                 120                 125

Leu Phe Leu Gln Ala Thr Pro His Gln Asp Ile Ser Arg Arg Val Ala
    130                 135                 140

Ala Phe Arg Phe Glu Leu Arg Glu Asp Gly Arg Pro Glu Leu Pro Pro
145                 150                 155                 160

Gln Ala His Gly Leu Gly Val Asp Gly Ala Cys Arg Pro Cys Ser Asp
                165                 170                 175

Ala Glu Leu Leu Leu Ala Ala Cys Thr Ser Asp Phe Val Ile His Gly
            180                 185                 190

Ile Ile His Gly Val Thr His Asp Val Glu Leu Gln Glu Ser Val Ile
        195                 200                 205

Thr Val Val Ala Ala Arg Val Leu Arg Gln Thr Pro Pro Leu Phe Gln
    210                 215                 220

Ala Gly Arg Ser Gly Asp Gln Gly Leu Thr Ser Ile Arg Thr Pro Leu
225                 230                 235                 240

Arg Cys Gly Val His Pro Gly Pro Gly Thr Phe Leu Phe Met Gly Trp
                245                 250                 255

Ser Arg Phe Gly Glu Ala Arg Leu Gly Cys Ala Pro Arg Phe Gln Glu
            260                 265                 270

Phe Arg Arg Ala Tyr Glu Ala Ala Arg Ala Ala His Leu His Pro Cys
        275                 280                 285

Glu Val Ala Leu His
    290
```

<210> SEQ ID NO 4
<211> LENGTH: 270
<212> TYPE: PRT

<213> ORGANISM: Homo sapiens

<400> SEQUENCE: 4

```
Gly Tyr Ser Glu Glu Arg Cys Ser Trp Arg Gly Ser Gly Leu Thr Gln
1               5                   10                  15

Glu Pro Gly Ser Val Gly Gln Leu Ala Leu Ala Cys Ala Glu Gly Ala
            20                  25                  30

Val Glu Trp Leu Tyr Pro Ala Gly Ala Leu Arg Leu Thr Leu Gly Gly
        35                  40                  45

Pro Asp Pro Arg Ala Arg Pro Gly Ile Ala Cys Leu Arg Pro Val Arg
    50                  55                  60

Pro Phe Ala Gly Ala Gln Val Phe Ala Glu Arg Ala Gly Gly Ala Leu
65                  70                  75                  80

Glu Leu Leu Leu Ala Glu Gly Pro Gly Pro Ala Gly Gly Arg Cys Val
                85                  90                  95

Arg Trp Gly Pro Arg Glu Arg Arg Ala Leu Phe Leu Gln Ala Thr Pro
            100                 105                 110

His Gln Asp Ile Ser Arg Arg Val Ala Ala Phe Arg Phe Glu Leu Arg
        115                 120                 125

Glu Asp Gly Arg Pro Glu Leu Pro Pro Gln Ala His Gly Leu Gly Val
    130                 135                 140

Asp Gly Ala Cys Arg Pro Cys Ser Asp Ala Glu Leu Leu Leu Ala Ala
145                 150                 155                 160

Cys Thr Ser Asp Phe Val Ile His Gly Ile Ile His Gly Val Thr His
                165                 170                 175

Asp Val Glu Leu Gln Glu Ser Val Ile Thr Val Val Ala Ala Arg Val
            180                 185                 190

Leu Arg Gln Thr Pro Pro Leu Phe Gln Ala Gly Arg Ser Gly Asp Gln
        195                 200                 205

Gly Leu Thr Ser Ile Arg Thr Pro Leu Arg Cys Gly Val His Pro Gly
    210                 215                 220

Pro Gly Thr Phe Leu Phe Met Gly Trp Ser Arg Phe Gly Glu Ala Arg
225                 230                 235                 240

Leu Gly Cys Ala Pro Arg Phe Gln Glu Phe Arg Arg Ala Tyr Glu Ala
                245                 250                 255

Ala Arg Ala Ala His Leu His Pro Cys Glu Val Ala Leu His
            260                 265                 270
```

<210> SEQ ID NO 5
<211> LENGTH: 166
<212> TYPE: PRT
<213> ORGANISM: Homo sapiens

<400> SEQUENCE: 5

```
Ala Leu Phe Leu Gln Ala Thr Pro His Gln Asp Ile Ser Arg Arg Val
1               5                   10                  15

Ala Ala Phe Arg Phe Glu Leu Arg Glu Asp Gly Arg Pro Glu Leu Pro
            20                  25                  30

Pro Gln Ala His Gly Leu Gly Val Asp Gly Ala Cys Arg Pro Cys Ser
        35                  40                  45

Asp Ala Glu Leu Leu Leu Ala Ala Cys Thr Ser Asp Phe Val Ile His
    50                  55                  60

Gly Ile Ile His Gly Val Thr His Asp Val Glu Leu Gln Glu Ser Val
65                  70                  75                  80

Ile Thr Val Val Ala Ala Arg Val Leu Arg Gln Thr Pro Pro Leu Phe
```

```
                    85                  90                  95
Gln Ala Gly Arg Ser Gly Asp Gln Gly Leu Thr Ser Ile Arg Thr Pro
            100                 105                 110

Leu Arg Cys Gly Val His Pro Gly Pro Gly Thr Phe Leu Phe Met Gly
        115                 120                 125

Trp Ser Arg Phe Gly Glu Ala Arg Leu Gly Cys Ala Pro Arg Phe Gln
    130                 135                 140

Glu Phe Arg Arg Ala Tyr Glu Ala Ala Arg Ala Ala His Leu His Pro
145                 150                 155                 160

Cys Glu Val Ala Leu His
                165

<210> SEQ ID NO 6
<211> LENGTH: 2322
<212> TYPE: DNA
<213> ORGANISM: Mus musculus
<220> FEATURE:
<221> NAME/KEY: misc_feature
<222> LOCATION: (1)..(78)
<223> OTHER INFORMATION: n is a, c, g, or t

<400> SEQUENCE: 6
nnnnnnnnnn nnnnnnnnnn nnnnnnnnnn nnnnnnnnnn nnnnnnnnnn nnnnnnnnnn      60
nnnnnnnnnn nnnnnnnncc cctaaccatg ctggtagcca cgcttctttg cgcgctctgt     120
tgcggcctcc tggccgcgtc cgctcacgct ggctactcgg aagaccgctg cagctggagg     180
ggcaggtacc aggagggact gcggggaggg ttgtgggttt atttatttat ttatttatt     240 ttatttactt cttgggttgg agggttccct cccacttgga actgaggaaa cgcagacttc     300
aatgtcctgt tacacagagt agaagcagat gttggtagcc gcgggaaaag ggatgagcgg     360
gctagggaac gagggtcacc cacctgagaa ccaccgtcct gtcccagcg gtttgaccca     420 ggagcctggc agcgtggggc agctgaccct ggactgtact gagggcgcta tcgagtggct     480
gtacccagct ggggcgctgc gcctgaccct gggcggcccc gatccgggca cacggcccag     540
catcgtctgt ctgcgcccag agcggcccct cgctggtgcc caggtcttcg ctgaacgtat     600
gaccggcaat ctagagttgc tactggccga gggcccggac ctggctgggg gccgctgcat     660
gcgctggggt cccgcgagc gccgagccct tttcctgcag gccacaccac accgcgacat     720
cagccgcaga gttgctgcct tccgttttga actgcacgag gaccaacgtg cagaaatgtc     780
tccccaggct caaggtcttg gtgtggatgg tgagtgatta tgagactggc tgggtgtcag     840
aaattggccc tccacactga cctgatggga ctgggccttg ccacccatt gcatggagag     900 tccttctgta gcttgacaga ggccactccg gtggagagca tagtggcttc caggtcgtaa     960
ggaggtgagt tggaagtgcc cccgcctttc tctcctcctc ctcttaaaag attcggttta    1020
ggaaaagagc aggaggggc aaatgcccga gaggccagcc ctgggtctct ggtttctgaa    1080
ggattggggg aagggttaag ctgaggcaga atcaaagcct atggccaagg ctgtccaggg    1140
ctccctggcc tggtggtgac ctccttcccc tcccccaag cccagccaac aaaagtccag    1200
tgtgcctctt cgtcaccatg gagactgcct gccctgcctc cctgcagggc accaggccca    1260
gtgctttgct cttctggaac ttgtagcctg acctgcagg gaatgaatgg ctctctgact    1320
gttctgccct agctagagac cccccgaac tggagtccac tagaatatcc ctagctagag    1380
ctgggaggtc acagaacgtt tcccagtgtt agtctgagtt tatgagatgg taccaagcct    1440
gtgtatgagg cactgaggtg cccatcagta ggcatgtacc tgcagggtgt cttcaggcta    1500
```

-continued

```
taggatgctg ggagaagggt ttagtctctt gctcctgtac cttttcctct tgggaggagc    1560
tgtgggctcg tgctgagaga tcacaggcct ggctgatgac ctgccttgca tgctaggtgc    1620
ctgcaggccc tgcagtgatg ccgagctcct cctggctgca tgccaccagtg attttggtga   1680
gtgtttctgt tgcgggagag cttagggtct gcctcacatt cccacgtgcc caccactggc    1740
caccatgtct cctcgtagtg atccacggga ccatccatgg ggtcgcccat gacacagagc    1800
tgcaagaatc agtcatcact gtggtggttg ctcgtgtcat ccgccagaca ctgccactgt    1860
tcaaggaagg gagctcggag ggccaaggcc gggcctccat tcgtaccttg ctgcgctgtg    1920
gtgtgcgtcc tggcccaggc tccttcctct tcatgggctg gagccgattt ggcgaagctt    1980
ggctgggctg tgctccccgc ttccaagagt tcagccgtgt ctattcagct gctctcacga    2040
cccatctcaa cccatgtgag atggcactgg actgagagac ctgggagcaa gccctggatg    2100
gaccttcttc tggagatggg gtgttgggga gggtgatggg agggtgggtg agaagggtgt    2160
ggctcggatg gcatcctggt acccacagtg agctggtaga atactaagta atctggacca    2220
taccagccac tgtagtcatg gtcttctgtg gcaggcagca tacccagctc tgtgcctgcc    2280
tcactttgtc tactctccag tctgctgccc ttctaaccct tc                       2322
```

```
<210> SEQ ID NO 7
<211> LENGTH: 1048
<212> TYPE: DNA
<213> ORGANISM: Mus musculus
<220> FEATURE:
<221> NAME/KEY: CDS
<222> LOCATION: (2)..(886)

<400> SEQUENCE: 7
```

```
c cac gcg tcc gcc cac gcg tcc gcg ctt ctt tgc gcg ctc tgt tgc ggc      49
  His Ala Ser Ala His Ala Ser Ala Leu Leu Cys Ala Leu Cys Cys Gly
  1               5                  10                  15 ctc ctg gcc gcg tcc gct cac gct ggc tac tcg gaa gac cgc tgc agc        97
Leu Leu Ala Ala Ser Ala His Ala Gly Tyr Ser Glu Asp Arg Cys Ser
         20                  25                  30 tgg agg ggc agc ggt ttg acc cag gag cct ggc agc gtg ggg cag ctg       145
Trp Arg Gly Ser Gly Leu Thr Gln Glu Pro Gly Ser Val Gly Gln Leu
     35                  40                  45 acc ctg gac tgt act gag ggc gct atc gag tgg ctg tac cca gct ggg       193
Thr Leu Asp Cys Thr Glu Gly Ala Ile Glu Trp Leu Tyr Pro Ala Gly
 50                  55                  60 gcg ctg cgc ctg acc ctg ggc ggc ccc gat ccg ggc aca cgg ccc agc       241
Ala Leu Arg Leu Thr Leu Gly Gly Pro Asp Pro Gly Thr Arg Pro Ser
 65                  70                  75                  80 atc gtc tgt ctg cgc cca gag cgg ccc ttc gct ggt gcc cag gtc ttc       289
Ile Val Cys Leu Arg Pro Glu Arg Pro Phe Ala Gly Ala Gln Val Phe
                 85                  90                  95 gct gaa cgt atg acc ggc aat cta gag ttg cta ctg gcc gag ggc ccg       337
Ala Glu Arg Met Thr Gly Asn Leu Glu Leu Leu Leu Ala Glu Gly Pro
            100                 105                 110 gac ctg gct ggg ggc cgc tgc atg cgc tgg ggt ccc cgc gag cgc cga       385
Asp Leu Ala Gly Gly Arg Cys Met Arg Trp Gly Pro Arg Glu Arg Arg
        115                 120                 125 gcc ctt ttc ctg cag gcc aca cca cac cgc gac atc agc cgc aga gtt       433
Ala Leu Phe Leu Gln Ala Thr Pro His Arg Asp Ile Ser Arg Arg Val
    130                 135                 140 gct gcc ttc cgt ttt gaa ctg cac gag gac caa cgt gca gaa atg tct       481
Ala Ala Phe Arg Phe Glu Leu His Glu Asp Gln Arg Ala Glu Met Ser
145                 150                 155                 160
```

| | | |
|---|---|---|
| ccc cag gct caa ggt ctt ggt gtg gat ggt gcc tgc agg ccc tgc agt<br>Pro Gln Ala Gln Gly Leu Gly Val Asp Gly Ala Cys Arg Pro Cys Ser<br>                165                      170                175 | 529 |
| gat gcc gag ctc ctg ctg gct gca tgc acc agt gat ttt gtg atc cac<br>Asp Ala Glu Leu Leu Leu Ala Ala Cys Thr Ser Asp Phe Val Ile His<br>180                      185                      190 | 577 |
| ggg acc atc cat ggg gtc gcc cat gac aca gag ctg caa gaa tca gtc<br>Gly Thr Ile His Gly Val Ala His Asp Thr Glu Leu Gln Glu Ser Val<br>                195                      200                205 | 625 |
| atc act gtg gtg gtt gct cgt gtc atc cgc cag aca ctg cca ctg ttc<br>Ile Thr Val Val Val Ala Arg Val Ile Arg Gln Thr Leu Pro Leu Phe<br>210                      215                      220 | 673 |
| aag gaa ggg agc tcg gag ggc caa ggc cgg gcc tcc att cgt acc ttg<br>Lys Glu Gly Ser Ser Glu Gly Gln Gly Arg Ala Ser Ile Arg Thr Leu<br>225                      230                      235                240 | 721 |
| ctg cgc tgt ggt gtg cgt cct ggc cca ggc tcc ttc ctc ttc atg ggc<br>Leu Arg Cys Gly Val Arg Pro Gly Pro Gly Ser Phe Leu Phe Met Gly<br>                245                      250                255 | 769 |
| tgg agc cga ttt ggc gaa gct tgg ctg ggc tgt gct ccc cgc ttc caa<br>Trp Ser Arg Phe Gly Glu Ala Trp Leu Gly Cys Ala Pro Arg Phe Gln<br>260                      265                      270 | 817 |
| gag ttc agc cgt gtc tat tca gct gct ctc acg acc cat ctc aac cca<br>Glu Phe Ser Arg Val Tyr Ser Ala Ala Leu Thr Thr His Leu Asn Pro<br>                275                      280                285 | 865 |
| tgt gag atg gca ctg gac tga gagacctggg agcaagccct ggatggacct<br>Cys Glu Met Ala Leu Asp<br>290 | 916 |
| tcttctggag atggggtgtt ggggagggtg atgggagggt gggtgagaag ggtgtggctc | 976 |
| ggatggcatc ctggtaccca cagtgagctg gtagaatact aagtaatctg gaccataaaa | 1036 |
| aaaaaaaaaa aa | 1048 |

<210> SEQ ID NO 8
<211> LENGTH: 294
<212> TYPE: PRT
<213> ORGANISM: Mus musculus

<400> SEQUENCE: 8

His Ala Ser Ala His Ala Ser Ala Leu Leu Cys Ala Leu Cys Cys Gly
1                  5                    10                    15

Leu Leu Ala Ala Ser Ala His Ala Gly Tyr Ser Glu Asp Arg Cys Ser
                20                      25                    30

Trp Arg Gly Ser Gly Leu Thr Gln Glu Pro Gly Ser Val Gly Gln Leu
                35                      40                    45

Thr Leu Asp Cys Thr Glu Gly Ala Ile Glu Trp Leu Tyr Pro Ala Gly
50                      55                      60

Ala Leu Arg Leu Thr Leu Gly Gly Pro Asp Gly Thr Arg Pro Ser
65                  70                      75                    80

Ile Val Cys Leu Arg Pro Glu Arg Pro Phe Ala Gly Ala Gln Val Phe
                      85                      90                    95

Ala Glu Arg Met Thr Gly Asn Leu Glu Leu Leu Leu Ala Glu Gly Pro
                100                     105                  110

Asp Leu Ala Gly Gly Arg Cys Met Arg Trp Gly Pro Arg Glu Arg Arg
                115                     120                  125

Ala Leu Phe Leu Gln Ala Thr Pro His Arg Asp Ile Ser Arg Arg Val
        130                     135                     140

Ala Ala Phe Arg Phe Glu Leu His Glu Asp Gln Arg Ala Glu Met Ser
145                    150                     155                    160

```
Pro Gln Ala Gln Gly Leu Gly Val Asp Gly Ala Cys Arg Pro Cys Ser
                165                 170                 175

Asp Ala Glu Leu Leu Ala Ala Cys Thr Ser Asp Phe Val Ile His
            180                 185                 190

Gly Thr Ile His Gly Val Ala His Asp Thr Glu Leu Gln Glu Ser Val
        195                 200                 205

Ile Thr Val Val Val Ala Arg Val Ile Arg Gln Thr Leu Pro Leu Phe
    210                 215                 220

Lys Glu Gly Ser Ser Glu Gly Gln Gly Arg Ala Ser Ile Arg Thr Leu
225                 230                 235                 240

Leu Arg Cys Gly Val Arg Pro Gly Pro Gly Ser Phe Leu Phe Met Gly
                245                 250                 255

Trp Ser Arg Phe Gly Glu Ala Trp Leu Gly Cys Ala Pro Arg Phe Gln
            260                 265                 270

Glu Phe Ser Arg Val Tyr Ser Ala Ala Leu Thr Thr His Leu Asn Pro
        275                 280                 285

Cys Glu Met Ala Leu Asp
    290

<210> SEQ ID NO 9
<211> LENGTH: 270
<212> TYPE: PRT
<213> ORGANISM: Mus musculus

<400> SEQUENCE: 9

Gly Tyr Ser Glu Asp Arg Cys Ser Trp Arg Gly Ser Gly Leu Thr Gln
1               5                   10                  15

Glu Pro Gly Ser Val Gly Gln Leu Thr Leu Asp Cys Thr Glu Gly Ala
            20                  25                  30

Ile Glu Trp Leu Tyr Pro Ala Gly Ala Leu Arg Leu Thr Leu Gly Gly
        35                  40                  45

Pro Asp Pro Gly Thr Arg Pro Ser Ile Val Cys Leu Arg Pro Glu Arg
    50                  55                  60

Pro Phe Ala Gly Ala Gln Val Phe Ala Glu Arg Met Thr Gly Asn Leu
65                  70                  75                  80

Glu Leu Leu Leu Ala Glu Gly Pro Asp Leu Ala Gly Gly Arg Cys Met
                85                  90                  95

Arg Trp Gly Pro Arg Glu Arg Arg Ala Leu Phe Leu Gln Ala Thr Pro
            100                 105                 110

His Arg Asp Ile Ser Arg Arg Val Ala Ala Phe Arg Phe Glu Leu His
        115                 120                 125

Glu Asp Gln Arg Ala Glu Met Ser Pro Gln Ala Gln Gly Leu Gly Val
    130                 135                 140

Asp Gly Ala Cys Arg Pro Cys Ser Asp Ala Glu Leu Leu Ala Ala
145                 150                 155                 160

Cys Thr Ser Asp Phe Val Ile His Gly Thr Ile His Gly Val Ala His
                165                 170                 175

Asp Thr Glu Leu Gln Glu Ser Val Ile Thr Val Val Val Ala Arg Val
            180                 185                 190

Ile Arg Gln Thr Leu Pro Leu Phe Lys Glu Gly Ser Ser Glu Gly Gln
        195                 200                 205

Gly Arg Ala Ser Ile Arg Thr Leu Leu Arg Cys Gly Val Arg Pro Gly
    210                 215                 220

Pro Gly Ser Phe Leu Phe Met Gly Trp Ser Arg Phe Gly Glu Ala Trp
```

```
                    225                 230                 235                 240
Leu Gly Cys Ala Pro Arg Phe Gln Glu Phe Ser Arg Val Tyr Ser Ala
                245                 250                 255

Ala Leu Thr Thr His Leu Asn Pro Cys Glu Met Ala Leu Asp
            260                 265                 270

<210> SEQ ID NO 10
<211> LENGTH: 166
<212> TYPE: PRT
<213> ORGANISM: Mus musculus

<400> SEQUENCE: 10

Ala Leu Phe Leu Gln Ala Thr Pro His Arg Asp Ile Ser Arg Arg Val
1               5                   10                  15

Ala Ala Phe Arg Phe Glu Leu His Glu Asp Gln Arg Ala Glu Met Ser
            20                  25                  30

Pro Gln Ala Gln Gly Leu Gly Val Asp Gly Ala Cys Arg Pro Cys Ser
        35                  40                  45

Asp Ala Glu Leu Leu Leu Ala Ala Cys Thr Ser Asp Phe Val Ile His
    50                  55                  60

Gly Thr Ile His Gly Val Ala His Asp Thr Glu Leu Gln Glu Ser Val
65                  70                  75                  80

Ile Thr Val Val Val Ala Arg Val Ile Arg Gln Thr Leu Pro Leu Phe
                85                  90                  95

Lys Glu Gly Ser Ser Glu Gly Gln Gly Arg Ala Ser Ile Arg Thr Leu
            100                 105                 110

Leu Arg Cys Gly Val Arg Pro Gly Pro Gly Ser Phe Leu Phe Met Gly
        115                 120                 125

Trp Ser Arg Phe Gly Glu Ala Trp Leu Gly Cys Ala Pro Arg Phe Gln
    130                 135                 140

Glu Phe Ser Arg Val Tyr Ser Ala Ala Leu Thr Thr His Leu Asn Pro
145                 150                 155                 160

Cys Glu Met Ala Leu Asp
                165

<210> SEQ ID NO 11
<211> LENGTH: 2321
<212> TYPE: DNA
<213> ORGANISM: Rattus norvegicus
<220> FEATURE:
<221> NAME/KEY: misc_feature
<222> LOCATION: (17)..(66)
<223> OTHER INFORMATION: n is a, c, g, or t

<400> SEQUENCE: 11
tccccggttg tggggannnn nnnnnnnnnn nnnnnnnnnn nnnnnnnnnn nnnnnnnnnn      60
nnnnnnggca gcagcccgag ccccggcgcg tcccctaacc atgctggtag cggcgcttct     120
ctgcgcgctg tgctgcggcc tcttggctgc gtccgctcga gctggctact ccaggaccg     180 ctgcagctgg aggggcaggt acccaggaga gattttgggg aggattttg ttatttgtgt     240 tttaaattga atcttgggt tggagggctc cctcccactt ggaactgagg aagcgcagac     300
ctcaatgtcc tgttccagag ggtggacgca ggtgttggtg gccgcgggaa aagggttgag     360
cgggctaggg aaatgagggc cacccacctg agaaccaccg tcctgtcccc agcggtttga     420
cccaggaacc tggcagcgtg gggcagctga ccctggattg tactgagggt gctatcgagt     480
ggctgtatcc agctggggcg ctgcgcctga ctctaggcgg ctctgatccg ggcacgcggc     540
```

```
ccagcatcgt ctgtctgcgc ccaacacggc ccttcgctgg tgcccaggtc ttcgctgaac      600
ggatggccgg caacctagag ttgctactgg ccgagggcca aggcctggct ggggggccgct     660 gcatgcgctg gggtcctcgc gagcgccgag cccttttcct gcaggccacg ccacaccggg     720
acatcagccg cagagttgct gccttccaat ttgaactgca cgaggaccaa cgtgcagaaa     780
tgtctcccca ggcccaaggt tttggtgtgg atggtgagtg actagactgg ctggggcgga    840
gctgggtgtc agaaactggc cctctacact ggcctgatcc gaatgggcct tgcctcccca    900
ctgcaccgaa agccctgtag cttgacggag ctactctgg tggagaacac agtggcttcc     960
aggtcatagg gaggtgagtt gagagttctc cctcctttct ctcctcctct tcaaggttcg   1020
gtttaggaaa agagcgggag ggggcagatg ccagagaggc cagccttggg tctctggttt   1080
ctgaagggtt gggggggaagg gttgggctgg ggcagaatca aagccatgg ccgaagctgt   1140 ccagggctcc ctggccttgt ggtgacctcc ttcccctccc cctagcccaa ccaacaaaag   1200
tccagtgtgc ctcttcgtca ccatggagac tgcctgccct gcctcccggc agggcaccag   1260
gcccagtgct ttgctcttct ggaacttgtc tcctgaccct gcaggggaatg gctctctgac   1320 tgctctgcca tagacagaga ccccagaagc agagtccact agaatatccc tggctggacc   1380
tgggaggcag ctctgggagg ttacagaaag ttccccagtg ttggtctgag tttctgagat   1440
gggtgtgcag gaatgtgtcc gaggcactga ggggcccatg agtagtcttc aggcagtgtg   1500
atgctgggag aaggggtttag tcgccagctc ctgtaccttc tcctactgtg gggagctgtg   1560
ggcttgtgct gagagatcac aggcctgcct gatgacctgc cttgcatgct aggtgcctgc   1620
aggccctgca gtgatgccga gctccttctg actgcatgca ccagtgactt tggtgagtgt   1680
ttccgtcttg ggagagctta gggtctgccc cacattccca cgtgcccacc actggccacc   1740
atgtctcttc gtagtgatcc atgggaccat ccatggggtc gtccatgaca tggagctgca   1800
agaatcagtc atcactgtgg tggccactcg tgtcatccgc cagacactgc cactgttcca   1860
ggaagggagc tcgagggcc ggggccaggc ctccgttcgt accttgttgc gctgtggtgt   1920
gcgtcctggc ccaggctcct tcctcttcat gggctggagc cgatttggcg aagcttggct   1980
gggctgcgct ccccgcttcc aagagttcag ccgtgtctat tcagctgctc tcgcggccca   2040
cctcaaccca tgtgaggtgg cactggactg agagacctgg gagcaagccc tggatggatc   2100
ttcctctggg gatggggtgt tgggagggg tgataggagg gtgggtggga agggtgtggc   2160
tcagatggca tcctggtacc cacagtgagg tggtagaata ctaaataacc tggatcacac   2220
cagccactgt agacatggtc ttctgtgaca ggcaggctca ctcagctctg ctcctgcctc   2280
actttaccta ctctccagtc tgctgccctt ctgacccttc t                       2321
```

<210> SEQ ID NO 12
<211> LENGTH: 1026
<212> TYPE: DNA
<213> ORGANISM: Rattus norvegicus
<220> FEATURE:
<221> NAME/KEY: CDS
<222> LOCATION: (1)..(876)

<400> SEQUENCE: 12

```
atg ctg gta gcg gcg ctt ctc tgc gcg ctg tgc tgc ggc ctc ttg gct     48
Met Leu Val Ala Ala Leu Leu Cys Ala Leu Cys Cys Gly Leu Leu Ala
1               5                   10                  15 gcg tcc gct cga gct ggc tac tcc gag gac cgc tgc agc tgg agg ggc     96
Ala Ser Ala Arg Ala Gly Tyr Ser Glu Asp Arg Cys Ser Trp Arg Gly
            20                  25                  30
```

| | | |
|---|---|---|
| agc ggt ttg acc cag gaa cct ggc agc gtg ggg cag ctg acc ctg gat<br>Ser Gly Leu Thr Gln Glu Pro Gly Ser Val Gly Gln Leu Thr Leu Asp<br>     35                      40                       45 | 144 | |
| tgt act gag ggt gct atc gag tgg ctg tat cca gct ggg gcg ctg cgc<br>Cys Thr Glu Gly Ala Ile Glu Trp Leu Tyr Pro Ala Gly Ala Leu Arg<br>50                      55                      60 | 192 | |
| ctg act cta ggc ggc tct gat ccg ggc acg cgg ccc agc atc gtc tgt<br>Leu Thr Leu Gly Gly Ser Asp Pro Gly Thr Arg Pro Ser Ile Val Cys<br>65                      70                      75                      80 | 240 | |
| ctg cgc cca aca cgg ccc ttc gct ggt gcc cag gtc ttc gct gaa cgg<br>Leu Arg Pro Thr Arg Pro Phe Ala Gly Ala Gln Val Phe Ala Glu Arg<br>                  85                      90                      95 | 288 | |
| atg gcc ggc aac cta gag ttg cta ctg gcc gag ggc caa ggc ctg gct<br>Met Ala Gly Asn Leu Glu Leu Leu Leu Ala Glu Gly Gln Gly Leu Ala<br>             100                     105                     110 | 336 | |
| ggg ggc cgc tgc atg cgc tgg ggt cct cgc gag cgc cga gcc ctt ttc<br>Gly Gly Arg Cys Met Arg Trp Gly Pro Arg Glu Arg Arg Ala Leu Phe<br>             115                     120                     125 | 384 | |
| ctg cag gcc acg cca cac cgg gac atc agc cgc aga gtt gct gcc ttc<br>Leu Gln Ala Thr Pro His Arg Asp Ile Ser Arg Arg Val Ala Ala Phe<br>130                     135                     140 | 432 | |
| caa ttt gaa ctg cac gag gac caa cgt gca gaa atg tct ccc cag gcc<br>Gln Phe Glu Leu His Glu Asp Gln Arg Ala Glu Met Ser Pro Gln Ala<br>145                     150                     155                     160 | 480 | |
| caa ggt ttt ggt gtg gat ggt gcc tgc agg ccc tgc agt gat gcc gag<br>Gln Gly Phe Gly Val Asp Gly Ala Cys Arg Pro Cys Ser Asp Ala Glu<br>                           165                     170                     175 | 528 | |
| ctc ctt ctg act gca tgc acc agt gac ttt gtg atc cat ggg acc atc<br>Leu Leu Leu Thr Ala Cys Thr Ser Asp Phe Val Ile His Gly Thr Ile<br>             180                     185                     190 | 576 | |
| cat ggg gtc gtc cat gac atg gag ctg caa gaa tca gtc atc act gtg<br>His Gly Val Val His Asp Met Glu Leu Gln Glu Ser Val Ile Thr Val<br>                 195                     200                     205 | 624 | |
| gtg gcc act cgt gtc atc cgc cag aca ctg cca ctg ttc cag gaa ggg<br>Val Ala Thr Arg Val Ile Arg Gln Thr Leu Pro Leu Phe Gln Glu Gly<br>210                     215                     220 | 672 | |
| agc tcg gag ggc cgg ggc cag gcc tcc gtt cgt acc ttg ttg cgc tgt<br>Ser Ser Glu Gly Arg Gly Gln Ala Ser Val Arg Thr Leu Leu Arg Cys<br>225                     230                     235                     240 | 720 | |
| ggt gtg cgt cct ggc cca ggc tcc ttc ctc ttc atg ggc tgg agc cga<br>Gly Val Arg Pro Gly Pro Gly Ser Phe Leu Phe Met Gly Trp Ser Arg<br>                           245                     250                     255 | 768 | |
| ttt ggc gaa gct tgg ctg ggc tgc gct ccc cgc ttc caa gag ttc agc<br>Phe Gly Glu Ala Trp Leu Gly Cys Ala Pro Arg Phe Gln Glu Phe Ser<br>             260                     265                     270 | 816 | |
| cgt gtc tat tca gct gct ctc gcg gcc cac ctc aac cca tgt gag gtg<br>Arg Val Tyr Ser Ala Ala Leu Ala Ala His Leu Asn Pro Cys Glu Val<br>             275                     280                     285 | 864 | |
| gca ctg gac tga gagacctggg agcaagccct ggatggatct tcctctgggg<br>Ala Leu Asp<br>    290 | 916 | |
| atggggtgtt ggggaggggt gataggaggg tgggtgggaa gggtgtggct cagatggcat | 976 | |
| cctggtaccc acagtgaggt ggtagaatac taaataacct ggatcacacc | 1026 | |

<210> SEQ ID NO 13
<211> LENGTH: 291
<212> TYPE: PRT
<213> ORGANISM: Rattus norvegicus

<400> SEQUENCE: 13

```
Met Leu Val Ala Ala Leu Leu Cys Ala Leu Cys Gly Leu Leu Ala
1               5                   10                  15

Ala Ser Ala Arg Ala Gly Tyr Ser Glu Asp Arg Cys Ser Trp Arg Gly
            20                  25                  30

Ser Gly Leu Thr Gln Glu Pro Gly Ser Val Gly Gln Leu Thr Leu Asp
            35                  40                  45

Cys Thr Glu Gly Ala Ile Glu Trp Leu Tyr Pro Ala Gly Ala Leu Arg
50                  55                  60

Leu Thr Leu Gly Gly Ser Asp Pro Gly Thr Arg Pro Ser Ile Val Cys
65                  70                  75                  80

Leu Arg Pro Thr Arg Pro Phe Ala Gly Ala Gln Val Phe Ala Glu Arg
                85                  90                  95

Met Ala Gly Asn Leu Glu Leu Leu Ala Glu Gly Gln Gly Leu Ala
                100                 105                 110

Gly Gly Arg Cys Met Arg Trp Gly Pro Arg Glu Arg Ala Leu Phe
            115                 120                 125

Leu Gln Ala Thr Pro His Arg Asp Ile Ser Arg Arg Val Ala Ala Phe
130                 135                 140

Gln Phe Glu Leu His Glu Asp Gln Arg Ala Glu Met Ser Pro Gln Ala
145                 150                 155                 160

Gln Gly Phe Gly Val Asp Gly Ala Cys Arg Pro Cys Ser Asp Ala Glu
                165                 170                 175

Leu Leu Leu Thr Ala Cys Thr Ser Asp Phe Val Ile His Gly Thr Ile
                180                 185                 190

His Gly Val Val His Asp Met Glu Leu Gln Ser Val Ile Thr Val
            195                 200                 205

Val Ala Thr Arg Val Ile Arg Gln Thr Leu Pro Leu Phe Gln Glu Gly
210                 215                 220

Ser Ser Glu Gly Arg Gly Gln Ala Ser Val Arg Thr Leu Leu Arg Cys
225                 230                 235                 240

Gly Val Arg Pro Gly Pro Gly Ser Phe Leu Phe Met Gly Trp Ser Arg
                245                 250                 255

Phe Gly Glu Ala Trp Leu Gly Cys Ala Pro Arg Phe Gln Glu Phe Ser
                260                 265                 270

Arg Val Tyr Ser Ala Ala Leu Ala Ala His Leu Asn Pro Cys Glu Val
                275                 280                 285

Ala Leu Asp
    290

<210> SEQ ID NO 14
<211> LENGTH: 275
<212> TYPE: PRT
<213> ORGANISM: Rattus norvegicus
<220> FEATURE:
<221> NAME/KEY: MISC_FEATURE
<222> LOCATION: (1)..(5)
<223> OTHER INFORMATION: Potentially part of signal peptide

<400> SEQUENCE: 14

Ala Ser Ala Arg Ala Gly Tyr Ser Glu Asp Arg Cys Ser Trp Arg Gly
1               5                   10                  15

Ser Gly Leu Thr Gln Glu Pro Gly Ser Val Gly Gln Leu Thr Leu Asp
            20                  25                  30

Cys Thr Glu Gly Ala Ile Glu Trp Leu Tyr Pro Ala Gly Ala Leu Arg
            35                  40                  45
```

```
Leu Thr Leu Gly Gly Ser Asp Pro Gly Thr Arg Pro Ser Ile Val Cys
 50                  55                  60

Leu Arg Pro Thr Arg Pro Phe Ala Gly Ala Gln Val Phe Ala Glu Arg
 65                  70                  75                  80

Met Ala Gly Asn Leu Glu Leu Leu Ala Glu Gly Gln Gly Leu Ala
             85                  90                  95

Gly Gly Arg Cys Met Arg Trp Gly Pro Arg Glu Arg Arg Ala Leu Phe
             100                 105                 110

Leu Gln Ala Thr Pro His Arg Asp Ile Ser Arg Arg Val Ala Ala Phe
             115                 120                 125

Gln Phe Glu Leu His Glu Asp Gln Arg Ala Glu Met Ser Pro Gln Ala
130                 135                 140

Gln Gly Phe Gly Val Asp Gly Ala Cys Arg Pro Cys Ser Asp Ala Glu
145                 150                 155                 160

Leu Leu Leu Thr Ala Cys Thr Ser Asp Phe Val Ile His Gly Thr Ile
                165                 170                 175

His Gly Val Val His Asp Met Glu Leu Gln Glu Ser Val Ile Thr Val
            180                 185                 190

Val Ala Thr Arg Val Ile Arg Gln Thr Leu Pro Leu Phe Gln Glu Gly
            195                 200                 205

Ser Ser Glu Gly Arg Gly Gln Ala Ser Val Arg Thr Leu Leu Arg Cys
210                 215                 220

Gly Val Arg Pro Gly Pro Gly Ser Phe Leu Phe Met Gly Trp Ser Arg
225                 230                 235                 240

Phe Gly Glu Ala Trp Leu Gly Cys Ala Pro Arg Phe Gln Glu Phe Ser
                245                 250                 255

Arg Val Tyr Ser Ala Ala Leu Ala Ala His Leu Asn Pro Cys Glu Val
            260                 265                 270

Ala Leu Asp
275

<210> SEQ ID NO 15
<211> LENGTH: 166
<212> TYPE: PRT
<213> ORGANISM: Rattus norvegicus

<400> SEQUENCE: 15

Ala Leu Phe Leu Gln Ala Thr Pro His Arg Asp Ile Ser Arg Arg Val
 1               5                  10                  15

Ala Ala Phe Gln Phe Glu Leu His Glu Asp Gln Arg Ala Glu Met Ser
                20                  25                  30

Pro Gln Ala Gln Gly Phe Gly Val Asp Gly Ala Cys Arg Pro Cys Ser
             35                  40                  45

Asp Ala Glu Leu Leu Leu Thr Ala Cys Thr Ser Asp Phe Val Ile His
 50                  55                  60

Gly Thr Ile His Gly Val Val His Asp Met Glu Leu Gln Glu Ser Val
 65                  70                  75                  80

Ile Thr Val Val Ala Thr Arg Val Ile Arg Gln Thr Leu Pro Leu Phe
                 85                  90                  95

Gln Glu Gly Ser Ser Glu Gly Arg Gly Gln Ala Ser Val Arg Thr Leu
            100                 105                 110

Leu Arg Cys Gly Val Arg Pro Gly Pro Gly Ser Phe Leu Phe Met Gly
            115                 120                 125

Trp Ser Arg Phe Gly Glu Ala Trp Leu Gly Cys Ala Pro Arg Phe Gln
130                 135                 140
```

```
Glu Phe Ser Arg Val Tyr Ser Ala Ala Leu Ala Ala His Leu Asn Pro
145                 150                 155                 160

Cys Glu Val Ala Leu Asp
                165

<210> SEQ ID NO 16
<211> LENGTH: 480
<212> TYPE: DNA
<213> ORGANISM: Homo sapiens

<400> SEQUENCE: 16
gccctcttcc tgcaggccac gccgcaccag gacatcagcc gccgcgtggc cgccttccgc      60
tttgagctgc gcgaggacgg gcgccccgag ctgccccgc aggcccacgg tctcggcgta     120
gacggtgcct gcaggccctg cagcgacgct gagctgctcc tggccgcatg caccagcgac     180
ttcgtaattc acgggatcat ccatggggtc acccatgacg tggagctgca ggagtctgtc     240
atcactgtgg tggccgcccg tgtcctccgc cagacaccgc cgctgttcca ggcggggcga     300
tccggggacc aggggctgac ctccattcgt accccactgc gctgtggcgt ccacccgggc     360
ccaggcacct cctcttcat gggctggagc cgctttgggg aggccggct gggctgtgcc      420 ccacgattcc aggagttccg ccgtgcctac gaggctgccc gtgctgccca cctccacccc     480

<210> SEQ ID NO 17
<211> LENGTH: 480
<212> TYPE: DNA
<213> ORGANISM: Mus musculus

<400> SEQUENCE: 17 gccctttcc tgcaggccac accacaccgc gacatcagcc gcagagttgc tgccttccgt      60
tttgaactgc acgaggacca acgtgcagaa atgtctcccc aggctcaagg tcttggtgtg     120
gatggtgcct gcaggccctg cagtgatgcc gagctcctcc tggctgcatg caccagtgat     180
tttgtgatcc acgggaccat ccatggggtc gcccatgaca cagagctgca agaatcagtc     240
atcactgtgg tggttgctcg tgtcatccgc cagacactgc cactgttcaa ggaagggagc     300
tcggagggcc aaggccgggc ctccattcgt accttgctgc gctgtggtgt gcgtcctggc     360
ccaggctcct cctcttcat gggctggagc cgatttggcg aagcttggct gggctgtgct      420
ccccgcttcc aagagttcag ccgtgtctat tcagctgctc tcacgaccca tctcaaccca     480

<210> SEQ ID NO 18
<211> LENGTH: 480
<212> TYPE: DNA
<213> ORGANISM: Rattus norvegicus

<400> SEQUENCE: 18 gccctttcc tgcaggccac gccacaccgg gacatcagcc gcagagttgc tgccttccaa      60
tttgaactgc acgaggacca acgtgcagaa atgtctcccc aggcccaagg ttttggtgtg     120
gatggtgcct gcaggccctg cagtgatgcc gagctccttc tgactgcatg caccagtgac     180
tttgtgatcc atgggaccat ccatggggtc gtccatgaca tggagctgca agaatcagtc     240
atcactgtgg tggccactcg tgtcatccgc cagacactgc cactgttcca ggaagggagc     300
tcggagggcc ggggccaggc ctccgttcgt accttgttgc gctgtggtgt gcgtcctggc     360
ccaggctcct cctcttcat gggctggagc cgatttggcg aagcttggct gggctgcgct      420
ccccgcttcc aagagttcag ccgtgtctat tcagctgctc tcgcggccca cctcaaccca     480
```

<210> SEQ ID NO 19
<211> LENGTH: 104
<212> TYPE: PRT
<213> ORGANISM: Homo sapiens

<400> SEQUENCE: 19

Gly Tyr Ser Glu Glu Arg Cys Ser Trp Arg Gly Ser Gly Leu Thr Gln
1               5                   10                  15

Glu Pro Gly Ser Val Gly Gln Leu Ala Leu Ala Cys Ala Glu Gly Ala
            20                  25                  30

Val Glu Trp Leu Tyr Pro Ala Gly Ala Leu Arg Leu Thr Leu Gly Gly
        35                  40                  45

Pro Asp Pro Arg Ala Arg Pro Gly Ile Ala Cys Leu Arg Pro Val Arg
50                  55                  60

Pro Phe Ala Gly Ala Gln Val Phe Ala Glu Arg Ala Gly Gly Ala Leu
65                  70                  75                  80

Glu Leu Leu Leu Ala Glu Gly Pro Gly Pro Ala Gly Gly Arg Cys Val
                85                  90                  95

Arg Trp Gly Pro Arg Glu Arg Arg
            100

<210> SEQ ID NO 20
<211> LENGTH: 104
<212> TYPE: PRT
<213> ORGANISM: Mus musculus

<400> SEQUENCE: 20

Gly Tyr Ser Glu Asp Arg Cys Ser Trp Arg Gly Ser Gly Leu Thr Gln
1               5                   10                  15

Glu Pro Gly Ser Val Gly Gln Leu Thr Leu Asp Cys Thr Glu Gly Ala
            20                  25                  30

Ile Glu Trp Leu Tyr Pro Ala Gly Ala Leu Arg Leu Thr Leu Gly Gly
        35                  40                  45

Pro Asp Pro Gly Thr Arg Pro Ser Ile Val Cys Leu Arg Pro Glu Arg
50                  55                  60

Pro Phe Ala Gly Ala Gln Val Phe Ala Glu Arg Met Thr Gly Asn Leu
65                  70                  75                  80

Glu Leu Leu Leu Ala Glu Gly Pro Asp Leu Ala Gly Gly Arg Cys Met
                85                  90                  95

Arg Trp Gly Pro Arg Glu Arg Arg
            100

<210> SEQ ID NO 21
<211> LENGTH: 109
<212> TYPE: PRT
<213> ORGANISM: Rattus norvegicus
<220> FEATURE:
<221> NAME/KEY: MISC_FEATURE
<222> LOCATION: (1)..(5)
<223> OTHER INFORMATION: Potentially part of signal peptide

<400> SEQUENCE: 21

Ala Ser Ala Arg Ala Gly Tyr Ser Glu Asp Arg Cys Ser Trp Arg Gly
1               5                   10                  15

Ser Gly Leu Thr Gln Glu Pro Gly Ser Val Gly Gln Leu Thr Leu Asp
            20                  25                  30

Cys Thr Glu Gly Ala Ile Glu Trp Leu Tyr Pro Ala Gly Ala Leu Arg
        35                  40                  45

-continued

```
Leu Thr Leu Gly Gly Ser Asp Pro Gly Thr Arg Pro Ser Ile Val Cys
 50                  55                  60

Leu Arg Pro Thr Arg Pro Phe Ala Gly Ala Gln Val Phe Ala Glu Arg
 65                  70                  75                  80

Met Ala Gly Asn Leu Glu Leu Leu Ala Glu Gly Gln Gly Leu Ala
                 85                  90                  95

Gly Gly Arg Cys Met Arg Trp Gly Pro Arg Glu Arg Arg
            100                 105
```

<210> SEQ ID NO 22
<211> LENGTH: 97
<212> TYPE: PRT
<213> ORGANISM: Homo sapiens

<400> SEQUENCE: 22

```
Gly Tyr Ser Glu Glu Arg Cys Ser Trp Arg Gly Ser Gly Leu Thr Gln
 1               5                  10                  15

Glu Pro Gly Ser Val Gly Gln Leu Ala Leu Ala Cys Ala Glu Gly Ala
                 20                  25                  30

Val Glu Trp Leu Tyr Pro Ala Gly Ala Leu Arg Leu Thr Leu Gly Gly
             35                  40                  45

Pro Asp Pro Arg Ala Arg Pro Gly Ile Ala Cys Leu Arg Pro Val Arg
 50                  55                  60

Pro Phe Ala Gly Ala Gln Val Phe Ala Glu Arg Ala Gly Gly Ala Leu
 65                  70                  75                  80

Glu Leu Leu Leu Ala Glu Gly Pro Gly Pro Ala Gly Gly Arg Cys Val
                 85                  90                  95

Arg
```

<210> SEQ ID NO 23
<211> LENGTH: 97
<212> TYPE: PRT
<213> ORGANISM: Mus musculus

<400> SEQUENCE: 23

```
Gly Tyr Ser Glu Asp Arg Cys Ser Trp Arg Gly Ser Gly Leu Thr Gln
 1               5                  10                  15

Glu Pro Gly Ser Val Gly Gln Leu Thr Leu Asp Cys Thr Glu Gly Ala
                 20                  25                  30

Ile Glu Trp Leu Tyr Pro Ala Gly Ala Leu Arg Leu Thr Leu Gly Gly
             35                  40                  45

Pro Asp Pro Gly Thr Arg Pro Ser Ile Val Cys Leu Arg Pro Glu Arg
 50                  55                  60

Pro Phe Ala Gly Ala Gln Val Phe Ala Glu Arg Met Thr Gly Asn Leu
 65                  70                  75                  80

Glu Leu Leu Leu Ala Glu Gly Pro Asp Leu Ala Gly Gly Arg Cys Met
                 85                  90                  95

Arg
```

<210> SEQ ID NO 24
<211> LENGTH: 102
<212> TYPE: PRT
<213> ORGANISM: Rattus norvegicus
<220> FEATURE:
<221> NAME/KEY: MISC_FEATURE
<222> LOCATION: (1)..(5)
<223> OTHER INFORMATION: Potentially part of signal peptide

<400> SEQUENCE: 24

```
Ala Ser Ala Arg Ala Gly Tyr Ser Glu Asp Arg Cys Ser Trp Arg Gly
1               5                   10                  15

Ser Gly Leu Thr Gln Glu Pro Gly Ser Val Gly Gln Leu Thr Leu Asp
            20                  25                  30

Cys Thr Glu Gly Ala Ile Glu Trp Leu Tyr Pro Ala Gly Ala Leu Arg
        35                  40                  45

Leu Thr Leu Gly Gly Ser Asp Pro Gly Thr Arg Pro Ser Ile Val Cys
50                  55                  60

Leu Arg Pro Thr Arg Pro Phe Ala Gly Ala Gln Val Phe Ala Glu Arg
65              70                  75                  80

Met Ala Gly Asn Leu Glu Leu Leu Leu Ala Glu Gly Gln Gly Leu Ala
                85                  90                  95

Gly Gly Arg Cys Met Arg
            100
```

```
<210> SEQ ID NO 25
<211> LENGTH: 1363
<212> TYPE: DNA
<213> ORGANISM: Mus musculus
<220> FEATURE:
<221> NAME/KEY: CDS
<222> LOCATION: (84)..(959)

<400> SEQUENCE: 25
```

```
gggcagccgc gccgcgggct gctcgcgctg cggccccgac cctcccgggg cagcagtccg      60
aggccccggc gcgtccccta acc atg ctg gta gcc acg ctt ctt tgc gcg ctc     113
                         Met Leu Val Ala Thr Leu Leu Cys Ala Leu
                          1               5                  10 tgt tgc ggc ctc ctg gcc gcg tcc gct cac gct ggc tac tcg gaa gac       161
Cys Cys Gly Leu Leu Ala Ala Ser Ala His Ala Gly Tyr Ser Glu Asp
                15                  20                  25 cgc tgc agc tgg agg ggc agc ggt ttg acc cag gag cct ggc agc gtg       209
Arg Cys Ser Trp Arg Gly Ser Gly Leu Thr Gln Glu Pro Gly Ser Val
            30                  35                  40 ggg cag ctg acc ctg gac tgt act gag ggc gct atc gag tgg ctg tac       257
Gly Gln Leu Thr Leu Asp Cys Thr Glu Gly Ala Ile Glu Trp Leu Tyr
        45                  50                  55 cca gct ggg gcg ctg cgc ctg acc ctg ggc ggc ccc gat ccg ggc aca       305
Pro Ala Gly Ala Leu Arg Leu Thr Leu Gly Gly Pro Asp Pro Gly Thr
    60                  65                  70 cgg ccc agc atc gtc tgt ctg cgc cca gag cgg ccc ttc gct ggt gcc       353
Arg Pro Ser Ile Val Cys Leu Arg Pro Glu Arg Pro Phe Ala Gly Ala
75                  80                  85                  90 cag gtc ttc gct gaa cgt atg acc ggc aat cta gag ttg cta ctg gcc       401
Gln Val Phe Ala Glu Arg Met Thr Gly Asn Leu Glu Leu Leu Leu Ala
                95                  100                 105 gag ggc ccg gac ctg gct ggg ggc cgc tgc atg cgc tgg ggt ccc cgc       449
Glu Gly Pro Asp Leu Ala Gly Gly Arg Cys Met Arg Trp Gly Pro Arg
            110                 115                 120 gag cgc cga gcc ctt ttc ctg cag gcc aca cca cac cgc gac atc agc       497
Glu Arg Arg Ala Leu Phe Leu Gln Ala Thr Pro His Arg Asp Ile Ser
        125                 130                 135 cgc aga gtt gct gcc ttc cgt ttt gaa ctg cac gag gac caa cgt gca       545
Arg Arg Val Ala Ala Phe Arg Phe Glu Leu His Glu Asp Gln Arg Ala
    140                 145                 150 gaa atg tct ccc cag gct caa ggt ctt ggt gtg gat ggt gcc tgc agg       593
Glu Met Ser Pro Gln Ala Gln Gly Leu Gly Val Asp Gly Ala Cys Arg
155                 160                 165                 170
```

| | | | | | | | | | | | | | | | | |
|---|---|---|---|---|---|---|---|---|---|---|---|---|---|---|---|---|
| ccc | tgc | agt | gat | gcc | gag | ctc | ctc | ctg | gct | gca | tgc | acc | agt | gat | ttt | 641 |
| Pro | Cys | Ser | Asp | Ala | Glu | Leu | Leu | Leu | Ala | Ala | Cys | Thr | Ser | Asp | Phe | |
| | | | | 175 | | | | 180 | | | | | 185 | | | |
| gtg | atc | cac | ggg | acc | atc | cat | ggg | gtc | gcc | cat | gac | aca | gag | ctg | caa | 689 |
| Val | Ile | His | Gly | Thr | Ile | His | Gly | Val | Ala | His | Asp | Thr | Glu | Leu | Gln | |
| | | | 190 | | | | | 195 | | | | | 200 | | | |
| gaa | tca | gtc | atc | act | gtg | gtg | gtt | gct | cgt | gtc | atc | cgc | cag | aca | ctg | 737 |
| Glu | Ser | Val | Ile | Thr | Val | Val | Val | Ala | Arg | Val | Ile | Arg | Gln | Thr | Leu | |
| | | | 205 | | | | | 210 | | | | | 215 | | | |
| cca | ctg | ttc | aag | gaa | ggg | agc | tcg | gag | ggc | caa | ggc | cgg | gcc | tcc | att | 785 |
| Pro | Leu | Phe | Lys | Glu | Gly | Ser | Ser | Glu | Gly | Gln | Gly | Arg | Ala | Ser | Ile | |
| | | | 220 | | | | | 225 | | | | | 230 | | | |
| cgt | acc | ttg | ctg | cgc | tgt | ggt | gtg | cgt | cct | ggc | cca | ggc | tcc | ttc | ctc | 833 |
| Arg | Thr | Leu | Leu | Arg | Cys | Gly | Val | Arg | Pro | Gly | Pro | Gly | Ser | Phe | Leu | |
| 235 | | | | | 240 | | | | | 245 | | | | | 250 | |
| ttc | atg | ggc | tgg | agc | cga | ttt | ggc | gaa | gct | tgg | ctg | ggc | tgt | gct | ccc | 881 |
| Phe | Met | Gly | Trp | Ser | Arg | Phe | Gly | Glu | Ala | Trp | Leu | Gly | Cys | Ala | Pro | |
| | | | | 255 | | | | | 260 | | | | | 265 | | |
| cgc | ttc | caa | gag | ttc | agc | cgt | gtc | tat | tca | gct | gct | ctc | acg | acc | cat | 929 |
| Arg | Phe | Gln | Glu | Phe | Ser | Arg | Val | Tyr | Ser | Ala | Ala | Leu | Thr | Thr | His | |
| | | | | 270 | | | | | 275 | | | | | 280 | | |
| ctc | aac | cca | tgt | gag | atg | gca | ctg | gac | tga | gagacctggg | | agcaagccct | | | | 979 |
| Leu | Asn | Pro | Cys | Glu | Met | Ala | Leu | Asp | | | | | | | | |
| | | 285 | | | | | 290 | | | | | | | | | |

```
ggatggacct tcttctggag atgggggtgtt ggggagggtg atgggagggt gggtgagaag      1039
ggtgtggctc ggatggcatc ctggtaccca cagtgagctg gtagaatact aagtaatctg      1099
gaccatacca gccactgtag tcatggtctt ctgtggcagg cagcataccc agctctgtgc      1159
ctgcctcact ttgtctactc tccagtctgc tgcccttcta acccttctta gcctgctgac      1219
cagtgagctc atgttttcct cgaattccag ggtgctgctg gggttcagag caaccgtgcc      1279
gtagtttgga agacttgagc taattgtttt tttttttgttt gttttttttgt ttgtttaaag    1339 gtggcctggg gggggcggca aaca                                             1363
```

<210> SEQ ID NO 26
<211> LENGTH: 291
<212> TYPE: PRT
<213> ORGANISM: Mus musculus

<400> SEQUENCE: 26

Met Leu Val Ala Thr Leu Leu Cys Ala Leu Cys Cys Gly Leu Leu Ala
1               5                   10                  15

Ala Ser Ala His Ala Gly Tyr Ser Glu Asp Arg Cys Ser Trp Arg Gly
            20                  25                  30

Ser Gly Leu Thr Gln Glu Pro Gly Ser Val Gly Gln Leu Thr Leu Asp
        35                  40                  45

Cys Thr Glu Gly Ala Ile Glu Trp Leu Tyr Pro Ala Gly Ala Leu Arg
    50                  55                  60

Leu Thr Leu Gly Gly Pro Asp Pro Gly Thr Arg Pro Ser Ile Val Cys
65                  70                  75                  80

Leu Arg Pro Glu Arg Pro Phe Ala Gly Ala Gln Val Phe Ala Glu Arg
                85                  90                  95

Met Thr Gly Asn Leu Glu Leu Leu Ala Glu Gly Pro Asp Leu Ala
            100                 105                 110

Gly Gly Arg Cys Met Arg Trp Gly Pro Arg Glu Arg Arg Ala Leu Phe
        115                 120                 125

Leu Gln Ala Thr Pro His Arg Asp Ile Ser Arg Arg Val Ala Ala Phe

```
                130             135             140
Arg Phe Glu Leu His Glu Asp Gln Arg Ala Glu Met Ser Pro Gln Ala
145                 150                 155                 160

Gln Gly Leu Gly Val Asp Gly Ala Cys Arg Pro Cys Ser Asp Ala Glu
                165                 170                 175

Leu Leu Leu Ala Ala Cys Thr Ser Asp Phe Val Ile His Gly Thr Ile
            180                 185                 190

His Gly Val Ala His Asp Thr Glu Leu Gln Glu Ser Val Ile Thr Val
        195                 200                 205

Val Val Ala Arg Val Ile Arg Gln Thr Leu Pro Leu Phe Lys Glu Gly
    210                 215                 220

Ser Ser Glu Gly Gln Gly Arg Ala Ser Ile Arg Thr Leu Leu Arg Cys
225                 230                 235                 240

Gly Val Arg Pro Gly Pro Gly Ser Phe Leu Phe Met Gly Trp Ser Arg
                245                 250                 255

Phe Gly Glu Ala Trp Leu Gly Cys Ala Pro Arg Phe Gln Glu Phe Ser
            260                 265                 270

Arg Val Tyr Ser Ala Ala Leu Thr Thr His Leu Asn Pro Cys Glu Met
        275                 280                 285

Ala Leu Asp
    290

<210> SEQ ID NO 27
<211> LENGTH: 4
<212> TYPE: PRT
<213> ORGANISM: homo sapiens
<220> FEATURE:
<221> NAME/KEY: misc_feature
<223> OTHER INFORMATION: Conserved strong group of NsG33

<400> SEQUENCE: 27

Asn Glu Gln Lys
1

<210> SEQ ID NO 28
<211> LENGTH: 4
<212> TYPE: PRT
<213> ORGANISM: homo sapiens
<220> FEATURE:
<221> NAME/KEY: misc_feature
<223> OTHER INFORMATION: Conserved strong group of NsG33

<400> SEQUENCE: 28

Asn His Gln Lys
1

<210> SEQ ID NO 29
<211> LENGTH: 4
<212> TYPE: PRT
<213> ORGANISM: homo sapiens
<220> FEATURE:
<221> NAME/KEY: misc_feature
<223> OTHER INFORMATION: Conserved strong group of NsG33

<400> SEQUENCE: 29

Asn Asp Glu Gln
1

<210> SEQ ID NO 30
<211> LENGTH: 4
<212> TYPE: PRT
<213> ORGANISM: homo sapiens
```

```
<220> FEATURE:
<221> NAME/KEY: misc_feature
<223> OTHER INFORMATION: Conserved strong group of NsG33

<400> SEQUENCE: 30

Gln His Arg Lys
1

<210> SEQ ID NO 31
<211> LENGTH: 4
<212> TYPE: PRT
<213> ORGANISM: homo sapiens
<220> FEATURE:
<221> NAME/KEY: misc_feature
<223> OTHER INFORMATION: Conserved strong group of NsG33

<400> SEQUENCE: 31

Met Ile Leu Val
1

<210> SEQ ID NO 32
<211> LENGTH: 4
<212> TYPE: PRT
<213> ORGANISM: homo sapiens
<220> FEATURE:
<221> NAME/KEY: misc_feature
<223> OTHER INFORMATION: Conserved strong group of NsG33

<400> SEQUENCE: 32

Met Ile Leu Phe
1

<210> SEQ ID NO 33
<211> LENGTH: 4
<212> TYPE: PRT
<213> ORGANISM: homo sapiens
<220> FEATURE:
<221> NAME/KEY: misc_feature
<223> OTHER INFORMATION: Conserved weak group of NsG33

<400> SEQUENCE: 33

Ser Thr Asn Lys
1

<210> SEQ ID NO 34
<211> LENGTH: 4
<212> TYPE: PRT
<213> ORGANISM: homo sapiens
<220> FEATURE:
<221> NAME/KEY: misc_feature
<223> OTHER INFORMATION: Conserved weak group of NsG33

<400> SEQUENCE: 34

Ser Thr Pro Ala
1

<210> SEQ ID NO 35
<211> LENGTH: 4
<212> TYPE: PRT
<213> ORGANISM: homo sapiens
<220> FEATURE:
<221> NAME/KEY: misc_feature
<223> OTHER INFORMATION: Conserved weak group of NsG33

<400> SEQUENCE: 35

Ser Gly Asn Asp
1
```

```
<210> SEQ ID NO 36
<211> LENGTH: 6
<212> TYPE: PRT
<213> ORGANISM: homo sapiens
<220> FEATURE:
<221> NAME/KEY: misc_feature
<223> OTHER INFORMATION: Conserved weak group of NsG33

<400> SEQUENCE: 36

Ser Asn Asp Glu Gln Lys
1               5

<210> SEQ ID NO 37
<211> LENGTH: 6
<212> TYPE: PRT
<213> ORGANISM: homo sapiens
<220> FEATURE:
<221> NAME/KEY: misc_feature
<223> OTHER INFORMATION: Conserved weak group of NsG33

<400> SEQUENCE: 37

Asn Asp Glu Gln His Lys
1               5

<210> SEQ ID NO 38
<211> LENGTH: 6
<212> TYPE: PRT
<213> ORGANISM: homo sapiens
<220> FEATURE:
<221> NAME/KEY: misc_feature
<223> OTHER INFORMATION: Conserved weak group of NsG33

<400> SEQUENCE: 38

Asn Glu Gln His Arg Lys
1               5

<210> SEQ ID NO 39
<211> LENGTH: 4
<212> TYPE: PRT
<213> ORGANISM: homo sapiens
<220> FEATURE:
<221> NAME/KEY: misc_feature
<223> OTHER INFORMATION: Conserved weak group of NsG33

<400> SEQUENCE: 39

Val Leu Ile Met
1

<210> SEQ ID NO 40
<211> LENGTH: 311
<212> TYPE: PRT
<213> ORGANISM: Homo sapiens

<400> SEQUENCE: 40

Met Arg Gly Ala Ala Arg Ala Ala Trp Gly Arg Ala Gly Gln Pro Trp
1               5                   10                  15

Pro Arg Pro Pro Ala Pro Gly Pro Pro Pro Pro Leu Pro Leu Leu
            20                  25                  30

Leu Leu Leu Leu Ala Gly Leu Leu Gly Gly Ala Gly Ala Gln Tyr Ser
        35                  40                  45

Ser Asp Arg Cys Ser Trp Lys Gly Ser Gly Leu Thr His Glu Ala His
    50                  55                  60

Arg Lys Glu Val Glu Gln Val Tyr Leu Arg Cys Ala Ala Gly Ala Val
65                  70                  75                  80
```

```
Glu Trp Met Tyr Pro Thr Gly Ala Leu Ile Val Asn Leu Arg Pro Asn
             85                  90                  95

Thr Phe Ser Pro Ala Arg His Leu Thr Val Cys Ile Arg Ser Phe Thr
           100                 105                 110

Asp Ser Ser Gly Ala Asn Ile Tyr Leu Glu Lys Thr Gly Glu Leu Arg
           115                 120                 125

Leu Leu Val Pro Asp Gly Asp Gly Arg Pro Gly Arg Val Gln Cys Phe
           130                 135                 140

Gly Leu Glu Gln Gly Gly Leu Phe Val Glu Ala Thr Pro Gln Gln Asp
145                 150                 155                 160

Ile Gly Arg Arg Thr Thr Gly Phe Gln Tyr Glu Leu Val Arg Arg His
                165                 170                 175

Arg Ala Ser Asp Leu His Glu Leu Ser Ala Pro Cys Arg Pro Cys Ser
           180                 185                 190

Asp Thr Glu Val Leu Leu Ala Val Cys Thr Ser Asp Phe Ala Val Arg
           195                 200                 205

Gly Ser Ile Gln Gln Val Thr His Glu Pro Glu Arg Gln Asp Ser Ala
           210                 215                 220

Ile His Leu Arg Val Ser Arg Leu Tyr Arg Gln Lys Ser Arg Val Phe
225                 230                 235                 240

Glu Pro Val Pro Glu Gly Asp Gly His Trp Gln Gly Arg Val Arg Thr
                245                 250                 255

Leu Leu Glu Cys Gly Val Arg Pro Gly His Gly Asp Phe Leu Phe Thr
           260                 265                 270

Gly His Met His Phe Gly Glu Ala Arg Leu Gly Cys Ala Pro Arg Phe
           275                 280                 285

Lys Asp Phe Gln Arg Met Tyr Arg Asp Ala Gln Glu Arg Gly Leu Asn
           290                 295                 300

Pro Cys Glu Val Gly Thr Asp
305                 310

<210> SEQ ID NO 41
<211> LENGTH: 5
<212> TYPE: PRT
<213> ORGANISM: homo sapiens
<220> FEATURE:
<221> NAME/KEY: misc_feature
<223> OTHER INFORMATION: NsG33 cleavage sequence motif

<400> SEQUENCE: 41

Ala Arg Ala Gly Tyr
1               5

<210> SEQ ID NO 42
<211> LENGTH: 9
<212> TYPE: PRT
<213> ORGANISM: homo sapiens
<220> FEATURE:
<221> NAME/KEY: misc_feature
<223> OTHER INFORMATION: NsG33 cleavage sequence motif

<400> SEQUENCE: 42

Trp Gly Pro Arg Glu Arg Arg Ala Leu
1               5

<210> SEQ ID NO 43
<211> LENGTH: 8
<212> TYPE: PRT
<213> ORGANISM: homo sapiens
<220> FEATURE:
```

```
<221> NAME/KEY: misc_feature
<223> OTHER INFORMATION: NsG33 cleavage sequence motif

<400> SEQUENCE: 43

Gly Gly Arg Cys Val Arg Trp Gly
1               5

<210> SEQ ID NO 44
<211> LENGTH: 8
<212> TYPE: PRT
<213> ORGANISM: Rattus norvegicus
<220> FEATURE:
<221> NAME/KEY: misc_feature
<223> OTHER INFORMATION: N-terminal of cleaved NsG33

<400> SEQUENCE: 44

Gly Tyr Ser Glu Asp Arg Cys Ser
1               5

<210> SEQ ID NO 45
<211> LENGTH: 10
<212> TYPE: PRT
<213> ORGANISM: Rattus norvegicus
<220> FEATURE:
<221> NAME/KEY: misc_feature
<223> OTHER INFORMATION: N-terminal of NsG33

<400> SEQUENCE: 45

Ala Ser Ala Arg Ala Gly Tyr Ser Glu Asp
1               5                   10

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000
```

```
<210> SEQ ID NO 52
<400> SEQUENCE: 52

000

<210> SEQ ID NO 53
<400> SEQUENCE: 53

000

<210> SEQ ID NO 54
<400> SEQUENCE: 54

000

<210> SEQ ID NO 55
<400> SEQUENCE: 55

000

<210> SEQ ID NO 56
<400> SEQUENCE: 56

000

<210> SEQ ID NO 57
<400> SEQUENCE: 57

000

<210> SEQ ID NO 58
<211> LENGTH: 4
<212> TYPE: PRT
<213> ORGANISM: homo sapiens
<220> FEATURE:
<221> NAME/KEY: misc_feature
<223> OTHER INFORMATION: Conserved strong group of NsG33

<400> SEQUENCE: 58

Asn Glu Asp Gln
1

<210> SEQ ID NO 59
<211> LENGTH: 5
<212> TYPE: PRT
<213> ORGANISM: homo sapiens
<220> FEATURE:
<221> NAME/KEY: misc_feature
<223> OTHER INFORMATION: Conserved weak group of NsG33

<400> SEQUENCE: 59

Asn Glu Gln His Lys
1               5

<210> SEQ ID NO 60
<211> LENGTH: 270
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
```

```
<223> OTHER INFORMATION: Xaa is any naturally occurring amino acid
<220> FEATURE:
<221> NAME/KEY: MISC_FEATURE
<222> LOCATION: (25)..(25)
<223> OTHER INFORMATION: Xaa is any naturally occurring amino acid
<220> FEATURE:
<221> NAME/KEY: MISC_FEATURE
<222> LOCATION: (27)..(27)
<223> OTHER INFORMATION: Xaa is any naturally occurring amino acid
<220> FEATURE:
<221> NAME/KEY: MISC_FEATURE
<222> LOCATION: (29)..(29)
<223> OTHER INFORMATION: Xaa is any naturally occurring amino acid
<220> FEATURE:
<221> NAME/KEY: MISC_FEATURE
<222> LOCATION: (33)..(33)
<223> OTHER INFORMATION: Xaa is any naturally occurring amino acid
<220> FEATURE:
<221> NAME/KEY: MISC_FEATURE
<222> LOCATION: (49)..(49)
<223> OTHER INFORMATION: Xaa is any naturally occurring amino acid
<220> FEATURE:
<221> NAME/KEY: MISC_FEATURE
<222> LOCATION: (52)..(53)
<223> OTHER INFORMATION: Xaa is any naturally occurring amino acid
<220> FEATURE:
<221> NAME/KEY: MISC_FEATURE
<222> LOCATION: (56)..(56)
<223> OTHER INFORMATION: Xaa is any naturally occurring amino acid
<220> FEATURE:
<221> NAME/KEY: MISC_FEATURE
<222> LOCATION: (58)..(58)
<223> OTHER INFORMATION: Xaa is any naturally occurring amino acid
<220> FEATURE:
<221> NAME/KEY: MISC_FEATURE
<222> LOCATION: (63)..(63)
<223> OTHER INFORMATION: Xaa is any naturally occurring amino acid
<220> FEATURE:
<221> NAME/KEY: MISC_FEATURE
<222> LOCATION: (76)..(77)
<223> OTHER INFORMATION: Xaa is any naturally occurring amino acid
<220> FEATURE:
<221> NAME/KEY: MISC_FEATURE
<222> LOCATION: (79)..(79)
<223> OTHER INFORMATION: Xaa is any naturally occurring amino acid
<220> FEATURE:
<221> NAME/KEY: MISC_FEATURE
<222> LOCATION: (88)..(90)
<223> OTHER INFORMATION: Xaa is any naturally occurring amino acid
<220> FEATURE:
<221> NAME/KEY: MISC_FEATURE
<222> LOCATION: (96)..(96)
<223> OTHER INFORMATION: Xaa is any naturally occurring amino acid
<220> FEATURE:
<221> NAME/KEY: MISC_FEATURE
<222> LOCATION: (114)..(114)
<223> OTHER INFORMATION: Xaa is any naturally occurring amino acid
<220> FEATURE:
<221> NAME/KEY: MISC_FEATURE
<222> LOCATION: (124)..(124)
<223> OTHER INFORMATION: Xaa is any naturally occurring amino acid
<220> FEATURE:
<221> NAME/KEY: MISC_FEATURE
<222> LOCATION: (128)..(128)
<223> OTHER INFORMATION: Xaa is any naturally occurring amino acid
<220> FEATURE:
<221> NAME/KEY: MISC_FEATURE
<222> LOCATION: (131)..(131)
<223> OTHER INFORMATION: Xaa is any naturally occurring amino acid
<220> FEATURE:
<221> NAME/KEY: MISC_FEATURE
<222> LOCATION: (133)..(133)
<223> OTHER INFORMATION: Xaa is any naturally occurring amino acid
<220> FEATURE:
<221> NAME/KEY: MISC_FEATURE
<222> LOCATION: (135)..(136)
<223> OTHER INFORMATION: Xaa is any naturally occurring amino acid
<220> FEATURE:
<221> NAME/KEY: MISC_FEATURE
```

```
<222> LOCATION: (140)..(140)
<223> OTHER INFORMATION: Xaa is any naturally occurring amino acid
<220> FEATURE:
<221> NAME/KEY: MISC_FEATURE
<222> LOCATION: (142)..(142)
<223> OTHER INFORMATION: Xaa is any naturally occurring amino acid
<220> FEATURE:
<221> NAME/KEY: MISC_FEATURE
<222> LOCATION: (159)..(159)
<223> OTHER INFORMATION: Xaa is any naturally occurring amino acid
<220> FEATURE:
<221> NAME/KEY: MISC_FEATURE
<222> LOCATION: (170)..(170)
<223> OTHER INFORMATION: Xaa is any naturally occurring amino acid
<220> FEATURE:
<221> NAME/KEY: MISC_FEATURE
<222> LOCATION: (175)..(175)
<223> OTHER INFORMATION: Xaa is any naturally occurring amino acid
<220> FEATURE:
<221> NAME/KEY: MISC_FEATURE
<222> LOCATION: (178)..(178)
<223> OTHER INFORMATION: Xaa is any naturally occurring amino acid
<220> FEATURE:
<221> NAME/KEY: MISC_FEATURE
<222> LOCATION: (189)..(190)
<223> OTHER INFORMATION: Xaa is any naturally occurring amino acid
<220> FEATURE:
<221> NAME/KEY: MISC_FEATURE
<222> LOCATION: (193)..(193)
<223> OTHER INFORMATION: Xaa is any naturally occurring amino acid
<220> FEATURE:
<221> NAME/KEY: MISC_FEATURE
<222> LOCATION: (197)..(197)
<223> OTHER INFORMATION: Xaa is any naturally occurring amino acid
<220> FEATURE:
<221> NAME/KEY: MISC_FEATURE
<222> LOCATION: (201)..(202)
<223> OTHER INFORMATION: Xaa is any naturally occurring amino acid
<220> FEATURE:
<221> NAME/KEY: MISC_FEATURE
<222> LOCATION: (204)..(204)
<223> OTHER INFORMATION: Xaa is any naturally occurring amino acid
<220> FEATURE:
<221> NAME/KEY: MISC_FEATURE
<222> LOCATION: (206)..(208)
<223> OTHER INFORMATION: Xaa is any naturally occurring amino acid
<220> FEATURE:
<221> NAME/KEY: MISC_FEATURE
<222> LOCATION: (210)..(211)
<223> OTHER INFORMATION: Xaa is any naturally occurring amino acid
<220> FEATURE:
<221> NAME/KEY: MISC_FEATURE
<222> LOCATION: (213)..(213)
<223> OTHER INFORMATION: Xaa is any naturally occurring amino acid
<220> FEATURE:
<221> NAME/KEY: MISC_FEATURE
<222> LOCATION: (216)..(216)
<223> OTHER INFORMATION: Xaa is any naturally occurring amino acid
<220> FEATURE:
<221> NAME/KEY: MISC_FEATURE
<222> LOCATION: (222)..(222)
<223> OTHER INFORMATION: Xaa is any naturally occurring amino acid
<220> FEATURE:
<221> NAME/KEY: MISC_FEATURE
<222> LOCATION: (227)..(227)
<223> OTHER INFORMATION: Xaa is any naturally occurring amino acid
<220> FEATURE:
<221> NAME/KEY: MISC_FEATURE
<222> LOCATION: (240)..(240)
<223> OTHER INFORMATION: Xaa is any naturally occurring amino acid
<220> FEATURE:
<221> NAME/KEY: MISC_FEATURE
<222> LOCATION: (251)..(251)
<223> OTHER INFORMATION: Xaa is any naturally occurring amino acid
<220> FEATURE:
<221> NAME/KEY: MISC_FEATURE
<222> LOCATION: (253)..(253)
<223> OTHER INFORMATION: Xaa is any naturally occurring amino acid
<220> FEATURE:
```

```
<221> NAME/KEY: MISC_FEATURE
<222> LOCATION: (255)..(255)
<223> OTHER INFORMATION: Xaa is any naturally occurring amino acid
<220> FEATURE:
<221> NAME/KEY: MISC_FEATURE
<222> LOCATION: (258)..(260)
<223> OTHER INFORMATION: Xaa is any naturally occurring amino acid
<220> FEATURE:
<221> NAME/KEY: MISC_FEATURE
<222> LOCATION: (263)..(263)
<223> OTHER INFORMATION: Xaa is any naturally occurring amino acid
<220> FEATURE:
<221> NAME/KEY: MISC_FEATURE
<222> LOCATION: (267)..(267)
<223> OTHER INFORMATION: Xaa is any naturally occurring amino acid
<220> FEATURE:
<221> NAME/KEY: MISC_FEATURE
<222> LOCATION: (270)..(270)
<223> OTHER INFORMATION: Xaa is any naturally occurring amino acid

<400> SEQUENCE: 60

Gly Tyr Ser Glu Xaa Arg Cys Ser Trp Arg Gly Ser Gly Leu Thr Gln
1               5                   10                  15

Glu Pro Gly Ser Val Gly Gln Leu Xaa Leu Xaa Cys Xaa Glu Gly Ala
            20                  25                  30

Xaa Glu Trp Leu Tyr Pro Ala Gly Ala Leu Arg Leu Thr Leu Gly Gly
        35                  40                  45

Xaa Asp Pro Xaa Xaa Arg Pro Xaa Ile Xaa Cys Leu Arg Pro Xaa Arg
    50                  55                  60

Pro Phe Ala Gly Ala Gln Val Phe Ala Glu Arg Xaa Xaa Gly Xaa Leu
65                  70                  75                  80

Glu Leu Leu Leu Ala Glu Gly Xaa Xaa Xaa Ala Gly Gly Arg Cys Xaa
                85                  90                  95

Arg Trp Gly Pro Arg Glu Arg Arg Ala Leu Phe Leu Gln Ala Thr Pro
            100                 105                 110

His Xaa Asp Ile Ser Arg Arg Val Ala Ala Phe Xaa Phe Glu Leu Xaa
        115                 120                 125

Glu Asp Xaa Arg Xaa Glu Xaa Xaa Pro Gln Ala Xaa Gly Xaa Gly Val
    130                 135                 140

Asp Gly Ala Cys Arg Pro Cys Ser Asp Ala Glu Leu Leu Leu Xaa Ala
145                 150                 155                 160

Cys Thr Ser Asp Phe Val Ile His Gly Xaa Ile His Gly Val Xaa His
                165                 170                 175

Asp Xaa Glu Leu Gln Glu Ser Val Ile Thr Val Val Xaa Xaa Arg Val
        180                 185                 190

Xaa Arg Gln Thr Xaa Pro Leu Phe Xaa Xaa Gly Xaa Ser Xaa Xaa Xaa
    195                 200                 205

Gly Xaa Xaa Ser Xaa Arg Thr Xaa Leu Arg Cys Gly Val Xaa Pro Gly
    210                 215                 220

Pro Gly Xaa Phe Leu Phe Met Gly Trp Ser Arg Phe Gly Glu Ala Xaa
225                 230                 235                 240

Leu Gly Cys Ala Pro Arg Phe Gln Glu Phe Xaa Arg Xaa Tyr Xaa Ala
                245                 250                 255

Ala Xaa Xaa Xaa His Leu Xaa Pro Cys Glu Xaa Ala Leu Xaa
    260                 265                 270
```

THERAPEUTIC USE OF A GROWTH FACTOR, NSG33

RELATED APPLICATIONS

This application is a national stage application, filed under 35 U.S.C. §371, of PCT/EP2005/051431, filed on Mar. 30, 2005, which claims priority to Danish Patent Application No. PA 2004 00510, filed on Mar. 30, 2004; to U.S. Ser. No. 60/575,086, filed on May 28, 2004; and to Danish Patent Application No. PA 2004 00843, filed on May 28, 2004. Each of these applications is herein incorporated by reference in its entirety.

TECHNICAL FIELD

The present invention relates to the field of therapeutic use of proteins, genes and cells, in particular to the therapy based on the biological function of a secreted therapeutic protein, NsG33, in particular for the treatment of disorders of the nervous system and for the treatment immunological disorders. NsG33 is a nerve survival and growth factor with neuroprotective and/or neurogenesis effects. The invention also relates to bioactive NsG33 polypeptide fragments and the corresponding encoding DNA sequences.

BACKGROUND ART

Extracellular proteins play important roles in, among other things, the formation, differentiation and maintenance of multicellular organisms. The fate of many individual cells, e.g., growth including proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Disorders such as Parkinson's disease, Alzheimer's disease, Huntington's disease, multiple and amyotrophic lateral sclerosis, stroke, schizophrenia, epilepsy and peripheral neuropathy and associated pain affect millions of people. It is the loss of normal neuronal function, which produces the behavioral and physical deficits which are characteristic of each of the different neurological disorders. In addition to chronic and acute neurodegenerative disorders, the aging process, physical trauma to the nervous system, and metabolic disorders may result in the loss, dysfunction, or degeneration of neural cells accompanied by the associated behavioral and physical deficits. Many of these diseases are today incurable, highly debilitating, and traditional drug therapies often fail. There is thus a great medical need for new therapeutic proteins that are disease modifying and not only for symptomatic use.

Several secreted factors with expression in the nervous system or associated target areas have important therapeutic uses in various neurological indications associated with reduction or loss of neuronal functions. E.g. NGF is a candidate for treatment of Alzheimer's disease, Neublastin (Artemin) a candidate for treatment of peripheral neuropathy, and GDNF is a candidate for treatment of Parkinson's Disease.

SUMMARY OF THE INVENTION

In a first aspect the invention relates to an isolated polypeptide for medical use, said polypeptide comprising an amino acid sequence selected from the group consisting of:
a) the amino acid sequence selected from the group consisting of SEQ ID No. 3, 4, 5, 8, 9, 10, 13, 14, 15, 19, 20, 21, 22, 23, and 24;
b) a sequence variant of the amino acid sequence selected from the group consisting of SEQ ID No. 3, 4, 5, 8, 9, 10, 13, 14, 15, 19, 20, 21, 22, 23, and 24, wherein the variant has at least 70% sequence identity to said SEQ ID No.; and
c) a biologically active fragment of at least 50 contiguous amino acids of any of a) through b).

The present inventors have found that NsG33 is a secreted protein with growth factor characteristics, which is expressed at high levels and selectively in the nervous system and the eye, and especially in substantia nigra, the putamen and spinal cord, as well as in the mesencephalon of the developing human embryo. In addition, the present inventors have found that NsG33 is capable of protecting a neuronal cell line from apoptotic cell death (Example 6). Apoptotic cell death contributes to neuronal cell loss in the adult nervous system causing various neurological disorders like ischemic stroke, neurodegenerative diseases or brain traumata (Becker and Bonni, Prog Neurobiol. 2004 January; 72(1):1-25).

NsG33 has also shown neuroprotective effects in two assays based on generation of neurons and astrocytes from a human neural progenitor cell line and from a primary culture of rat striatal cells. Therefore, the present inventors have contemplated the use of NsG33 in the treatment of disorders of the central nervous system, in particular in the treatment of Parkinson's Disease, Huntington's disease, and disorders of the spinal cord, such as ALS. Based on the neuroprotective activity and on the expression in the cerebellum, the dorsal root ganglion and the retina, NsG33 is also contemplated for use in the treatment of peripheral neuropathies and associated pain, as well as cerebellar disorders and retinopathies.

Other therapeutically relevant secreted growth factors are expressed in the nervous system or subregions thereof including but not limited to GDNF, NGF, Neurturin, BDNF, NT4/5, NT3, Neublastin (Artemin).

Based on sequence identity to a protein disclosed in WO 93/22437, NsG33 is contemplated for use in the treatment of immunological disorders.

The therapeutic effect of NsG33 may be mediated through an effect on growth, survival, regeneration, regain or improvement of function, and/or on differentiation of targeted cells. The present inventors have shown that NsG33 is capable of protecting a neuronal cell type against apoptotic cell death (Example 6, FIG. 9). The present inventors have also shown that a human neural progenitor cell line and a primary rat striatal culture both generate a higher percentage of neurons when exposed to NsG33 than under control conditions (Example 14 and 15). The latter effect may be caused by improved survival of neurons, by increased differentiation of neurons and/or by proliferation of neuronal precursors.

Based on these biological assays, the present invention relates to a method of preventing apoptosis in a mammalian neuronal cell, said method comprising exposing said neuronal cell to a polypeptide of the present invention. The invention also relates to a method of enhancing survival of a mammalian neuronal cell, said method comprising exposing said neuronal cell to a polypeptide of the present invention. The invention additionally relates to a method of generating a neuron, said method comprising exposing a neuronal precursor cell or a neuronal stem cell to a polypeptide of the present invention. Preferably, said mammalian neuronal cell and/or mammalian neuronal precursor or neuronal stem cell is a human cell.

In a further aspect the invention relates to an isolated nucleic acid molecule for medical use comprising a nucleic acid sequence encoding a polypeptide, or the complementary sequence of the encoding sequence, said polypeptide comprising an amino acid sequence selected from the group consisting of:
a) the amino acid sequence selected from the group consisting of SEQ ID No. 3, 4, 5, 8, 9, 10, 13, 14, 15, 19, 20, 21, 22, 23, and 24;
b) a sequence variant of the amino acid sequence selected from the group consisting of SEQ ID No. 3, 4, 5, 8, 9, 10, 13, 14, 15, 19, 20, 21, 22, 23, and 24, wherein the variant has at least 70% sequence identity to said SEQ ID No.; and
c) a biologically active fragment of at least 50 contiguous amino acids of any of a) through b).

In a further aspect the invention relates to an isolated nucleic acid molecule for medical use, wherein the nucleic acid molecule comprises a nucleotide sequence selected from the group consisting of
a) the nucleotide sequence selected from the group consisting of SEQ ID No. 1, 2, 6, 7, 11, 12, 16, 17, and 18;
b) a nucleotide sequence having at least 50% sequence identity to a nucleotide sequence selected from the group consisting of SEQ ID No. 1, 2, 6, 7, 11, 12, 16, 17, and 18;
c) a nucleic acid sequence of at least 150 contiguous nucleotides of a sequence selected from the group consisting of SEQ ID No. 1, 2, 6, 7, 11, 12, 16, 17, and 18;
c) the complement of a nucleic acid capable of hybridising with nucleic acid having the sequence selected from the group consisting of SEQ ID No. 1, 2, 6, 7, 11, 12, 16, 17, and 18 under conditions of high stringency; and
d) the nucleic acid sequence of the complement of any of the above.

In a further aspect the invention relates to an expression vector comprising a nucleic acid molecule of the invention.

In a still further aspect the invention relates to an isolated host cell comprising an expression vector according to the invention. In particular the invention relates to host cells useful for cell based therapy, either naked cell based therapy or encapsulated cell therapy.

In a further aspect the invention relates to a packaging cell line capable of producing an infective virus particle, said virus particle comprising a Retroviridae derived genome comprising a 5' retroviral LTR, a tRNA binding site, a packaging signal, a promoter operably linked to a polynucleotide sequence encoding a polypeptide of the invention, an origin of second strand DNA synthesis, and a 3' retroviral LTR.

In a further aspect the invention relates to an implantable biocompatible cell device, the device comprising:
i) a semipermeable membrane permitting the diffusion of a protein of the invention; and
ii) a composition of cells according to the invention, or a composition of packaging cells according to the invention.

In a further aspect the invention relates to a pharmaceutical composition comprising
i) a polypeptide of the invention; or
ii) an isolated nucleic acid sequence of the invention; or
iii) an expression vector of the invention; or
iv) a composition of host cells according to the invention; or
v) a packaging cell line according to the invention; or
vi) an implantable biocompatible cell device according to the invention; and
a pharmaceutically acceptable carrier.

In a further aspect the invention relates to the use of
i) a polypeptide of the invention; or
ii) an isolated nucleic acid sequence of the invention; or
iii) an expression vector of the invention; or
iv) a composition of host cells according to the invention; or
v) a packaging cell line according to the invention; or
vi) an implantable biocompatible capsule according to the invention.
for the manufacture of a medicament.

In a further aspect the invention relates to a method of treatment of a pathological condition in a subject, comprising administering to a subject in need thereof a therapeutically effective amount of:
i) a polypeptide of the invention; or
ii) an isolated nucleic acid sequence of the invention; or
iii) an expression vector of the invention; or
iv) a composition of host cells according to the invention; or
v) a packaging cell line according to the invention; or
vi) an implantable biocompatible capsule according to the invention.

In a further aspect the invention relates to the use of
i) a polypeptide of the invention; or
ii) an isolated nucleic acid sequence of the invention; or
iii) an expression vector of the invention; or
iv) a composition of host cells according to the invention; or
v) a packaging cell line according to the invention;
as a growth factor in mammalian cell culture.

In one aspect the invention relates to an antibody capable of binding to a polypeptide of the invention.

In a further aspect the invention relates to an immunoconjugate comprising the antibody of the invention and a conjugate selected from the group consisting of: a cytotoxic agent such as a chemotherapeutic agent, a toxin, or a radioactive isotope; a member of a specific binding pair, such as avidin or streptavidin or an antigen; an enzyme capable of producing a detectable product.

In a further aspect the invention relates to an isolated polypeptide selected from the group consisting of $AA_{128}$-$AA_{293}$ of SEQ ID No 3, $AA_{121}$-$AA_{293}$ of SEQ ID No 3, $AA_{129}$-$AA_{294}$ of SEQ ID No 8, $AA_{122}$-$AA_{294}$ of SEQ ID No 8, $AA_{126}$-$AA_{291}$ of SEQ ID No 13, $AA_{119}$-$AA_{291}$ of SEQ ID No 13, and variant of said polypeptides, wherein any amino acid specified in the chosen sequence is changed to a different amino acid, provided that no more than 15 of the amino acid residues in the sequence are so changed. These isolated polypeptides constitute C-terminal peptides of NsG33. Preferably any changed amino acids are selected from those designated as unconserved, weakly conserved or strongly conserved in FIG. 3a.

In a further aspect the invention relates to specific truncated forms of NsG33. In one aspect these are selected from the group consisting of:
1) $AA_{30}$-$AA_{288}$ of SEQ ID No 3, and polypeptides having from one to five extra amino acids from the native sequence in one or both ends, up to $AA_{25}$-$AA_{293}$ of SEQ ID No 3;
2) $AA_{28}$-$AA_{286}$ of SEQ ID No 13 and polypeptides having from one to five extra amino acids from the native sequence in one or both ends, up to $AA_{23}$-$AA_{291}$ of SEQ ID No 13;

3) AA$_{31}$-AA$_{289}$ of SEQ ID No 8 and polypeptides having from one to five extra amino acids from the native sequence in one or both ends, up to AA$_{26}$-AA$_{294}$ of SEQ ID No 8; and
4) variants of said polypeptides, wherein any amino acid specified in the chosen sequence is changed to a different amino acid, provided that no more than 20 of the amino acid residues in the sequence are so changed.

These truncated forms of NsG33 constitute a bioactive core sequence from the first to the last conserved cysteine.

In a further aspect the invention relates to specific truncated forms of NsG33. In one aspect these are selected from the group consisting of:
1) AA$_{171}$-AA$_{288}$ of SEQ ID No 3, and polypeptides having from one to five extra amino acids from the native sequence in one or both ends, up to AA$_{165}$-AA$_{288}$ of SEQ ID No 3;
2) AA$_{169}$-AA$_{286}$ of SEQ ID No 13 and polypeptides having from one to five extra amino acids from the native sequence in one or both ends, up to AA$_{164}$-AA$_{291}$ of SEQ ID No 13;
3) AA$_{172}$-AA$_{289}$ of SEQ ID No 8 and polypeptides having from one to five extra amino acids from the native sequence in one or both ends, i.e. up to AA$_{167}$-AA$_{294}$ of SEQ ID No 8;
4) variants of said polypeptides, wherein any amino acid specified in the chosen sequence is changed to a different amino acid, provided that no more than 10 of the amino acid residues in the sequence are so changed.

These truncated forms constitute a bioactive core sequence of the C-terminal NsG33 peptides from the first to the last conserved cysteine in the C-terminal peptides.

In a further aspect the invention relates to specific truncated forms of NsG33. In one aspect these are selected from the group consisting of:
1) AA$_{30}$-AA$_{118}$ of SEQ ID No 3, and polypeptides having from one to five extra amino acids from the native sequence in one or both ends, up to AA$_{25}$-AA$_{123}$ of SEQ ID No 3;
2) AA$_{28}$-AA$_{116}$ of SEQ ID No 13 and polypeptides having from one to five extra amino acids from the native sequence in one or both ends, up to AA$_{23}$-AA$_{121}$ of SEQ ID No 13;
3) AA$_{31}$-AA$_{119}$ of SEQ ID No 8 and polypeptides having from one to five extra amino acids from the native sequence in one or both ends, up to AA$_{26}$-AA$_{124}$ of SEQ ID No 8; and
4) variants of said polypeptides, wherein any amino acid specified in the chosen sequence is changed to a different amino acid, provided that no more than 10 of the amino acid residues in the sequence are so changed.

These truncated forms constitute a bioactive core sequence of the N-terminal NsG33 peptides from the first to the last conserved cysteine in the N-terminal peptides.

The invention also relates to nucleic acids coding for said C-terminal, N-terminal and truncated NsG33 as well as vectors comprising the nucleic acids coding for these, cells capable of producing these, and methods of preparing said C-terminal, N-terminal and truncated NsG33.

BRIEF DESCRIPTION OF THE DRAWINGS

FIG. 1. Prediction of presence and location of signal peptide in human NsG33.

FIG. 2: Output from the ProtFun2.1 protein function prediction server on full length human NsG33 (SEQ ID No 3), human N-terminal peptide (SEQ ID No 19) and human C-terminal peptide (SEQ ID No 5). For explanations, refer to example 2.

FIG. 3a: Clustal W (1.82) multiple sequence alignment of human (SEQ ID NO: 3), partial mouse (SEQ ID NO: 8) and rat NsG33 (SEQ ID NO: 13). The signal sequences are shown in bold. A putative furin cleavage site has been underlined.

FIG. 3b: Clustal W (1.82) multiple sequence alignment of human (SEQ ID NO:3), mouse (SEQ ID NO: 26) and rat NsG33 (SEQ ID NO: 13). The predicted signal sequences are shown in bold.

\* indicates positions which have a single, fully conserved residue.

: indicates that one of the following 'strong' groups is fully conserved:
   -STA, NEQK (SEQ ID NO: 27), NHQK (SEQ ID NO: 28), NDEQ (SEQ ID NO: 29), QHRK (SEQ ID NO: 30), MILV (SEQ ID NO: 31), MILF (SEQ ID NO: 32), HY, FYW.

. indicates that one of the following 'weaker' groups is fully conserved:
   -CSA, ATV, SAG, STNK (SEQ ID NO: 33), STPA (SEQ ID NO: 34), SGND (SEQ ID NO: 35), SNDEQK (SEQ ID NO: 36), NDEQHK (SEQ ID NO: 37), NEQHRK (SEQ ID NO: 38), VLIM (SEQ ID NO: 39), HFY.

FIG. 4: Real Time PCR on NsG33. For details see Example 5.

FIG. 4, upper panel shows the relative expression of NsG33 (relative to tissue with the lowest expression) assuming same amounts of cDNA were synthesized from equal amounts of total RNA used for the cDNA step.

FIG. 4, lower panel shows the relative expression of NsG33 normalised to $\beta_2$-microglobulin (relative to tissue with the lowest normalized expression). Results should be interpreted with caution as $\beta_2$-microglobulin expression levels vary between some tissues.

FIG. 5: Align0 alignment of full length human NsG33 polypeptide (SEQ ID NO: 3) against full-length human polypeptide (Innog.) (SEQ ID NO: 40) from WO 93/22437 (Innogenetics SA). Scoring matrix BLOSUM50, gap penalties: −12/−2. The ten conserved cysteines are shown in bold with asterisks above or below the aligned sequences.

Figure 6:
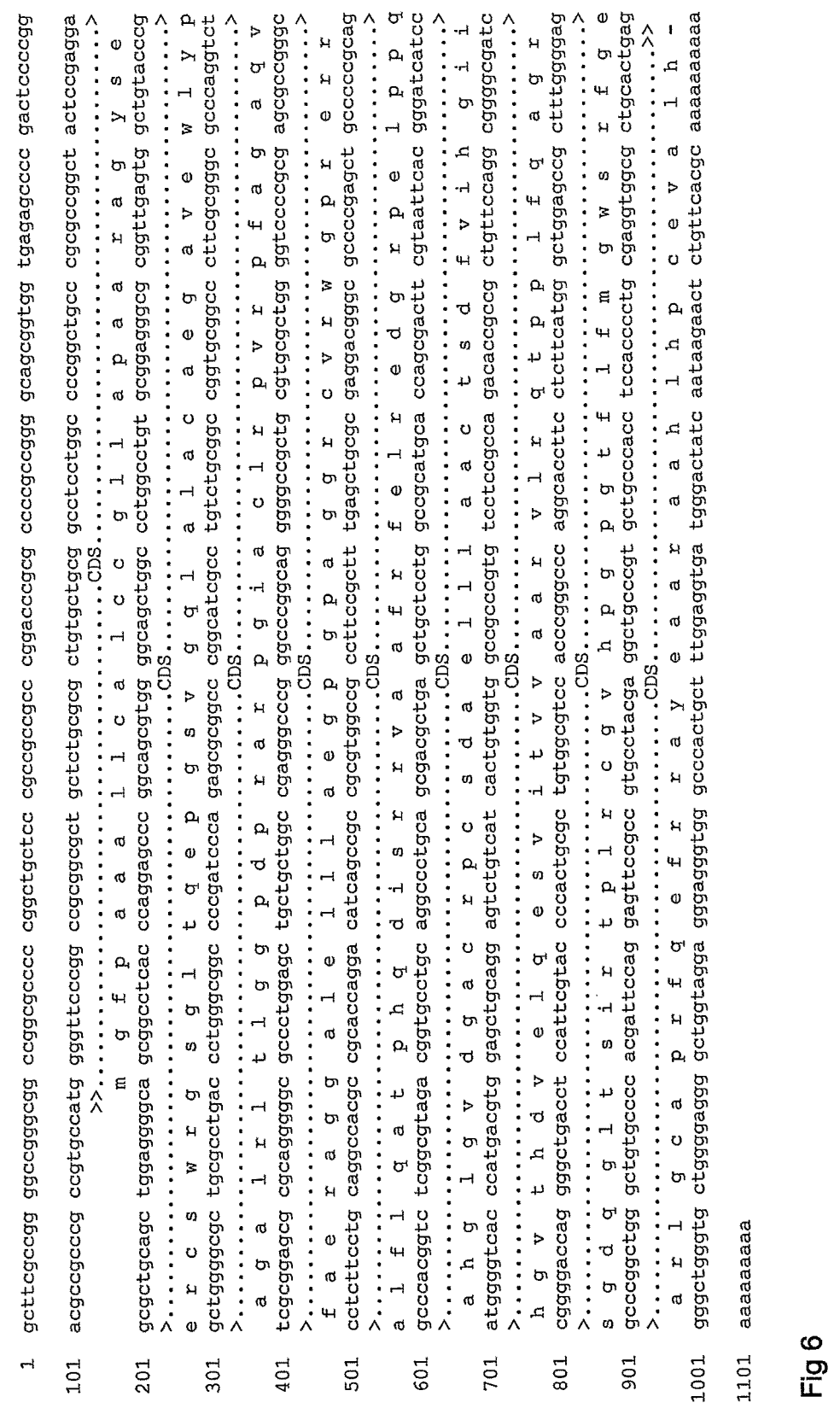

FIG. 6: Human NsG33 cDNA (SEQ ID NO: 2) and encoded prepro-NsG33 (SEQ ID NO:

FIG. 7a: Partial mouse NsG33 cDNA (SEQ ID NO: 7) and encoded partial pre-pro-NsG33 (SEQ ID NO: 8)

Figure 7B:
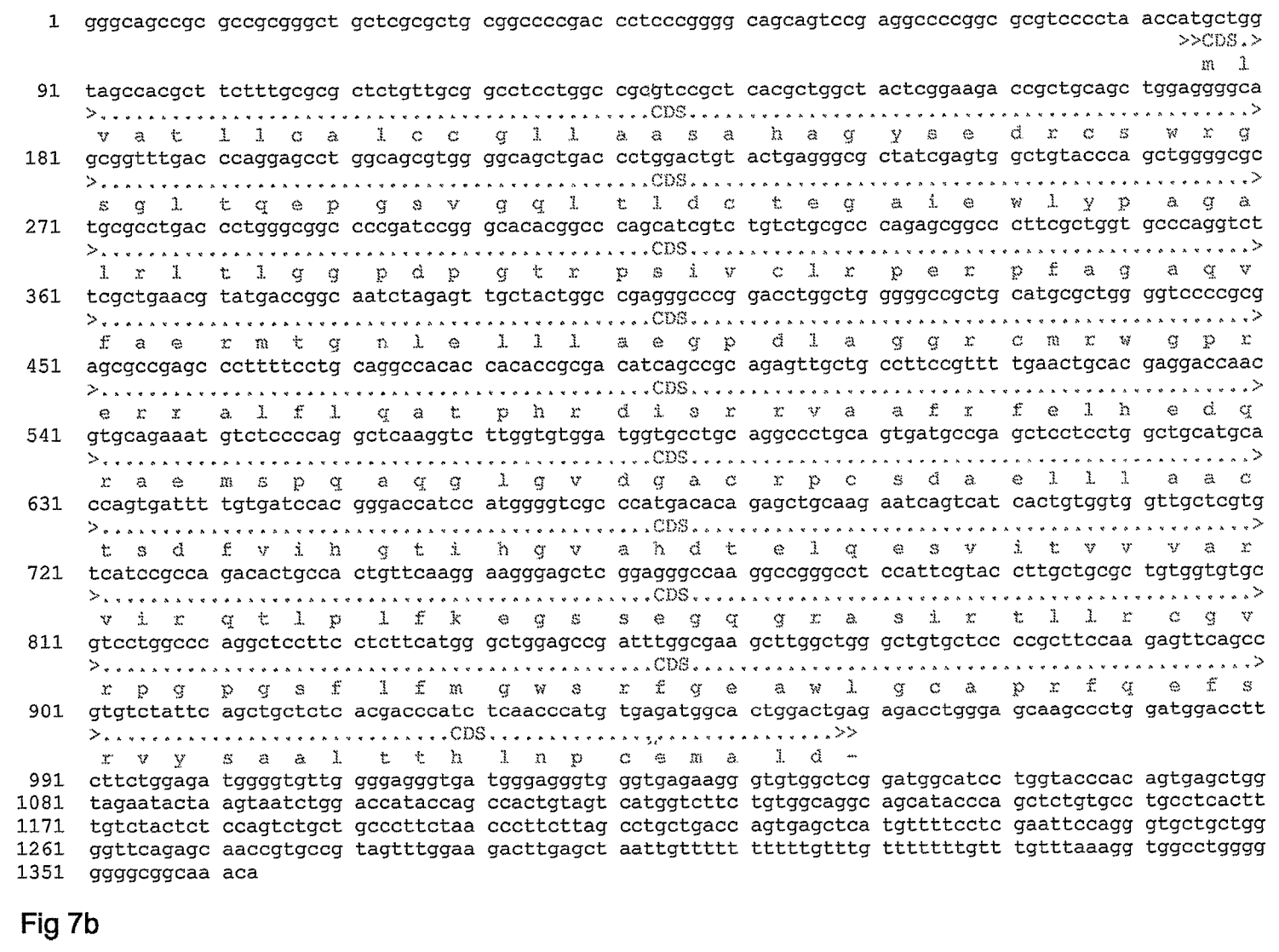

FIG. 7b: Full length mouse NsG33 cDNA (SEQ ID NO: 25) and encoded pre-pro-NsG33 (SEQ ID NO: 26)

FIG. 8: Rat NsG33 cDNA (SEQ ID NO: 12) and encoded pre-pro-NsG33 (SEQ ID NO: 13).

Figure 9:
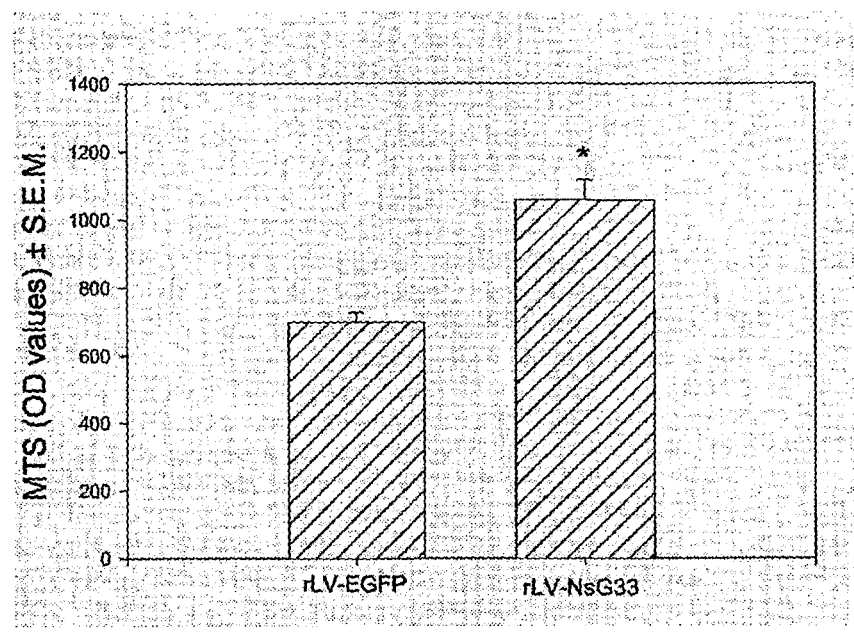

FIG. 9: Effect of NsG33 on PC12 survival in serum-free medium. For additional details see Example 6. Cells were seeded in collagen-coated 48-well plates, $2\times10^4$ cells/well in growth medium. The following day, cells were transduced by incubation overnight with $10^5$ transducing units virus/well (MOI=5) in the presence of 5 μg/ml polybrene. After transduction, medium was changed to serum-free DMEM (Invitrogen) and cell survival was then assayed after four days using the MTS assay. Data shown are means±SEM (n=6) from a representative experiment, and \* indicates a significant difference from cells transduced with cDNA for EGFP (P<0.05, one way ANOVA, Dunnetts Method). LV-EGFP: lentivirus EGFP transduced PC12 cells. LV-NsG33: PC12 cells transduced with human full length NsG33.

Figure 10A:
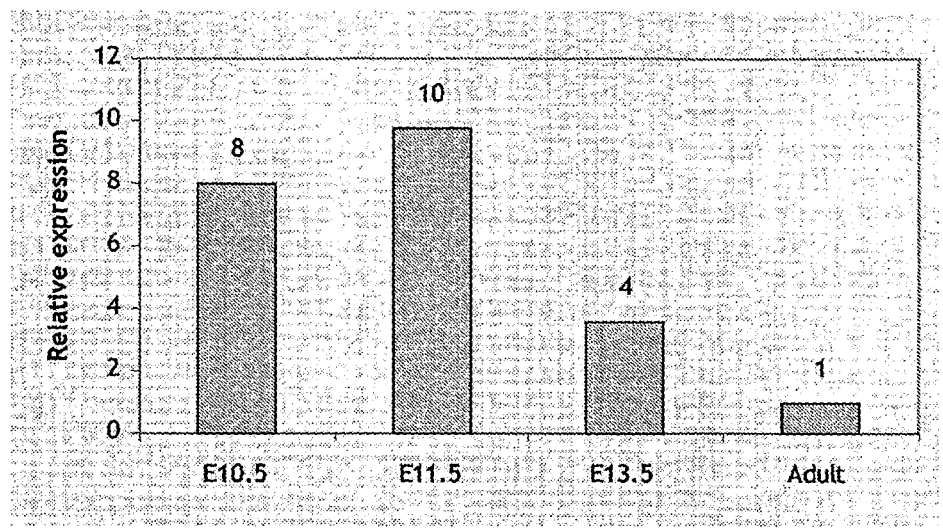

FIG. 10A shows the relative expression of mNsG33 as measured by quantitative RT-PCR (relative to tissue with the lowest expression) normalised to GAPDH in the developing spinal cord at the embryonic ages E10.5, E11.5, and E13.5 (10.5, 11.5 and 13.5 days post conception respectively) and in the adult Spinal Cord. Details are described in Example 13.

Figure 10B:
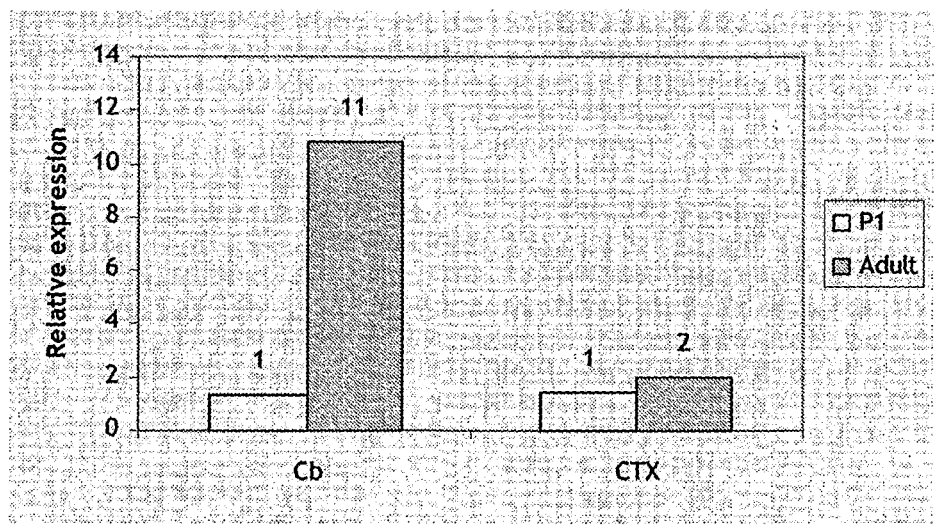

FIG. 10B shows the relative expression of mNsG33 in two regions of the mouse brain (CTX=cortex, Cb=Cerebellum) at two developmental ages (P1=one day postnatal and adult). The expression is measured by quantitative RT-PCR normalised to the expression of mGAPDH relative to tissue with the lowest normalised expression. Details are described in Example 13.

Figure 11A:
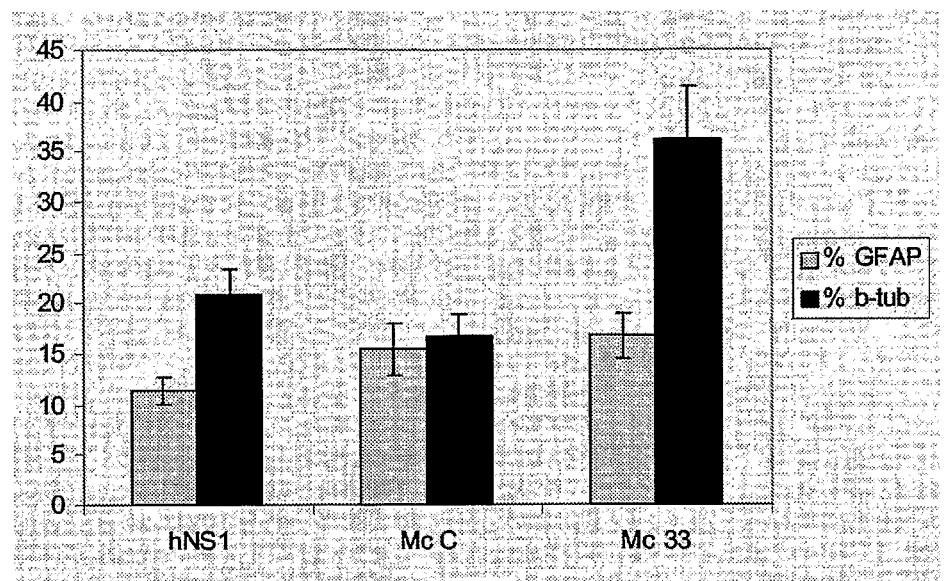

FIG. 11A shows the average percentages of GFAP-positive glial cells (grey bars) and the $\beta_3$-III-tubulin positive neurons (black bars) in differentiating hNS1 cultures receiving unconditioned (hNS1) serum-free medium, conditioned media from control ARPE-19 cells (Mc C) or from NsG33-transduced ARPE-19 cultures (Mc 33). Further details are described in Example 14.

Figure 11B:
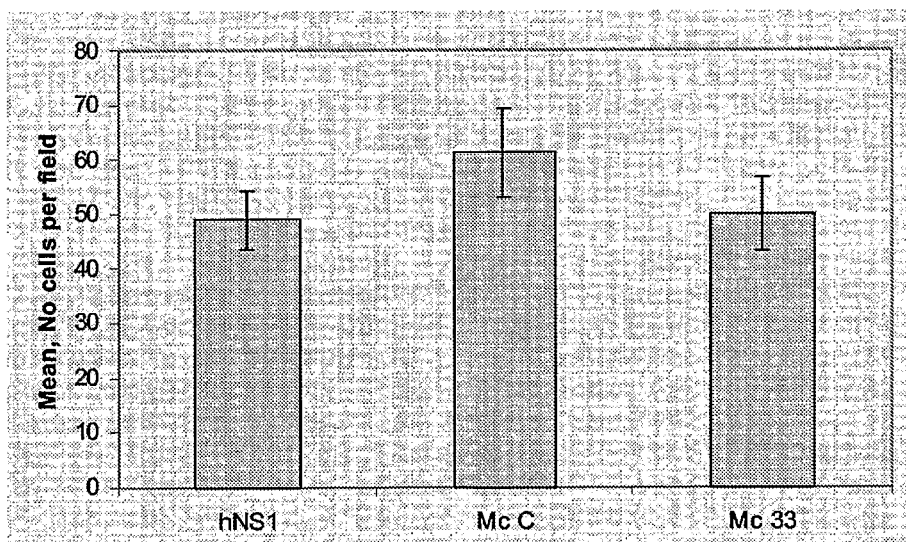

FIG. 11B shows the total number of cells per field as determined by counting Hoechst stained nuclei using a 40× objective in differentiating hNS1 cultures receiving unconditioned (hNS1) serum-free medium, conditioned media from control ARPE-19 cells (Mc C) or from NsG33-transduced ARPE-19 cultures (Mc 33). Further details are described in Example 14.

Figure 12:
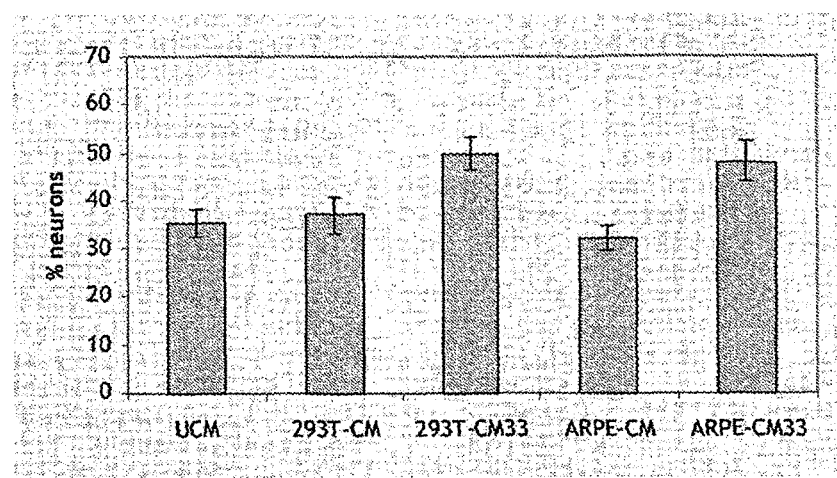

FIG. 12 shows the average percentages of β-III-tubulin positive neurons in rat striatal cultures receiving unconditioned (UCM) serum-free medium, diluted conditioned media from MOCK transfected HEK293T or ARPE-19 cells (293T-CM and ARPE-CM, respectively) or from the parallel NsG33-transfected cultures (293T-CM33 and ARPE-CM33, respectively) at DIV2. Further details are described in Example 15.

DEFINITIONS

NsG33, as used herein, refers to polypeptides having the amino acid sequences of substantially purified NsG33 obtained from any species, particularly mammalian, including chimpanzee, bovine, ovine, porcine, murine, equine, and preferably human, from any source whether natural, synthetic, semi-synthetic, or recombinant. The term also refers to biologically active fragments of NsG33 obtained from any of these species, as well as to biologically active sequence variants of these and to proteins subject to post-translational modifications.

Growth factor characteristics as used herein define sequence-related features similar to those of classical growth factors, which are secreted proteins acting on a target cell through a receptor to cause one or more of the following responses in the target cell: growth including proliferation, differentiation, survival, regeneration, migration, regain of function, improvement of function.

An "allele" or "allelic sequence", as used herein, is an alternative form of the gene encoding NsG33. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

A "deletion", as used herein, refers to a change in the amino acid or nucleotide sequence and results in the absence of one or more amino acid residues or nucleotides.

An "insertion" or "addition", as used herein, refers to a change in an amino acid or nucleotide sequence resulting in the addition of one or more amino acid residues or nucleotides, respectively, as compared to the naturally occurring molecule.

The terms "specific binding" or "specifically binding", as used herein, refers to the high affinity interaction between a protein or peptide and a binding molecule such as an antibody and a receptor or fragments thereof. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Sequence Identity":

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the BLASTN and BLASTP programs of Altschul, et al. (1990) J. Mol. Biol. 215:403-410.

In order to characterize the identity, subject sequences are aligned so that the highest order homology (match) is obtained. Based on these general principles the "percent identity" of two amino acid sequences may be determined using the BLASTP algorithm [Tatiana A. Tatusova, Thomas L. Madden: Blast 2 sequences—a new tool for comparing protein and nucleotide sequences; *FEMS Microbiol. Lett.* 1999 174 247-250], which is available from the National Center for Biotechnology Information (NCBI) web site (http://www.ncbi.nim.nih.gov), and using the default settings suggested here (i.e. Matrix=Blosum62; Open gap=11; Extension gap=1; Penalties gap x_dropoff=50; Expect=10; Word size=3; Filter on). The BLAST algorithm performs a two-step operation by first aligning two sequences based on the settings and then determining the % sequence identity in a range of overlap between two aligned sequences. In addition to % sequence identity, BLASTP also determines the % sequence similarity based on the settings.

In order to characterize the identity, subject sequences are aligned so that the highest order homology (match) is obtained. Based on these general principles, the "percent identity" of two nucleic acid sequences may be determined using the BLASTN algorithm [Tatiana A. Tatusova, Thomas L. Madden: Blast 2 sequences—a new tool for comparing protein and nucleotide sequences; *FEMS Microbiol. Lett.* 1999 174 247-250], which is available from the National Center for Biotechnology Information (NCBI) web site (http://www.ncbi.nim.nih.gov), and using the default settings suggested here (i.e. Reward for a match=1; Penalty for a mismatch=−2; Strand option=both strands; Open gap=5; Extension gap=2; Penalties gap x_dropoff=50; Expect=10; Word size=11; Filter on). The BLASTN algorithm determines the % sequence identity in a range of overlap between two aligned nucleotide sequences.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the FASTA sequence alignment software package (Pearson W R, Methods Mol Biol, 2000, 132:185-219). Align calculates sequence identities based on a global alignment. Align0 does not penalise to gaps in the end of the sequences. When utilizing the ALIGN og Align0 program for comparing amino acid sequences, a BLOSUM50 substitution matrix with gap opening/extension penalties of −12/−2 is preferably used.

DETAILED DESCRIPTION

The present invention relates to the medical use of polypeptides and polynucleotides being identified as NsG33. The NsG33 protein has been identified in human beings (SEQ ID No. 3), mouse (SEQ ID No. 8), and rat (SEQ ID No. 13).

Human NsG33 exists as a 293 amino acid precursor, which can be processed to give rise to at least one and potentially several biologically active peptides. NsG33 is expressed at high levels in the nervous system and the eye, and in particular subregions of the brain (FIGS. 4A and B). The longest mouse (SEQ ID No 8) and rat (SEQ ID No 13) NsG33 polypeptides consist of 294 and 291 amino acids, respectively and the % identities with the human protein are 80.3 and 80.2, respectively (See Table 1 and 2 in Example 2). It should be noted that the predicted full length mouse and rat polypeptide sequences are as yet unverified, and that at least the mouse polypeptide sequence is partial in the N-terminal. A full-length mouse protein sequence with a slightly different N-terminal has been published in Nishino et al (The EMBO Journal, 2004, 23:2998-2008) with a corresponding cDNA available from NCBI under accession number XM128551. Cleavage of the signal peptide from this mouse protein results in the mature protein having SEQ ID No. 9.

Figure 1A:
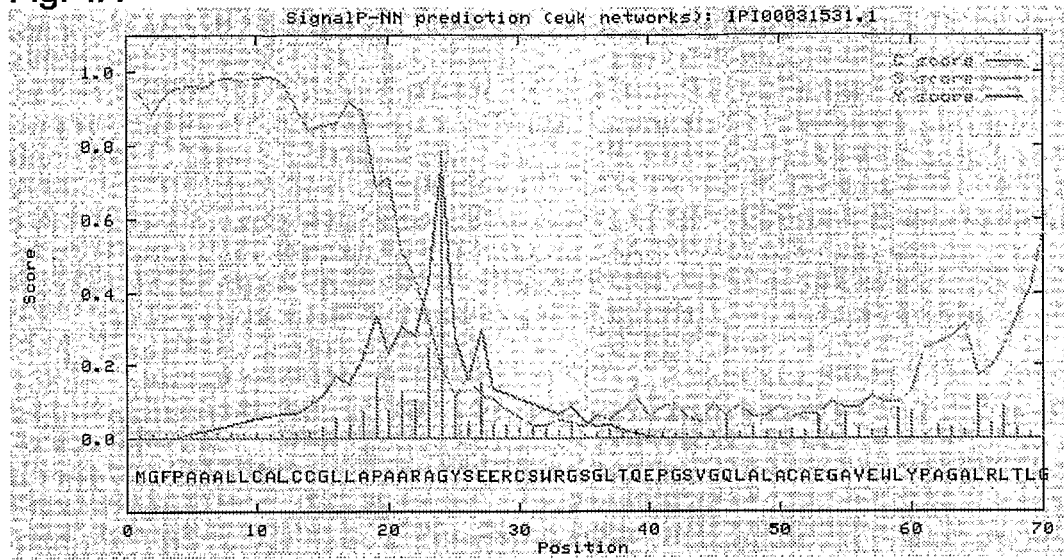
FIG. 1a: SignalP NN (Neural network) plot of human NsG33.
Figure 1B:
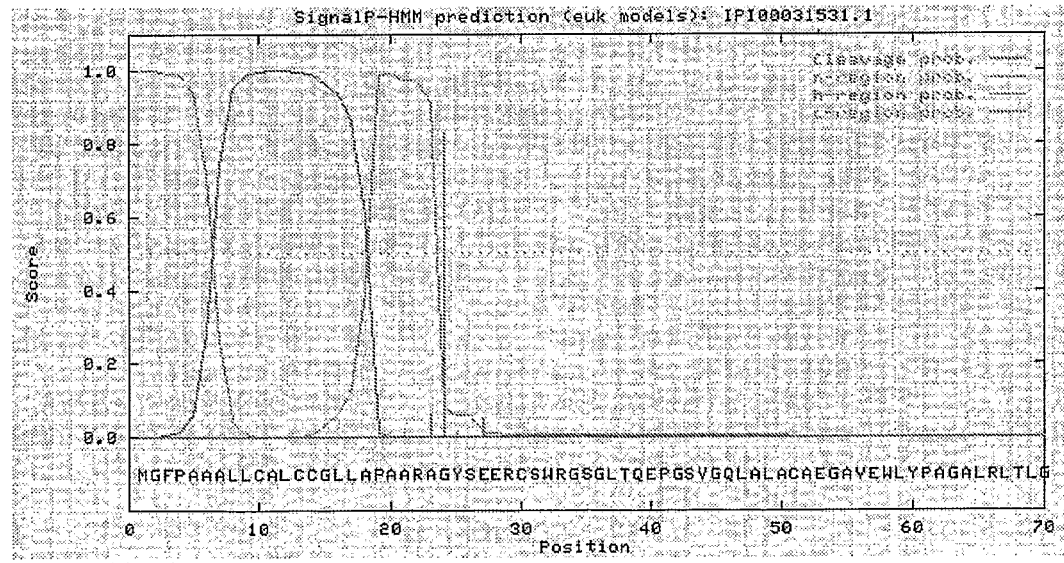
FIG. 1b: SignalP HMM (Hidden Markov Model) plot of human NsG33. For details, refer to example 2.

Human NsG33 contains an N-terminal signal peptide sequence of 23 amino acids, which is cleaved at the sequence motif ARA-GY (SEQ ID NO: 41). This signal peptide cleavage site is predicted by the SignalP method (see example 2) and the output graph shown in FIG. 1. However, one of skilled in the art will recognize that the actual cleavage site may be different than predicted by the computer program. For example the signal peptide prediction in rat NsG33 results in predictions with approximately equal probabilities at positon 16 and 21. A signal peptide cleavage site is found at a similar location in the mouse NsG33 (pos. 24) and rat NsG33 (pos. 16 or 21). Cleavage of the signal peptide results in polypeptides having SEQ ID No. 4, 9, and 14 for human, mouse, and rat respectively. As it is known in the art, signal peptide processing is not always exactly as predicted and actual cleavage may vary from case to case. Thus, it is expected that the N-terminal of mature NsG33 may vary by one to two or three amino acids from the predicted cleavage site. The actual N-terminal of mature NsG33 can be verified experimentally by C-terminal tagging with e.g. a his-tag, subsequent purification using a poly-his specific antibody or purification on a Ni column, and finally N-terminal sequencing of the purified mature peptide.

General-type proprotein cleavage is predicted in human NsG33 by the ProP method (Prediction of proprotein convertase cleavage sites. Peter Duckert, Søren Brunak and Nikolaj Blom. Protein Engineering, Design and Selection: 17: 107-112, 2004) at pos. 127 with a score of 0.831, sequence motif 'WGPRERR-AL' (SEQ ID NO: 42). Similar, cleavage sites are predicted in homologous positions in mouse NsG33 (at pos. 128) with a score of 0.831, sequence motif 'WGPRERR-AL' (SEQ ID NO: 42) and in rat NsG33 (at pos. 125) with a score of 0.831 and the sequence motif 'WGPRERR-AL' (SEQ ID NO: 42). A possible furin propeptide cleavage site is also found at position 121 in human NsG33 at sequence motif 'GGRCVR-WG' (SEQ ID NO: 43) and at corresponding positions in rat and mouse NsG33. Polypeptide processing after cleavage of the signal peptide results in the formation of a C-terminal peptide and an N-terminal peptide. Whether the protein is actually processed at these predicted sites may depend on the cell type, in which the gene is expressed. Propeptide cleavage can be experimentally verified by C-terminal his-tagging, purification and subsequent N-terminal sequencing of the tagged peptide.

NsG33 belongs to the category of proteins acting as growth factors. This notion is supported by predictions by the ProtFun protein function prediction server, which provides odds above 1.0 this type of category as shown in FIG. 2.

The ProtFun method predicts protein function based on sequence-derived features as opposed to sequence similarity. Features which are important for discriminating between the 'growth factor' classes versus all other classes are: protein sorting potential, protein targeting potential, signal peptide potential, low complexity regions, secondary protein structure, number of negative residues and number of atoms. In general, an odds score of 1 indicates a prediction which may have taken place by chance. Odds above 1 indicate that there is an increased probability that the protein does belong to the predicted gene ontology class. The higher the odds score, the higher the chance that the prediction is correct.

Results of the quantitative realtime-PCR are shown in FIGS. 4A and B. Based on the figures, tissues can be grouped according to the expression level of NsG33.

Tissues with high expression included:
Putamen, Substantia Nigra and Spinal Cord.
Tissues with intermediate expression included:
Whole brain, Cerebellum, Retina* and Dorsal Root Ganglion*
Tissues with low expression included:
Heart, kidney, Lung, Prostate, Salivary gland, skeletal muscle, testis, stomach, pancreas, Fetal Brain*.
Tissues with very low or no expression included:
Fetal Liver, Placenta, thymus, trachea, spleen, uterus, colon, small intestine.

When analysing results after normalisation to $\beta_2$-microglobulin expression essentially same results were seen except for the tissues marked with a *

The real-time PCR results for mouse NsG33 are shown in FIGS. 10A and 10B. CT values ranged from 17 to 22. From FIG. 10A, it is apparent that NsG33 expression is regulated during development of the Spinal Cord peaking around E11.5. From FIG. 10B, it is apparent that NsG33 is regulated during the postnatal development in Cerebellum but not in Cortex.

The temporal expression pattern in Spinal Cord indicates a role in proliferation, differentiation and/or survival of the neural progenitors in this region of the CNS. This is consistent with therapeutic relevance for treatment of neurodegenerative diseases and injuries in the Spinal Cord including Spinal Cord Injury, ALS, and spinal muscular atrophy. Furthermore, this expression profile indicates a potential as in vitro reagent for expansion and/or differentiation of neural progenitors derived from the Spinal Cord.

The up-regulation of NsG33 expression in the adult Cerebellum indicates a role for this factor in maintenance and/or survival of one or more cerebellar cell types. This is consistent with therapeutic relevance for cerebellar disorders including including but not limited to sensory ataxia, multiple sclerosis, neurodegenerative spinocerebellar disorders, hereditary ataxia, cerebellar atrophies (such as Olivopontocerebellar Atrophy (OPCA), Shy-Drager Syndrome (multiple systems atrophy)), and alcoholism.

Unlike structural proteins, growth factors are involved in cell signalling and in various functions such as growth, proliferation, differentiation, survival, regeneration, migration, regain of function and improvement of function. Therefore, growth factors can be administered and be used to exert a therapeutic effect.

Based on the tissue specific expression, and the fact that NsG33 is predicted to be a secreted growth factor, and that NsG33 possesses antiapoptotic, neuroprotective and/or neurogenesis activity (FIGS. 9, 11 and 12), NsG33 is contemplated for use in treating disorders of the nervous system in general (based on the nervous system specific expression), in particular Parkinson's disease (based on the expression in substantia nigra), Huntington's disease (based on expression in putamen and substantia nigra), cerebellar disorders (based on expression in human cerebellum, and differential expression in the developing mouse cerebellum), Spinal Cord injury (based on expression in the adult human spinal cord, and the differential expression in the developing mouse spinal cord), ALS (based on expression in the adult human spinal cord, and the differential expression in the developing mouse spinal cord), peripheral neuropathies (based on expression in dorsal root ganglion), and retinopathies (based on expression in retina). The function for the various indications can be verified in in vitro and in vivo assays as described in the examples.

Likewise, expression of therapeutically relevant secreted growth factors including GDNF, NGF, and Neublastin (Artemin) is found in target areas of the neurological disorder they may be used to treat.

The therapeutic effect of NsG33 may be mediated through an effect on growth including proliferation, regeneration, regain of function, improvement of function, survival, migration, and/or differentiation of targeted cells.

One verified biological function of NsG33 is a neuroprotective effect against starvation induced apoptosis in PC12 (pheochromocytoma) cells. Pheochromocytomas are tumours with characteristics of immature and adult chromaffin cells of the adrenal medulla. Chromaffin cells, sensory and sympathetic neurons in addition to pigment cells (melanocytes) are derived from a common precursor cell in the neural crest. Its differentiation into the specific lineages is highly dependent on external signals including secreted factors.

PC12 is a clonal cell line, which was originally established from a transplantable rat adrenal medullary pheochromocytoma (Greene and Tischler, 1976 Proc. Natl. Acad. Sci. U.S.A. 73, 2424). PC-12 cells are available from ATCC (American Type Culture Collection; accession number CRL-1721). PC12 cells are considered to be the pluripotent chromaffin precursor cell as it possesses the ability to differentiate to mature chromaffin cells, sympathetic neurons, as well as melanocytes depending on the culture conditions. PC12 cells have been widely used as a model system for studies of neuronal differentiation and survival. In serum-containing medium PC12 cells proliferate, whereas addition of certain neurotrophic factors including NGF induces differentiation of PC12 cells into a neuronal phenotype very similar to sympathetic neurons. In serum-free medium, PC12 cells will become apoptotic and die unless supplied with certain growth factors, hormones or small molecules that can act as survival factors.

The factors capable of inducing differentiation and survival in PC12 cells including one of the neurotrophins (NGF) and a member of the secretin/glucagon/VIP family (PACAP) also display a similar activity in both the peripheral and central nervous system indicating that receptors and response systems expressed in PC12 cells are shared with many other neuronal cells.

NGF is an important differentiation and survival factor for responsive sympathetic and sensory neurons in addition to cholinergic neurons in the basal forebrain. PACAP promotes the differentiation of nascent dorsal root ganglion (DRG) neurons in that it increases both the number of neural-marker-positive cells and axonogenesis without affecting the proliferation of neural progenitor cells (Nielsen et al., Mol Cell Neurosci. 2004 April; 25(4):629-41). PACAP also show similar activities in neuronal populations in the CNS (Vaudry et al., Proc Natl Acad Sci USA. 2002 Apr. 30; 99(9):6398-403; Dicicco-Bloom et al., Ann NY Acad Sci. 1998 Dec. 11; 865:274-89).

Apoptotic cell death contributes to the neuronal cell loss in the adult nervous system causing various neurological disorders like ischemic stroke, neurodegenerative diseases or brain traumata (Becker and Bonni, Prog Neurobiol. 2004 January; 72(1):1-25). A secreted growth factor capable of protecting neuronal cells against apoptotic cell death is therefore a candidate for treating disorders of the nervous system in general and neurodegenerative disorders in particular. Thus, the ability of a secreted factor to induce neurite outgrowth and/or to promote survival under conditions leading to apoptosis is an indication that this factor has a similar effect in other neuronal cell types of the central and/or peripheral nervous system and that this factor is a candidate for treating nervous system disorders, in particular neurodegenerative disorders.

Another biological function of NsG33 is a stimulating effect on the percentage of neurons generated by a human neural stem cell line (hNS1, formerly called HNSC.100). Cells exposed to conditioned medium from ARPE-19 cells transduced with human NsG33 coding sequence produced a higher percentage of neurons relative to astrocytes compared to hNS1 cells exposed to conditioned medium from non-transduced ARPE-19 cells. This is consistent with the anti-apoptotic effect found in the PC-12 assay. The effect may be caused by a survival effect on neurons and/or by neurogenesis and/or by proliferation of neuronal precursors. hNS1 cell line is established from human forebrain neurosphere cultures. Other known trophic factors with therapeutic potential have been shown to increase the number of neurons generated from human neurosphere cultures. These include NT3 and NT4/5 and platelet-derived growth factor (PDGF) (Caldwell et al, Nature Biotechnology, 2001 May, 19(5):475-9. Growth factors regulate the survival and fate of cells derived from human neurospheres). Consequently, these results also indicate that NsG33 is a candidate factor for treating disorders of the nervous system and in particular neurodegenerative disorders.

In a further in vitro assay, conditioned medium from two cell lines transfected with cDNA encoding human NsG33 increased the percentage of neurons in a primary culture of rat striatal cells. This assay is also consistent with a neuroprotective effect of NsG33. This effect may be caused by a survival effect on neurons and/or by neurogenesis and/or by proliferation of neuronal precursors. Other factors with therapeutic potential have a similar effect on rat striatal cultures including basic fibroblast growth factor (bFGF), truncated insulin-like growth factor-1 (tIGF), neurotrophin-3 (NT-3), brain-derived neurotrophic factor (BDNF), the BB-isoform of platelet-derived growth factor (PDGF-BB), and neurotrophin-4/5 (NT-4/5) (Nakao et al, Exp Neurol 1996, March 138(1):144-57, Differential trophic effects of basic fibroblast growth factor, insulin-like growth factor-1, and neurotrophin-3 on striatal neurons in culture; Nakao et al, Brain Res Dev Barin Res, 1995 Dec. 21; 90(1-2):92-101, Trophic and protective actions of brain-derived neurotrophic factor on striatal DARPP-32-containing neurons in vitro; Widmer et al Eur J Neurosci, 1994 Nov. 1; 6(11):1669-79, Neurotrophin 4/5 promotes survival and differentiation of rat striatal neurons developing in culture). Consequently, these results also indicate that NsG33 is a candidate factor for treating disorders of the nervous system and in particular neurodegenerative disorders.

NsG33 is structurally related to a protein described in WO 93/22437 (Innogenetics SA), which is identified in a BLASTP search. The full length human protein is shown in FIG. 2 of WO 93/22437. NsG33 shares 42% identity (Align0 with default settings) with the Innogenetics protein including 10 conserved cysteine residues. An N-terminal signal peptide of 45 residues is predicted in the Innogenetics protein (NsG34). Recombinant expression data from WO 93/22437 indicate that the Innogenetics protein is not subject to pro-peptide processing under the conditions used in that publication, but is secreted as a protein of 268 amino acids. This could be taken as an indication that the predicted pro-peptide cleavage of NsG33 may not take place when the gene is expressed, at least not in the cells used in the cited reference.

A full length alignment of human NsG33 to the human Innogenetics protein is shown in FIG. 5. The 10 conserved cysteines are shown in bold and are marked with asterisks. The two proteins together form a protein family based on the conserved cysteine residues and the stretches of high conservation which are evident from FIG. 5. None of the two proteins show any significant sequence homology to any other known human proteins. Although the two proteins are members of the same small protein family, the two proteins are structurally distinct.

Due to the high conservation of the cysteines, it is expected that these residues play an important role in the secondary and tertiary structure of the bioactive protein. One or more of the cysteines may participate in the formation of intra- and/or intermolecular cystin-bridges.

The Innogenetics protein is inter alia functional in activation of T-cells and B-cells and as an inducer of immunosuppressive cells. Based on the homology to the Innogenetics protein, NsG33 is predicted to similarly have functions involved in immunology.

I NsG33 Polypeptides

In addition to full-length NsG33, substantially full-length NsG33, to pro-NsG33, to C-terminal peptides, to N-terminal peptides and to truncated forms of NsG33, the present invention provides for biologically active variants of the polypeptides. An NsG33 polypeptide or fragment is biologically active if it exhibits a biological activity of naturally occurring NsG33. It is to be understood that the invention relates to substantially purified NsG33 as herein defined.

One biological activity is the ability to compete with naturally occurring NsG33 in a receptor-binding assay.

Another biological activity is the ability to bind to an antibody, which is directed at an epitope, which is present on naturally occurring NsG33.

Biologically active variants may also be defined with reference to one or more of the other in vitro and/or in vivo biological assays described in the examples.

A preferred biological activity is the ability to elicit substantially the same response as in the PC12 assay described in the Examples and FIG. 9. In this assay PC12 cells are transduced with full length human NsG33 coding sequence (FIG. 6). By substantially the same response in the PC12 assay is intended that the number of neurite bearing cells is at least 10% of the number obtained in Example 6 (transduction with full length human NsG33), more preferably at least 20%, more preferably at least 30%, more preferably at least 40%, more preferably at least 50%, more preferably at least 60%, more preferably at least 70%, more preferably at least 75%, more preferably at least 80%, more preferably at least 85%, more preferably at least 90%. The PC12 assay may also be used to document the percentage improvement in survival over a control treatment. Substantially the same response in this context means an activity resulting in at least 10% of the improvement obtained in Example 6 (FIG. 9), more preferably at least 20%, more preferably at least 30%, more preferably at least 40%, more preferably at least 50%, more preferably at least 60%, more preferably at least 70%, more preferably at least 75%, more preferably at least 80%, more preferably at least 90%. The biological activity of a fragment or variant of NsG33 may also be higher than that of the naturally occurring NsG33. Other preferred biological activities include the neuroprotective and/or neurogenesis effect shown in Examples 14 and 15.

Specific fragments of NsG33 include polypeptides selected from the group consisting of $AA_{128}$-$AA_{293}$ of SEQ ID No 3, $AA_{12}$-$AA_{293}$ of SEQ ID No 3, $AA_{129}$-$AA_{294}$ of SEQ ID No 8, $AA_{122}$-$AA_{294}$ of SEQ ID No 8, $AA_{126}$-$AA_{291}$ of SEQ ID No 13, $AA_{119}$-$AA_{291}$ of SEQ ID No 13, and sequence variants of said polypeptides, wherein any amino acid specified in the chosen sequence is changed to a different amino acid, provided that no more than 15 of the amino acid residues in the sequence are so changed. These isolated polypeptides constitute C-terminal peptides of NsG33. Preferably any changed amino acids are selected from those designated as unconserved, weakly conserved or strongly conserved in FIG. 3a. ProtFun 2.1 predicts with high odds (8.0) that C-terminal peptides belong to the gene ontology class growth factor (FIG. 2).

Further specific polypeptides are selected from the group consisting of SEQ ID No 19, 20, 21, 22, 23, and 24, and sequence variants of said polypeptides, wherein any amino acid specified in the chosen sequence is changed to a different amino acid, provided that no more than 15 of the amino acid residues in the sequence are so changed. These isolated polypeptides constitute N-terminal peptides of NsG33. Preferably any changed amino acids are selected from those designated as unconserved, weakly conserved or strongly conserved in FIG. 3a. In a preferred embodiment, less than 10 amino acids have been changed, more preferably less than 5 amino acids, more preferably 1 or 2 amino acids, more preferably no amino acids have been changed. ProtFun 2.1 predicts with high odds (8.1) that N-terminal peptides belong to the gene ontology class growth factor (FIG. 2).

Specific preferred truncated forms of NsG33 in one aspect, are selected from the group consisting of:
1) $AA_{30}$-$AA_{288}$ of SEQ ID No 3, and polypeptides having from one to five extra amino acids from the native sequence in one or both ends, up to $AA_{25}$-$AA_{293}$ of SEQ ID No 3;
2) $AA_{28}$-$AA_{286}$ of SEQ ID No 13 and polypeptides having from one to five extra amino acids from the native sequence in one or both ends, up to $AA_{23}$-$AA_{291}$ of SEQ ID No 13;
3) $AA_{31}$-$AA_{289}$ of SEQ ID No 8 and polypeptides having from one to five extra amino acids from the native sequence in one or both ends, up to $AA_{26}$-$AA_{294}$ of SEQ ID No 8; and
4) sequence variants of said polypeptides, wherein any amino acid specified in the chosen sequence is changed to a different amino acid, provided that no more than 20 of the amino acid residues in the sequence are so changed.

These truncated forms of NsG33 constitute a core sequence from the first to the last conserved cysteine. In a preferred embodiment, less than 15 amino acids have been changed, more preferably less than 10 amino acids, more preferably less than 5 amino acids, such as 1 or 2 amino acids, more preferably no amino acids have been changed.

Specific truncated forms of NsG33 in one aspect, are selected from the group consisting of:
1) $AA_{171}$-$AA_{288}$ of SEQ ID No 3, and polypeptides having from one to five extra amino acids from the native sequence in one or both ends, up to $AA_{165}$-$AA_{288}$ of SEQ ID No 3;
2) $AA_{169}$-$AA_{286}$ of SEQ ID No 13 and polypeptides having from one to five extra amino acids from the native sequence in one or both ends, up to $AA_{164}$-$AA_{291}$ of SEQ ID No 13;
3) $AA_{172}$-$AA_{289}$ of SEQ ID No 8 and polypeptides having from one to five extra amino acids from the native sequence in one or both ends, i.e. up to $AA_{167}$-$AA_{294}$ of SEQ ID No 8;
4) variants of said polypeptides, wherein any amino acid specified in the chosen sequence is changed to a different amino acid, provided that no more than 10 of the amino acid residues in the sequence are so changed.

These truncated forms constitute a bioactive core sequence from the first to the last conserved cysteine in C-terminal peptides. In a preferred embodiment, less than 10 amino acids have been changed, more preferably less than 5 amino acids, more preferably 1 or 2 amino acids, more preferably no amino acids have been changed.

Specific truncated forms of NsG33 in one aspect are selected from the group consisting of:
1) $AA_{30}$-$AA_{118}$ of SEQ ID No 3, and polypeptides having from one to five extra amino acids from the native sequence in one or both ends, up to $AA_{25}$-$AA_{123}$ of SEQ ID No 3;
2) $AA_{28}$-$AA_{116}$ of SEQ ID No 13 and polypeptides having from one to five extra amino acids from the native sequence in one or both ends, up to $AA_{23}$-$AA_{121}$ of SEQ ID No 13;
3) $AA_{31}$-$AA_{119}$ of SEQ ID No 8 and polypeptides having from one to five extra amino acids from the native sequence in one or both ends, up to $AA_{26}$-$AA_{124}$ of SEQ ID No 8; and
4) variants of said polypeptides, wherein any amino acid specified in the chosen sequence is changed to a different amino acid, provided that no more than 10 of the amino acid residues in the sequence are so changed.

These truncated forms constitute core sequences from the first to the fourth conserved cysteine in N-terminal NsG33 peptides. In a preferred embodiment, less than 10 amino acids have been changed, more preferably less than 5 amino acids, more preferably 1 or 2 amino acids, more preferably no amino acids have been changed.

Variants can differ from naturally occurring NsG33 in amino acid sequence or in ways that do not involve sequence, or in both ways. Variants in amino acid sequence ("sequence variants") are produced when one or more amino acids in naturally occurring NsG33 is substituted with a different natural amino acid, an amino acid derivative or non-native amino acid. Particularly preferred variants include naturally occurring NsG33, or biologically active fragments of naturally occurring NsG33, whose sequences differ from the wild type sequence by one or more conservative and/or semi-conservative amino acid substitutions, which typically have minimal influence on the secondary and tertiary structure and hydrophobic nature of the protein or peptide. Variants may also have sequences, which differ by one or more non-conservative amino acid substitutions, deletions or insertions, which do not abolish the NsG33 biological activity. The Clustal W alignment in FIG. 3a or FIG. 3b can be used to predict which amino acid residues can be substituted without substantially affecting the biological activity of the protein.

Substitutions within the following group (Clustal W, 'strong' conservation group) are to be regarded as conservative substitutions within the meaning of the present invention
-STA, NEQK (SEQ ID NO: 27), NHQK (SEQ ID NO: 28), NDEQ (SEQ ID NO: 29), QHRK (SEQ ID NO: 30), MILV (SEQ ID NO: 31), MILF (SEQ ID NO: 32), HY, FYW. Substitutions within the following group (Clustal W, 'weak' conservation group) are to be regarded as semi-conservative substitutions within the meaning of the present invention
-CSA, ATV, SAG, STNK (SEQ ID NO: 33), STPA (SEQ ID NO: 34), SGND (SEQ ID NO: 35), SNDEQK (SEQ ID NO: 36), NDEQHK (SEQ ID NO: 37), NEQHRK (SEQ ID NO: 38), VLIM (SEQ ID NO: 39), HFY.

Other variants within the invention are those with modifications which increase peptide stability. Such variants may contain, for example, one or more nonpeptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants. Incorporation of D-instead of L-amino acids into the polypeptide may increase its resistance to proteases. See, e.g., U.S. Pat. No. 5,219,990. Splice variants are specifically included in the invention.

When the result of a given substitution cannot be predicted with certainty, the derivatives may be readily assayed according to the methods disclosed herein to determine the presence or absence of biological activity. Preferably in the PC-12 and/or the hNS1 assays and/or the rat striatal culture assay.

In one embodiment, the polypeptide is a naturally occurring allelic variant of the sequence selected from the group consisting of SEQ ID No. 3, 4, 5, 8, 9, 10, 13, 14, 15, 19, 20, 21, 22, 23, and 24. This polypeptide may comprises an amino acid sequence that is the translation of a nucleic acid sequence differing by a single nucleotide from a nucleic acid sequence selected from the group consisting of SEQ ID No. 1, 2, 6, 7, 11, 12, 16, 17, and 18.

A variant polypeptide as described herein, in one embodiment comprises a polypeptide wherein any amino acid specified in the chosen sequence is changed to provide a conservative substitution.

The signal peptide may be replaced by a heterologous signal peptide.

Variants within the scope of the invention in one embodiment include proteins and peptides with amino acid sequences having at least 60 percent identity with human, murine or rat NsG33 (SEQ ID NO: 5, 10, and 15). More preferably the sequence identity is at least 65%, more preferably at least 70%, more preferably at least 75%, more preferably at least 80%, more preferably at least 85%, more preferably at least 90%, more preferably at least 95%, more preferably at least 98%.

Preferred variants within the scope of the invention in one embodiment include proteins and peptides with amino acid sequences having at least 60 percent identity with a polypeptide having the sequence of SEQ ID NO: 4, 9, or 14. More preferably the sequence identity is at least 65%, more preferably at least 70%, more preferably at least 75%, more preferably at least 80%, more preferably at least 85%, more preferably at least 90%, more preferably at least 95%, more preferably at least 98%. SEQ ID No 4, 9 and 14 correspond to the mature proteins after cleavage of the signal peptide and without any pro-peptide cleavage.

Variants within the scope of the invention in one embodiment include proteins and peptides with amino acid sequences having at least 60 percent identity with a polypeptide having the sequence of SEQ ID NO: 3, 8, or 13. More preferably the sequence identity is at least 65%, more preferably at least 70%, more preferably at least 75%, more preferably at least 80%, more preferably at least 85%, more preferably at least 90%, more preferably at least 95%, more preferably at least 98%.

Variants within the scope of the invention in one embodiment include proteins and peptides with amino acid sequences having at least 70% sequence identity with a protein having a sequence selected from the group consisting of SEQ ID No. 19, 20, 21, 22, 23, and 24, more preferably at least 75%, more preferably at least 80%, more preferably at least 95%, more preferably at least 98%, more preferably a protein having the sequence selected from the group consisting of SEQ ID No. 19, 20, 21, 22, 23, and 24.

Variants within the scope of the invention in one embodiment include proteins and peptides with amino acid sequences having at least 60 percent identity with a polypeptide having the sequence of SEQ ID NO: 19, 20, or 21. More preferably the sequence identity is at least 65%, more preferably at least 70%, more preferably at least 75%, more preferably at least 80%, more preferably at least 85%, more preferably at least 90%, more preferably at least 95%, more preferably at least 98%.

Variants within the scope of the invention in one embodiment include proteins and peptides with amino acid sequences having at least 60 percent identity with a polypeptide having the sequence of SEQ ID NO: 22, 23, or 24. More preferably the sequence identity is at least 65%, more preferably at least 70%, more preferably at least 75%, more preferably at least 80%, more preferably at least 85%, more preferably at least 90%, more preferably at least 95%, more preferably at least 98%.

In a preferred embodiment the sequence identity of the variant NsG33 is determined with reference to a human NsG33 polypeptide (SEQ ID No 3, 4, 5, 19 or 22).

For the purposes of determining homology the minimum length of comparison sequences will generally be at least 8 amino acid residues, usually at least 12 amino acid residues. For the purposes of the present invention, the percent sequence identity is preferably calculated in a range of overlap of at least 25 amino acids, more preferably at least 30 amino acids, more preferably at least 35, more preferably at least 40, more preferably at least 45, more preferably at least 50, more preferably at least 55, more preferably at least 60, such as at least 70, for example at least 80, such as at least 90, for example at least 100, such as at least 110, for example at least 120, such as at least 130, for example at least 150, the range being determined by BLASTP under default settings.

In one embodiment the percent sequence identity is calculated using global alignment (GAP or Align), so that the variant and SEQ ID sequences are aligned, the total number of identical amino acid residues calculated and divided by the length of the SEQ ID NO.

In one embodiment, a variant NsG33 comprises a naturally occurring allelic variant of the sequence selected from the group consisting of SEQ ID No 3, 4, 5, 8, 9, 10, 13, 14, and 15.

Said allelic variant sequence may be an amino acid sequence that is the translation of a nucleic acid sequence differing by a single nucleotide from a nucleic acid sequence selected from the group consisting of SEQ ID No 1, 2, 6, 7, 11, 12, 16, 17, and 18.

In one embodiment, the variants include proteins comprising an amino acid sequence having at least 60% sequence identity to SEQ ID NO 3, more preferably at least 65%, more preferably at least 70%, more preferably at least 75%, more preferably at least 80%, more preferably at least 85%, more preferably at least 90%, more preferably at least 95%, more preferably at least 98%.

In one embodiment, preferred variants include proteins comprising an amino acid sequence having at least 60% sequence identity to SEQ ID NO 4, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 5, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 8, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the preferred variants include proteins comprising an amino acid sequence having at least 60% sequence identity to SEQ ID NO 9, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 10, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 13, more preferably at least 65%, more preferably at least 70%, more preferably at least 75%, more preferably at least 80%, more preferably at least 85%, more preferably at least 90%, more preferably at least 95%, more preferably at least 98%.

In one embodiment, preferred variants include proteins comprising an amino acid sequence having at least 60% sequence identity to SEQ ID NO 14, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 15, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 19, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 20, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 21, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 22, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 23, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 24, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 26, more preferably at least 65%, more preferably at least 70%, more preferably at least 75%, more preferably at least 80%, more preferably at least 85%, more preferably at least 90%, more preferably at least 95%, more preferably at least 98%.

In one embodiment, a variant NsG33 at corresponding positions comprises the residues marked in FIG. 3a as fully conserved (*) (SEQ ID NO:60), more preferably a variant NsG33 also comprises at corresponding positions the residues marked in FIG. 3a as strongly conserved (: strongly conserved groups include: STA, NEQK, NHQK, NEDQ QHRK, MILV, MILF, HY FYW), more preferably a variant NsG33 also comprises at corresponding positions the residues marked in FIG. 3a as less conserved (. less conserved groups include: CSA, ATV, SAG, STNK, STPA, SGND, SNDEQK, NDEQHK, NEQHK, NEQHRK, VLIM, HFY). In particular, it is contemplated that the conserved cysteines (FIG. 5) must be located at corresponding positions in a variant NsG33.

Non-sequence modifications may include, for example, in vivo or in vitro chemical derivatisation of portions of naturally occurring NsG33, as well as acetylation, methylation, phosphorylation, carboxylation, PEG-ylation, or glycosylation. Just as it is possible to replace substituents of the protein, it is also possible to substitute functional groups, which are bound to the protein with groups characterized by similar features. Such modifications do not alter primary sequence. These will initially be conservative, i.e., the replacement group will have approximately the same size, shape, hydrophobicity and charge as the original group.

Many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, I. E. Creighton, Proteins-Structure and Molecular Properties, 2nd Ed., W. H. Freeman and Company, New York, 1993. Many detailed reviews are available on this subject, such as, for example, those provided by Wold, F., in Posttranslational Covalent Modification of Proteins, B. C. Johnson, Ed., Academic Press, New York, pp 1-12, 1983; Seifter et al., Meth. Enzymol. 182: 626-646, 1990 and Rattan et al., Protein Synthesis: Posttranslational Modifications and Aging, Ann. N.Y. Acad. Sci. 663: 48-62, 1992.

In addition, the protein may comprise a protein tag to allow subsequent purification and optionally removal of the tag using an endopeptidase. The tag may also comprise a protease cleavage site to facilitate subsequent removal of the tag. Non-limiting examples of affinity tags include a polyhis tag, a GST tag, a HA tag, a Flag tag, a C-myc tag, a HSV tag, a V5 tag, a maltose binding protein tag, a cellulose binding domain tag. Preferably for production and purification, the tag is a polyhis tag. Preferably, the tag is in the C-terminal portion of the protein.

The native signal sequence of NsG33 may also be replaced in order to increase secretion of the protein in recombinant production in other mammalian cell types.

It will be appreciated, as is well known and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translational natural processes and by entirely synthetic methods, as well and are all within the scope of the present invention.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications.

It will be appreciated that the same type of modification may be present to the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

Also included within the invention are agents, which specifically bind to a protein of the invention, or a fragment of such a protein. These agents include Ig fusion proteins and antibodies (including single chain, double chain, $F_{ab}$ fragments, and others, whether native, humanized, primatized, or chimeric). Additional descriptions of these categories of agents are in WO 95/16709, the disclosure of which is herein incorporated by reference.

Antibodies refer to intact molecules as well as fragments thereof, such as $F_{ab}$, $F_{(ab')}$, and $F_v$, which are capable of binding the epitopic determinant. Antibodies that bind NsG33 polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

Humanised antibodies, as used herein, refer to antibody molecules in which amino acids have been replaced in the non-antigen binding regions in order to more closely resemble a human antibody, while still retaining the original binding ability. Humanised antibodies may be used therapeutically to treat conditions, where it is desirable to limit or block the action of NsG33.

Also included within the scope of the present invention are immunoconjugates of antibodies and conjugates selected from the group consisting of: a cytotoxic agent such as a chemotherapeutic agent, a toxin, or a radioactive isotope; a member of a specific binding pair, such as avidin, or streptavidin, or an antigen; an enzyme capable of producing a detectable product. These immunoconjugates can be used to target the conjugates to cells expressing a NsG33 receptor.

Specific antibodies to any NsG33 are also useful in immunoassays to quantify the substance for which a given antibody has specificity. Specific antibodies to an NsG33 may also be bound to solid supports, such as beads or dishes, and used to remove the ligand from a solution, either for use in purifying the protein or in clearing it from the solution. Each of these techniques is routine to those of skill in the immunological arts.

Also with the scope of the present invention are NsG33 fusion proteins. An NsG33 fusion protein can be used to allow imaging of tissues which express a receptor for NsG33, or in the immunohistological or preparative methods described above for antibodies to an NsG33. Fusion proteins encompassing an NsG33 can be used to specifically target medical therapies against cells, which express an NsG33 receptor.

II NsG33 Nucleotide Sequences

The invention provides medical use of genomic DNA and cDNA coding for NsG33, including for example the human genomic nucleotide sequence (SEQ ID No. 1), the mouse and rat genomic sequences (SEQ ID No. 6 and 11), the nucleotide sequence of human, mouse and rat NsG33 cDNA (SEQ ID NO 2, 7, and 12), the sequences coding for NsG33 without signal peptide (nucleotides 187-996 of SEQ ID No 2, nucleotides 74-883 of SEQ ID No. 7 and nucleotides 64-873 of SEQ ID No. 12), and the sequences coding for N-terminal NsG33 fragments of human, mouse, and rat origin (SEQ ID NO 16, SEQ ID No. 17, and SEQ ID No. 18). The invention also provides the cDNA sequence coding for full length mouse NsG33 (SEQ ID No. 25).

Variants of these sequences are also included within the scope of the present invention.

The invention relates to an isolated nucleic acid molecule for medical use comprising a nucleic acid sequence encoding a polypeptide or its complementary sequence, said polypeptide comprising an amino acid sequence selected from the group consisting of:

a) the amino acid sequence selected from the group consisting of SEQ ID No. 3, 4, 5, 8, 9, 10, 13, 14, 15, 19, 20, 21, 22, 23, and 24;
b) a sequence variant of the amino acid sequence selected from the group consisting of SEQ ID No. 3, 4, 5, 8, 9, 10, 13, 14, 15, 19, 20, 21, 22, 23, and 24, wherein the variant has at least 70% sequence identity to said SEQ ID No.; and
c) a biologically active fragment of at least 50 contiguous amino acids of any of a) through b).

The nucleic acid molecule may comprise the nucleotide sequence of a naturally occurring allelic nucleic acid variant.

The nucleic acid molecule of the invention may encode a variant polypeptide, wherein the variant polypeptide has the polypeptide sequence of a naturally occurring polypeptide variant.

In one embodiment the nucleic acid molecule differs by a single nucleotide from a nucleic acid sequence selected from the group consisting of SEQ ID No. 1, 2, 6, 7, 11, 12, 16, 17, and 18.

Preferably the encoded polypeptide has at least 60% sequence identity to a sequence selected from the group consisting of SEQ ID No. 5, 10, and 15 preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID Nos.

In a preferred embodiment the encoded polypeptide has at least 60% sequence identity to a sequence selected from the group consisting of SEQ ID No. 3 and 4, preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID Nos. Said sequences constitute human NsG33.

In a preferred embodiment the encoded polypeptide has at least 60% sequence identity to a sequence selected from the group consisting of SEQ ID No. 19 and 22, preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID Nos. Said sequences constitute human NsG33.

In a preferred embodiment the encoded polypeptide has at least 60% sequence identity to the sequence of SEQ ID No. 5, preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID No. Said sequence constitutes human N-terminal NsG33 polypeptide.

In a preferred embodiment the encoded polypeptide has at least 60% sequence identity to a sequence selected from the group consisting of SEQ ID No. 4, 9 and 14, preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID Nos. Said sequence constitutes NsG33 without signal peptide.

In a preferred embodiment the encoded polypeptide has at least 70% sequence identity to a sequence selected from the group consisting of SEQ ID No. 3, 8, and 13, more preferably at least 75%, more preferably at least 80%, more preferably at least 95%, more preferably at least 98%, more preferably wherein said polypeptide has a sequence selected from the group consisting of SEQ ID No. 3, 8, and 13.

In a preferred embodiment the encoded polypeptide has at least 70% sequence identity to a sequence selected from the group consisting of SEQ ID No. 19, 20, 21, 22, 23, and 24, more preferably at least 75%, more preferably at least 80%, more preferably at least 95%, more preferably at least 98%, more preferably wherein said polypeptide has a sequence selected from the group consisting of SEQ ID No. 19, 20, 21, 22, 23, and 24.

In a preferred embodiment the encoded polypeptide has at least 70% sequence identity to SEQ ID No. 3, more preferably at least 75%, more preferably at least 80%, more preferably at least 95%, more preferably at least 98%, more preferably wherein said polypeptide has the sequence of SEQ ID No. 3.

In a preferred embodiment the encoded polypeptide has at least 70% sequence identity to SEQ ID No. 4, more preferably at least 75%, more preferably at least 80%, more preferably at least 95%, more preferably at least 98%, more preferably wherein said polypeptide has the sequence of SEQ ID No. 4.

In a preferred embodiment the encoded polypeptide has at least 70% sequence identity to SEQ ID No. 19, more preferably at least 75%, more preferably at least 80%, more preferably at least 95%, more preferably at least 98%, more preferably wherein said polypeptide has the sequence of SEQ ID No. 19.

In a preferred embodiment the encoded polypeptide has at least 70% sequence identity to SEQ ID No. 22, more preferably at least 75%, more preferably at least 80%, more preferably at least 95%, more preferably at least 98%, more preferably wherein said polypeptide has the sequence of SEQ ID No. 22.

In one aspect the nucleic acid molecule comprises a nucleotide sequence selected from the group consisting of
a) the nucleotide sequence selected from the group consisting of SEQ ID No. 1, 2, 6, 7, 11, 12, 16, 17, and 18;
b) a nucleotide sequence having at least 70% sequence identity to a nucleotide sequence selected from the group consisting of SEQ ID No. 1, 2, 6, 7, 11, 12, 16, 17, and 18;
c) a nucleic acid sequence of at least 150 contiguous nucleotides of a sequence selected from the group consisting of SEQ ID No. 1, 2, 6, 7, 11, 12, 16, 17, and 18;
c) the complement of a nucleic acid capable of hybridising with nucleic acid having the sequence selected from the group consisting of SEQ ID No. 1, 2, 6, 7, 11, 12, 16, 17, and 18 under conditions of high stringency; and d) the nucleic acid sequence of the complement of any of the above.

SEQ ID No 16, 17 and 18 represent the sequences coding for C-terminal NsG33 polypeptides from human, mouse and rat. For recombinant expression in a eukaryotic expression system, these are preferably ligated to appropriate signal sequence coding sequences to ensure that the NsG33 polypeptide is secreted from the cells.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence selected from the group consisting of SEQ ID NO: 2, 7, 12, 16, 17, and 18.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence selected from the group consisting of SEQ ID NO: 16, 17, and 18.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence selected from the group consisting of SEQ ID NO: 2 and 16.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence selected from the group consisting of nucleotides 187-996 of SEQ ID NO: 2, nucleotides 74-883 of SEQ ID No 7 and nucleotides 64-873 of SEQ ID No. 12. These sequence fragments code for NsG33 without signal peptide.

In one embodiment, the isolated polynucleotide of the invention has at least 60, more preferably at least 65%, more preferably at least 70%, more preferably at least 75%, more preferably at least 80%, preferably at least 85%, more preferred at least 90%, more preferred at least 95%, more preferred at least 98% sequence identity to the polynucleotide sequence presented as SEQ ID NO: 1.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 2.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 16.

In one embodiment, the isolated polynucleotide of the invention has at least 50%, preferably at least 60%, more preferably at least 70%, more preferably at least 75%, preferably at least 80%, preferably at least 85%, more preferred at least 90%, more preferred at least 95%, more preferred at least 98% sequence identity to a polynucleotide sequence presented as SEQ ID NO: 6.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 7.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 17.

In one embodiment, the isolated polynucleotide of the invention has at least 50%, preferably at least 60%, more preferably at least 70%, more preferably at least 75%, preferably at least 80%, preferably at least 85%, more preferred at least 90%, more preferred at least 95%, more preferred at least 98% sequence identity to a polynucleotide sequence presented as SEQ ID NO: 11.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 12.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 18.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 25.

A preferred group of isolated polynucleotides include SEQ ID No 1, 2, and 16, which are human NsG33 polynucleotides. Another preferred group of isolated polynucleotides include SEQ ID No. 2, 7, and 12, which represent the cDNA sequences. Generally the cDNA sequence is much shorter than the genomic sequences are are more easily inserted into an appropriate expression vector and transduced/fected into a production cell or a human cell in vivo or ex vivo.

In addition, the nucleotide sequences of the invention include sequences, which are derivatives of these sequences. The invention also includes vectors, liposomes and other carrier vehicles, which encompass one of these sequences or a derivative of one of these sequences. The invention also includes proteins transcribed and translated from NsG33 cDNA, preferably human NsG33 cDNA, including but not limited to human NsG33 and derivatives and variants.

In another embodiment, the invention relates to the use of the nucleic acids and proteins of the present invention to design probes to isolate other genes, which encode proteins with structural or functional properties of the NsG33 proteins of the invention. The probes can be a variety of base pairs in length. For example, a nucleic acid probe can be between about 10 base pairs in length to about 150 base pairs in length.

Alternatively, the nucleic acid probe can be greater than about 150 base pairs in length. Experimental methods are provided in Ausubel et al., "Current Protocols in Molecular Biology", J. Wiley (ed.) (1999), the entire teachings of which are herein incorporated by reference in their entirety.

The design of the oligonucleotide (also referred to herein as nucleic acid) probe should preferably follow these parameters:

i) it should be designed to an area of the sequence which has the fewest ambiguous bases, if any and
ii) it should be designed to have a calculated $T_m$ of about 80° C. (assuming 2° C. for each A or T and 4° C. for each G or C).

The oligonucleotide should preferably be labeled to facilitate detection of hybridisation. Labelling may be with $\gamma$-$^{32}$P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately $4\times10^6$ dpm/pmole. The bacterial culture containing the pool of full-length clones should preferably be thawed and 100 μL of the stock used to inoculate a sterile culture flask containing 25 ml of sterile L-broth containing ampicillin at 100 μg/ml.

The culture should preferably be grown to saturation at about 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 pg/ml and agar at 1.5% in a 150 mm petri dish when grown overnight at about 37° C. Other known methods of obtaining distinct, well-separated colonies can also be employed.

Standard colony hybridization procedures should then be used to transfer the colonies to nitrocellulose filters and lyse, denature and bake them. Highly stringent (also referred to herein as "high stringency") conditions are those that are at least as stringent as, for example, 1×SSC at about 65° C., or 1×SSC and 50% formamide at about 42° C. "Moderate stringency" conditions are those that are at least as stringent as 4×SSC at about 65° C., or 4×SSC and 50% formamide at about 42° C. "Reduced stringency" conditions are those that are at least as stringent as 4×SSC at about 50° C., or 6×SSC and 50% formamide at 40° C.

The filter is then preferably incubated at about 65° C. for 1 hour with gentle agitation in 6×SSC (20× stock is 175.3 g NaCl liter, 88.2 g Na citrate/liter, adjusted to pH 7.0 with NaOH) containing 0.5% SDS, 100 g/ml of yeast RNA, and 10 mM EDTA (approximately 10 mL per 150 mm filter). Preferably, the probe is then added to the hybridization mix at a concentration greater than or equal to $1\times10^6$ dpm/mL. The filter is then preferably incubated at about 65° C. with gentle agitation overnight. The filter is then preferably washed in 500 mL of 2×SSC/0.5% SDS at room temperature without agitation, preferably followed by 500 mL of 2×SSC/ 0.1% SDS at room temperature with gentle shaking for 15 minutes. A third wash with 0.1×SSC/0.5% SDS at about 65° C. for 30 minutes to 1 hour is optional. The filter is then preferably dried and subjected to autoradiography for sufficient time to visualize the positives on the X-ray film. Other known hybridization methods can also be employed. The positive colonies are then picked, grown in culture, and plasmid DNA isolated using standard procedures. The clones can then be verified by restriction analysis, hybridisation analysis, or DNA sequencing.

Alternatively, suitable experimental conditions for determining hybridization between a nucleotide probe and a homologous DNA or RNA sequence, involves pre-soaking of the filter containing the DNA fragments or RNA to hybridize in 5×SSC [Sodium chloride/Sodium citrate; cf. Sambrook et al.; *Molecular Cloning: A Laboratory Manual*, Cold Spring Harbor Lab., Cold Spring Harbor, N.Y. 1989] for 10 minutes, and pre-hybridization of the filter in a solution of 5×SSC, 5×Denhardt's solution [cf. Sambrook et al.; Op cit.], 0.5% SDS and 100 μg/ml of denatured sonicated salmon sperm DNA [cf. Sambrook et al.; Op cit.], followed by hybridization in the same solution containing a concentration of 10 ng/ml of a random-primed [Feinberg A P & Vogelstein B; *Anal. Biochem.* 1983 132 6-13], $^{32}$P-dCTP-labeled (specific activity>$1\times10^9$ cpm/μg) probe for 12 hours at approximately 45° C. The filter is then washed twice for 30 minutes in 0.1×SSC, 0.5% SDS at a temperature of at least at least 60° C. (medium stringency conditions), preferably of at least 65° C. (medium/high stringency conditions), more preferred of at least 70° C. (high stringency conditions), and even more preferred of at least 75° C. (very high stringency conditions). Molecules to which the oligonucleotide probe hybridizes under these conditions may be detected using a x-ray film.

In yet another embodiment, the invention relates to nucleic acid sequences (e.g., DNA, RNA) that hybridise to nucleic acids of NsG33. In particular, nucleic acids which hybridise to SEQ ID NO: 1, SEQ ID NO: 2, SEQ ID NO:6, SEQ ID NO:7, SEQ ID No. 11, SEQ ID No. 12, SEQ ID No 16, SEQ ID No 17, or SEQ ID No 18 under high, moderate or reduced stringency conditions as described above.

In still another embodiment, the invention relates to a complement of nucleic acid of NsG33. In particular, it relates to complements of SEQ ID NO: 1, SEQ ID NO: 2, SEQ ID NO: 6, SEQ ID No. 7, SEQ ID No 11, SEQ ID NO 12, SEQ ID No 16, SEQ ID No 17, and SEQ ID No 18.

In another embodiment, the invention relates to an RNA counterpart of the DNA nucleic acid of NsG33. In particular, it relates to RNA counterparts of SEQ ID NO: 2, SEQ ID NO: 7, SEQ ID NO: 12, SEQ ID No 16, SEQ ID No 17, and SEQ ID No 18.

Codon optimised nucleic acid molecules for enhanced expression in selected host cells, including but not limited to *E. coli*, yeast species, Chinese Hamster, Baby Hamster, insect, and fungus are also contemplated.

Variant nucleic acids can be made by state of the art mutagenesis methods. Methods for shuffling coding sequences from human with those of mouse, rat or chimpanzee are also contemplated. Specifically a shuffled variant may be between SEQ ID No 2 on one hand and 7 and/or 12 on the other hand. Also included are shuffled variants between SEQ ID No 7 and 12.

III Use of NsG33 Polypeptides, Polynucleotides, and NsG33 Secreting Cells for Treatment of Disorders of the Nervous System In one embodiment, native, variant NsG33, and fragments thereof and/or fusion proteins comprising NsG33 are provided for the treatment of disorders of the mammalian nervous system. NsG33 may be used to stimulate neural cell growth including proliferation, neural function, neural regeneration, neural differentiation, neural migration, and/or neural survival in disease situations where these cells are lost or damaged.

In one embodiment, polynucleotides and/or polypeptides of the invention may be used to treat conditions or diseases where neural growth including proliferation, differentiation, function, survival, and/or regeneration is desirable. The polypeptides of the present invention may be used directly via, e.g., injected, implanted or ingested pharmaceutical compositions to treat a pathological process responsive to the NsG33 polypeptides. This is supported by the bioinformatics analyses showing that NsG33 is a secreted growth factor, the fact that NsG33 is capable of protecting a neural cell line from apoptosis (Example 6), the fact that NsG33 causes generation of an increased percentage of neurons in a human neural progenitor cell differentiation assay and in primary rat striatal cultures, and the fact that NsG33 is preferentially expressed in the nervous system, including the eye (FIG. 4). The antiapoptotic effect of NsG33 makes it a candidate protein/gene for treatment of nervous system disorders involving apoptotic cell death. Such disorders include stroke, trauma and neurodegenerative disorders. The neuroprotective and/or neurogenesis effect of NsG33 supports the use for treating disorders caused by loss, dysfunction, or degeneration of neurons or their processes.

NsG33 may act on a range of different cell types, which are present in the nervous system. In the context of the present invention, the nervous system is intended to encompass the central nervous system, the peripheral nervous system, the eye, and the cochleovestibular complex.

In one embodiment, NsG33 polypeptides may act on neurons, including but not limited to motor neurons and sensory neurons.

In another embodiment, the therapeutic effect of NsG33 polypeptides may be through action on glial cells, such as oligodendrocytes and/or astrocytes. Through their action on glial cells, NsG33 polypeptides may be involved in myelination, and in the maintenance of neuron function and survival.

In another embodiment, NsG33 polypeptides may act on sensory cells, including but not limited to retinal ganglion cells, photoreceptor cells, supportive tissue such as retinal epithelial cells, and hair cells of the ear.

In a further embodiment, NsG33 polypeptides may act on stem cells, and downstream precursor cells including but not limited to neuronal precursors and glial precursors. NsG33 polypeptides may act on stem cells and/or neuronal or glial precursors to cause growth including proliferation, to cause differentiation, and/or migration. Stem cell therapy may be done through in vivo or ex vivo gene therapy, or the protein may be administered to a location with stem cells. This is supported by the effect of NsG33 on a human neural progenitor cell line.

The disorder or disease or damage may be damages of the nervous system caused by trauma, surgery, ischaemia, infection, metabolic diseases, nutritional deficiency, malignancy or toxic agents, and genetic or idiopathic processes.

In one embodiment of the method of the invention, the disease or disorder or damage involves injury to the brain, brain stem, the spinal cord, and/or peripheral nerves, resulting in conditions such as stroke, traumatic brain injury (TBI), spinal cord injury (SCI), diffuse axonal injury (DAI), epilepsy, neuropathy, peripheral neuropathy, and associated pain and other symptoms that these syndromes may cause.

In another embodiment, the disease, disorder, or damage involves the degeneration of neurons and their processes in the brain, brain stem, the spinal cord, and/or peripheral nerves, such as neurodegenerative disorders including but not limited to Parkinson's Disease, Alzheimer's Disease, senile dementia, Huntington's Disease, amyotrophic lateral sclerosis (ALS), neuronal/axonal injury associated with Multiple Sclerosis (MS), and associated symptoms.

In another embodiment, the disease, disorder, or damage involves dysfunction, and/or loss of neurons in the brain, brain stem, the spinal cord, and/or peripheral nerves, such as dysfunction and/or loss caused by metabolic diseases, nutritional deficiency, toxic injury, malignancy, and/or genetic or idiopathic conditions, including but not limited to diabetes, renal dysfunction, alcoholism, chemotherapy, chemical agents, drug abuse, vitamin deficiencies, infection, and associated symptoms.

In another embodiment, the disease, disorder, or damage involves the degeneration or sclerosis of glia such as oligodendrocytes, astrocytes, and Schwann cells in the brain, brain stem, the spinal cord, and peripheral nervous system, including but not limited to Multiple Sclerosis (MS), optic neuritis, cerebral sclerosis, post-infectious encephalomyelitis, and epilepsy, and associated symptoms.

In another embodiment, the disease, disorder, or damage involves the retina, photoreceptors, and associated nerves including but not limited to retinitis pigmentosa, macular degeneration, glaucoma, and associated symptoms.

In another embodiment, the disease, disorder, or damage involves the sensory epithelium and associated ganglia of the vestibuloacoustic complex, including but not limited to noise induced hearing loss, deafness, tinnitus, otitis, labyrintitis, hereditary and cochleovestibular atrophies, Meniere's Disease, and associated symptoms.

In a preferred embodiment, the polypeptides, nucleic acids, expression vectors, capsules and pharmaceutical compositions of the invention are used in the treatment of Parkinson's Disease. This function is based on the finding of high levels of expression in the central midbrain in substantia nigra and the putamen (see Example 5) and the finding of expression in the mesencephalon during human embryo development (Example 3), the fact that NsG33 causes generation of an increased percentage of neurons in a human neural progenitor cell differentiation assay and in primary rat striatal cultures, and is supported by the finding of protection against apoptotic cell death (Example 6). The function can be verified using the Bioassay for dopaminergic neurotrophic activities (example 11) and in vivo through the instrastriatal 6-OHDA lesion model (Example 12).

Huntington's disease (HD) is an autosomal dominant disorder that results in the progressive degeneration of various neuronal populations within the brain, particularly the GABA-ergic medium spiny neurons located in the caudate nucleus. Associated with this degeneration, the cortical glutaminergic input neurons also degenerate and the combined degeneration account for most of the characteristic symptoms of progressive dyskinetic motor movements as well as dementia.

In a preferred embodiment, the polypeptides, nucleic acids, expression vectors, capsules and pharmaceutical compositions of the invention are used in the treatment of Huntington's disease. This is based on the finding of high expression in the putamen combined with the results of the bioinformatics analyses and the neuroprotective/neurogenesis activity of NsG33 (In particular Example 15, but also Examples 6 and 14). Huntington's disease is an excitotoxic disease. An excitotoxic bioassay is the assay described in Example 12 of the present invention. Another exemplary bioassay for verification of this neuroprotective effect of NsG33 include e.g. the bioassay on protection of primary hippocampal slice cultures against the excitoxic effects of NMDA (WO 03/004527, example 5).

In another preferred embodiment, the polypeptides, nucleic acids, expression vectors, capsules and pharmaceutical compositions of the invention are used in the treatment of peripheral neuropathies. This is based on the finding of high expression in the dorsal root ganglion combined with the results of the bioinformatics analyses and with the neuroprotective/neurogenesis activity and antiapoptotic effect of NsG33 (Examples 6, 14 and 15). Verification of this function can be done with the dorsal root ganglion culture assay described in example 9. Among the peripheral neuropathies contemplated for treatment with the molecules of this invention are trauma-induced neuropathies, e.g., those caused by physical injury or disease state, physical damage to the peripheral nerves such as herniated discs, and the brain, physical damage to the spinal cord, stroke associated with brain damage, and neurological disorders related to neurodegeneration. We also contemplate treatment of chemotherapy-induced neuropathies (such as those caused by delivery of chemotherapeutic agents, e.g., taxol or cisplatin); toxin-induced neuropathies, drug-induced neuropathies, vitamin-deficiency-induced neuropathies; idiopathic neuropathies; and diabetic neuropathies.

In another preferred embodiment, the polypeptides, nucleic acids, expression vectors, capsules, and compositions of the invention are used in the treatment of disorders, diseases, or damages associated with the Cerebellum, including but not limited to sensory ataxia, multiple sclerosis, neurodegenerative spinocerebellar disorders, hereditary ataxia, cerebellar atrophies (such as Olivopontocerebellar Atrophy (OPCA), Shy-Drager Syndrome (multiple systems atrophy)), and alcoholism. This function is supported by the high expression levels in the adult human cerebellum and the differential expression in the developing mouse cerebellum, combined with the bioinformatics analyses and the neuroprotective/neurogenesis activity and antiapoptotic effect of NsG33 (Examples 6, 14, and 15). Verification of this function may be done with the assays described in Examples 7 and 8 (Protection of cerebellar granule cells from glutamate toxicity and potassium deprivation).

In another preferred embodiment, the polypeptides, nucleic acids, expression vectors, capsules and pharmaceutical compositions of the invention are used in the treatment of amyotrophic lateral sclerosis, spinal muscular atrophy, and spinal cord injury (e.g. ischemic or traumatic). This is based on the finding of high expression levels in the adult human spinal cord and the differential expression in the developing mouse spinal cord, combined with the results of the bioinformatics analyses and with the neuroprotective/neurogenesis activity and antiapoptotic effect of NsG33 (Examples 6, 14 and 15). Verification of this specific therapeutic function may be done with the motorneuron assay described in example 10.

In a preferred embodiment, the polypeptides, nucleic acids, vectors, capsules, and compositions of the invention are used in the treatment of diseases, disorders, or damages involving the retina, including but not limited to retinitis pigmentosa, macular degeneration and glaucoma. This specific therapeutic use is supported by the bioinformatics and experimental analyses showing that NsG33 is a secreted growth factor highly expressed in the retina (FIG. 4).

Other growth factors have important therapeutic uses in both the central and peripheral nervous system and in various eye indications associated with loss of cells in retina and/or cornea. E.g. NGF, is a candidate for both Alzheimer's disease, corneal ulcer (U.S. Pat. No. 6,063,757 and EP 0 973 872), and retinopathies. Neublastin (Artemin) is a candidate for both peripheral neuropathy (WO 02/078730) and corneal wound healing (EP 1 223 966). GDNF is a candidate for Parkinson's Disease, ALS, spinal cord injury, and for wound healing, in particular in cornea (EP 1 223 966).

Confirmation of such use can be obtained by using various state of the art in vitro assays (retinal explant assays, corneal cultures). Verification of function may also be performed in state of the art animal models for corneal wounds (corneal lesion in rabbits) and retina (retinitis pigmentosa mutant models available for mouse and rat).

In another embodiment the neurodegenerative disease is an excitotoxic disease selected from the group consisting of ischaemia, epilepsy, and trauma due to injury, cardiac arrest or stroke. This function is also supported by the neuroprotective/neurogenesis activity and antiapoptotic activity of NsG33 (Examples 6, 14 and 15). The above-mentioned hippocampal slice culture assay and the assay of Example 7 of the present invention are non-limiting examples of an assay, which can be used to demonstrate a biological effect, indicative of therapeutic use for the treatment of excitotoxic diseases.

The term "subject" used herein is taken to mean any mammal to which NsG33 polypeptide or polynucleotide, therapeutic cells or biocompatible capsules may be administered. Subjects specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts.

IV Treatment of Immunological Disorders

In one embodiment, NsG33 is contemplated for use in treating immunological disorders. This particular function of NsG33 is based on the structural similarity of NsG33 to a protein with immunological functions described in WO 93/22437 as described above.

According to this embodiment, NsG33 may exhibit immune stimulating or immune suppressing activity, including without limitation the activities for which assays are described herein. NsG33 may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g. HIV) as well as bacterial or fungal infections, or may result from autoimmune disorders. More specifically, infectious diseases causes by viral, bacterial, fungal or other infection may be treatable using NsG33, including infections by HIV, hepatitis viruses, herpes viruses, mycobacteria, *Leishmania* spp., *Malaria* spp. and various fungal infections such as candidiasis. In this regard, NsG33 may also be useful where a boost to the immune system generally may be desirable, i.e., in the treatment of cancer.

Autoimmune disorders which may be treated using NsG33 include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. NsG33 protein (or antagonists thereof, including antibodies) may also to be useful in the treatment of allergic reactions and conditions (e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies), such as asthma (particularly allergic asthma) or other respiratory problems. Other conditions, in which immune suppression is desired (including, for example, organ transplantation), may also be treatable using an NsG33 protein (or antagonists thereof). The therapeutic effects of the polypeptides or antagonists thereof on allergic reactions can be evaluated by in vivo animals models such as the cumulative contact enhancement test (Lastborn et al., Toxicology 125: 59-66, 1998), skin prick test (Hoffmann et al., Allergy 54: 446-54, 1999), guinea pig skin sensitization test (Vohr et al., Arch. Toxocol. 73: 501-9), and murine local lymph node assay (Kimber et al., J. Toxicol. Environ. Health 53: 563-79).

Using NsG33 it may also be possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or energy in T cells, is distinguishable from immunosuppression in that it is generally antigen-specific and persists after exposure to the tolerizing agent has ceased.

Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g. preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation.

Typically, in tissue transplants, rejection of the transplant is initiated through its recognition as foreign by T cells, followed by an immune reaction that destroys the transplant. The administration of a pharmaceutical composition of the invention may prevent cytokine synthesis by immune cells, such as T cells, and thus acts as an immunosuppressant. Moreover, a lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular pharmaceutical compositions in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257: 789-792 (1992) and Turka et al., Proc. Natl. Acad. Sci USA, 89: 11102-11105 (1992). In addition, murine models of GVHD (see Paul ed., Fundamental Immunology, Raven Press, New York, 1989, pp. 846-847) can be used to determine the effect of therapeutic compositions of the invention on the development of that disease.

Blocking antigen function may also be therapeutically useful for treating autoimmune diseases. Many autoimmune disorders are the result of inappropriate activation of T cells that are reactive against self-tissue and which promote the production of cytokines and autoantibodies involved in the pathology of the diseases. Preventing the activation of autoreactive T cells may reduce or eliminate disease symptoms. Administration of reagents which block stimulation of T cells can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRUlpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840-856).

Upregulation of an antigen function (e.g. a B lymphocyte antigen function), as a means of up regulating immune responses, may also be useful in therapy. Upregulation of immune responses may be in the form of enhancing an existing immune response or eliciting an initial immune response. For example, enhancing an immune response may be useful in cases of viral infection, including systemic viral diseases such as influenza, the common cold, and encephalitis.

Alternatively, anti-viral immune responses may be enhanced in an infected patient by removing T cells from the patient, costimulating the T cells in vitro with viral antigen-pulsed APCs either expressing an NsG33 or together with a stimulatory form of a soluble NsG33 of the present invention and reintroducing the in vitro activated T cells into the patient. Another method of enhancing anti-viral immune responses would be to isolate infected cells from a patient, transfect them with a nucleic acid encoding NsG33 as described herein such that the cells express all or a portion of the protein on their surface, and reintroduce the transfected cells into the patient. The infected cells would now be capable of delivering a costimulatory signal to, and thereby activate, T cells in vivo.

NsG33 may provide the necessary stimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g. a cytoplasmic-domain truncated portion) of an MHC class I alpha chain protein and $\beta_2$ microglobulin protein or an MHC class II alpha chain protein and an MHC class II beta chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of NsG33 may, among other means, be measured by the following methods: Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1-3.19; Chapter 7, Immunologic studies in Humans); Herrmann et al., Proc. Natl. Acad. Sci. USA 78: 2488-2492, 1981; Herrmann et al., J. Immunol. 128: 1968-1974, 1982; Handa et al., J. Immunol. 135: 1564-1572, 1985; Takai et al., J. Immunol. 137: 3494-3500, 1986; Takai et al., J. Immunol. 140: 508-512, 1988; Bowman et al., J. Virology 61: 1992-1998; Bertagnolli et al., Cellular Immunology 133: 327-341, 1991; Brown et al., J. Immunol. 153: 3079-3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144: 3028-3033, 1990; and Assays for B cell function: In vitro antibody production, Mond, J. J. and Brunswick, M. In Current Protocols in Immunology. J. E. e.a. Coligan eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137: 3494-3500, 1986; Takai et al., J. Immunol. 140: 508-512, 1988; Bertagnolli et al., J. Immunol. 149: 3778-3783, 1992.

Dendritic cell-dependent assays (which will identify, among others, proteins expressed by dendritic cells that activate naive T-cells) include, without limitation, those described in: Guery et al., J. Immunol. 134: 536-544, 1995; Inaba et al., Journal of Experimental Medicine 173: 549-559, 1991; Macatonia et al., Journal of Immunology 154: 5071-5079, 1995; Porgador et al., Journal of Experimental Medicine 182: 255-260, 1995; Nair et al., Journal of Virology 67: 4062-4069, 1993; Huang et al., Science 264: 961-965, 1994; Macatonia et al., Journal of Experimental Medicine 169: 1255-1264, 1989; Bhardwaj et al., Journal of Clinical Investigation 94:797-807, 1994; and Inaba et al., Journal of Experimental Medicine 172: 631-640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13: 795-808, 1992; Gorczyca et al., Leukemia 7: 659-670, 1993; Gorczyca et al., Cancer Research 53: 1945-1951, 1993; Itoh et al., Cell 66: 233-243, 1991; Zacharchuk, Journal of Immunology 145: 4037-4045, 1990; Zamai et al., Cytometry 14: 891-897, 1993; Gorczyca et al., International Journal of Oncology 1: 639-648, 1992.

Assays for proteins that influence early steps of T-cell commitment and development include, without limitation, those described in: Antica et al., Blood 84: 111-117, 1994; Fine et al., Cellular Immunology 155: 111-122, 1994; Galy et al., Blood 85: 2770-2778, 1995; Toki et al., Proc. Nat. Acad Sci. USA 88: 7548-7551, 1991.

V. Polypeptide Administration and Formulations

A target tissue for NsG33 therapy is a region of the brain is selected for its retained responsiveness to NsG33. In humans, neurons, which retain responsiveness to growth factors into adulthood include the cholinergic basal forebrain neurons, the entorhinal cortical neurons, the thalamic neurons, the locus coeruleus neurons, the spinal sensory neurons, the spinal motor neurons, neurons of substantia nigra, sympathetic neurons, dorsal root ganglia, retina neurons, optic neurons, cerebellar neurons, and ciliary ganglia. Stem cells, such as stem cells of the subventricular zone, and neural and glial progenitor cells also retain responsiveness to growth factors into adulthood. Also myelinating oligodendrocytes retain responsiveness to growth factors into adulthood.

NsG33 polypeptides may be administered in any manner, which is medically acceptable. This may include injections, by parenteral routes such as intravenous, intravascular, intraarterial, subcutaneous, intramuscular, intratumor, intraperitoneal, intraventricular, intraepidural, intertracheal, intrathecal, intracerebroventricular, intercerebral, interpulmonary, or others as well as nasal, ophthalmic, rectal, or topical. Sustained release administration is also specifically included in the invention, by such means as depot injections or erodible implants. Peroral administration is also conceivable provided the protein is protected against degradation in the stomach.

Administration of an NsG33 according to this invention may be achieved using any suitable delivery means, including:
  pump (see, e.g., Annals of Pharmacotherapy, 27:912 (1993); Cancer, 41:1270 (1993); Cancer Research, 44:1698 (1984), incorporated herein by reference),
  microencapsulation (see, e.g., U.S. Pat. Nos. 4,352,883; 4,353,888; and 5,084,350, herein incorporated by reference),
  continuous release polymer implants (see, e.g., Sabel, U.S. Pat. No. 4,883,666, incorporated herein by reference),
  encapsulated cells (see, Section X),
  naked or unencapsulated cell grafts to the CNS (see, e.g., U.S. Pat. Nos. 5,082,670 and 5,618,531, each incorporated herein by reference);
  injection, either subcutaneously, intravenously, intra-arterially, intramuscularly, or to other suitable site;
  inhalation; and
  oral administration, in capsule, liquid, tablet, pill, or prolonged release formulation.

Administration may be by periodic injections of a bolus of the preparation, or may be made more continuous by intravenous or intraperitoneal administration from a reservoir which is external (e.g., an IV bag) or internal (e.g., a bioerodable implant, a bioartificial organ, a biocompatible capsule of NsG33 production cells, or a colony of implanted NsG33 production cells). See, e.g., U.S. Pat. Nos. 4,407,957, 5,798,113, and 5,800,828, each incorporated herein by reference. Intrapulmonary delivery methods and apparatus are described, for example, in U.S. Pat. Nos. 5,654,007, 5,780, 014, and 5,814,607, each incorporated herein by reference.

Apart from systemic delivery, delivery directly to the CNS or the eye behind the blood-brain or blood-retina barriers is also contemplated.

Localised delivery may be by such means as delivery via a catheter to one or more arteries, such as the ophthalmic artery to the eye, and the cerebral artery to the CNS. Methods for local pump-based delivery of protein formulations to the CNS are described in U.S. Pat. No. 6,042,579 (Medtronic). Another type of localised delivery comprises delivery using encapsulated cells (see Section X). A further type of localised delivery comprises local delivery of gene therapy vectors, which are normally injected.

For the treatment of eye disorders, delivery may be systemic, or local such as delivery via the ophthalmic artery. In another embodiment, delivery is via Encapsulated Cell Therapy, where the encapsulated cells are implanted intravitreally. Delivery of protein formulations or gene therapy vector may be done using subretinal injections, intravitreal injection, or transcleral injection.

For the treatment of Parkinson's Disease, various delivery routes can be taken. Protein formulations can be administered with pumps intracerebroventricularly or intraparenchymally, preferably to the striatum and/or substantia nigra, more preferably to the intraputamen. However, a more preferred delivery method comprises encapsulated cell therapy, where the capsules are implanted intracerebroventricularly, or intraparenchymally, preferably into the striatum, and/or substantia nigra, and more preferably into the putamen. In one embodiment relating to treatment of Parkinson's Disease, gene therapy vector is administered to the striatum of the brain. Injection into the striatum can label target sites located in various distant regions of the brain, for example, the globus pallidus, amygdala, subthalamic nucleus or the substantia nigra. Transduction of cells in the pallidus commonly causes retrograde labelling of cells in the thalamus. In a preferred embodiment the (or one of the) target site(s) is the substantia nigra.

In an embodiment to treat HD, NsG33 is applied to the striatum, preferably the caudate nucleus in order to protect the neurons from degeneration, resulting in both protection of the caudate neurons and the cortical input neurons. In a preferred embodiment, the application should occur before the onset of major degenerative changes. The treatment would involve the genetic diagnosis of the disease through family history and DNA analysis of the blood followed by the local application of NsG-33. This would be accomplished by delivering the NsG33 to the striatum via pumping of the protein with the use of medically applicable infusion pumps and catheters, e.g. Medtronic Synchrotron pump. In a second strategy, direct gene therapy using viral or nonviral vectors could be utilized to modify the host cells in the striatum or other affected neurons to secrete NsG33. In a third strategy, naked or encapsulated cells genetically modified to make and secrete NsG33 can be applied locally to deliver NsG33 behind the blood-brain-barrier and within the diseased region, preferably the striatum, even more preferred, the caudate nucleus.

In ALS, both upper and lower motor neurons degenerate, causing progressive paralyses, eventually leading to death, most commonly through respiratory complications. To treat ALS, NsG33 would be delivered to the CNS including the spinal cord through the infusion of NsG33 into the lumbar intrathecal space thereby mixing with the cerebrospinal fluid (CSF), which bathes the spinal cord and brain. The delivery could be accomplished through the implantation of pump and catheters, e.g. Medtronic Synchrotron pump or through the use of encapsulated cell devices implanted into the lumbar inthrathecal space. Direct gene therapy could also be used by injecting DNA carrying vectors into the CSF, thereby transferring the gene to cells lining the CSF space. In addition, gene transfer vectors can be injected into the cervical or lumbar spinal cord or intracerebral, thereby secreting NsG33 in the anatomical regions containing the majority of the motor neurons involved in motor paralyses and respiratory function. These injections would occur under surgical navigation and could be performed relatively safely.

In subjects with neurodegenerative diseases such as AD, neurons in the Ch4 region (nucleus basalis of Meynert) which have nerve growth factor (NGF) receptors undergo marked atrophy as compared to normal controls (see, e.g., Kobayashi, et al., Mol. Chem. Neuropathol., 15: 193-206 (1991)).

In normal subjects, neurotrophins prevent sympathetic and sensory neuronal death during development and prevents cholinergic neuronal degeneration in adult rats and primates (Tuszynski, et al., Gene Therapy, 3: 305-314 (1996)). The resulting loss of functioning neurons in this region of the basal forebrain is believed to be causatively linked to the cognitive decline experienced by subjects suffering from neurodegenerative conditions such as AD (Tuszynski, et al., supra and, Lehericy, et al., J. Comp. Neurol., 330: 15-31 (1993)).

In general it is contemplated, that AD can be treated with NsG33 protein formulations delivered intracerebroventricularly, or intraparenchymally. Within the intraparenchymal area, delivery is preferably to the basal forebrain, and to the hippocampus.

Gene therapy vector, encapsulated or naked cells secreting NsG33 can also be administered to the basal forebrain or the hippocampus.

For the treatment of spinal cord injury, protein, gene therapy vector or encapsulated or naked cells secreting NsG33 can be delivered intrathecally at the position of the injury as described above for the treatment of ALS.

For the treatment of peripheral neuropathy, delivery is either systemic (using protein formulations), intrathecally using protein formulations, gene therapy vectors, or encapsulated or naked cells secreting NsG33, or intramuscularly depending on retrograde transport to the spinal cord.

For the treatment of epilepsy NsG33 protein could be delivered intraparenchymally in the epilepsy focus. This may be done with encapsulated or naked cells, with protein formulation administered with catheter or pump or with gene therapy vector delivered to this site.

For the treatment of stroke or trauma, delivery is intrathecal, intracerebroventricular, or preferably intralessionar.

The term "pharmaceutically acceptable carrier" means one or more organic or inorganic ingredients, natural or synthetic, with which NsG33 polypeptide is combined to facilitate its application. A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount an be determined by one of ordinary skill in the art employing such factors and using no more than routine experimentation.

A liposome system may be any variety of unilamellar vesicles, multilamellar vesicles, or table plurilamellar vesicles, and may be prepared and administered according to methods ell known to those of skill in the art, for example in accordance with the teachings of U.S. Pat. Nos. 5,169, 637, 4,762,915, 5,000,958 or 5,185,154. In addition, it may be desirable to express the novel polypeptides of this invention, as well as other selected polypeptides, as lipoproteins, in order to enhance their binding to liposomes. A recombinant NsG33 protein is purified, for example, from CHO cells by immunoaffinity chromatography or any other convenient method, then mixed with liposomes and incorporated into them at high efficiency. The liposome-encapsulated protein may be tested in vitro for any effect on stimulating cell growth.

Any of the NsG33 polypeptides of this invention may be used in the form of a pharmaceutically acceptable salt. Suitable acids and bases which are capable of forming salts with an NsG33 polypeptide are well known to those of skill in the art, and include inorganic and organic acids and bases.

In addition to the active ingredients, the pharmaceutical compositions may comprise suitable ingredients. Further details on techniques for formulation and administration may be found in the latest edition of *Remington's Pharmaceutical Sciences* (Maack Publishing Co., Easton, Pa.).

Various dosing regimes for systemic administration are contemplated. In one embodiment, methods of administering to a subject a formulation comprising an NsG33 polypeptide include administering NsG33 at a dosage of between 1 µg/kg to 30,000 µg/kg body weight of the subject, per dose. In another embodiment, the dosage is between 10 µg/kg to 30,000 µg/kg body weight of the subject, per dose. In a further embodiment, the dosage is between 10 µg/kg to 10,000 µg/kg body weight of the subject, per dose. In a different embodiment, the dosage is between 25 µg/kg to 10,000 µg/kg body weight of the subject, per dose. In yet another embodiment, the dosage is between 25 µg/kg to 3,000 µg/kg body weight of the subject, per dose. In a most preferable embodiment, the dosage is between 50 µg/kg to 3,000 µg/kg body weight of the subject, per dose.

Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of an NsG33 polypeptide is desired in a formulation with release characteristics suitable for the treatment of any disease or disorder requiring administration of an NsG33 polypeptide, microencapsulation of an NsG33 polypeptide is contemplated. Microencapsulation of recombinant proteins for sustained release has been successfully performed with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology, 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41.

The dose administered must be carefully adjusted to the age, weight and condition of the individual being treated, as well as the route of administration, dosage form and regimen, and the result desired, and the exact dosage should be determined by the practitioner.

VI. Pharmaceutical Preparations for Gene Therapy

To form an NsG33 composition for gene therapy use in the invention, NsG33 encoding expression viral vectors may be placed into a pharmaceutically acceptable suspension, solution or emulsion. Suitable mediums include saline and liposomal preparations.

More specifically, pharmaceutically acceptable carriers may include sterile aqueous of nonaqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils.

Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like. Further, a composition of NsG33 transgenes may be lyophilized using means well known in the art, for subsequent reconstitution and use according to the invention.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (LUV), which range in size from 0.2-4.0 µm can encapsulate a substantial percentage of an aqueous buffer containing large macro molecules. RNA, DNA and intact virions can be encapsulated within the aqueous interior and be delivered to cells in a biologically active form (Fraley, et al., Trends Biochem. Sci., 6: 77, 1981). In addition to mammalian cells, liposomes have been used for delivery of operatively encoding transgenes in plant, yeast and bacterial cells. In order for a liposome to be an efficient gene transfer vehicle, the following characteristics should be present: (1) encapsulation of the genes encoding the NsG33 at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6: 682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries.

Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted gene delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

A further example of a delivery system includes transplantation into the therapeutic area of a composition of packaging cells capable of producing vector particles as described in the present invention. Methods for encapsulation and transplantation of such cells are known in the art, in particular from WO 97/44065 (Cytotherapeutics). By selecting a packaging cell line capable of producing lentiviral particles, transduction of non-dividing cells in the therapeutic area is obtained. By using retroviral particles capable of transducing only dividing cells, transduction is restricted to de-novo differentiated cells in the therapeutic area.

VII. Dosing Requirements and Delivery Protocol for Gene Therapy

An important parameter is the dosage of NsG33 gene therapy vector to be delivered into the target tissue. For viral vectors, the concentration may be defined by the number of transducing units/ml. Optimally, for delivery using a viral expression vector, each unit dosage will comprise 2.5 to 25 µL of a composition, wherein the composition includes a viral expression vector in a pharmaceutically acceptable fluid and provides from $10^8$ up to $10^{10}$ NsG33 transducing units per ml.

Importantly, specific in vivo gene delivery sites are selected so as to cluster in an area of loss, damage, or dysfunction of neural cells, glial cells, retinal cells, sensory cells, or stem cells. Such areas may be identified clinically using a number of known techniques, including magnetic resonance imaging (MRI) and biopsy. In humans, non-invasive, in vivo imaging methods such as MRI will be preferred. Once areas of neuronal loss are identified, delivery sites are selected for stereotaxic distribution so each unit dosage of NsG33 is delivered into the brain at, or within 500 µm from, a targeted cell, and no more than about 10 mm from another delivery site.

Within a given target site, the vector system may transduce a target cell. The target cell may be a cell found in nervous tissue, such as a neuron, astrocyte, oligodendrocyte, microglia, stem cells, neural precursor cells, or ependymal cell.

The vector system is preferably administered by direct injection. Methods for injection into the brain are well known in the art (Bilang-Bleuel et al (1997) Proc. Acad. Natl. Sci. USA 94:8818-8823; Choi-Lundberg et al (1998) Exp. Neurol. 154:261-275; Choi-Lundberg et al (1997) Science 275:838-841; and Mandel et al (1997)) Proc. Acad. Natl. Sci. USA 94:14083-14088). Stereotaxic injections may be given.

As mentioned above, for transduction in tissues such as the brain, it is necessary to use very small volumes, so the viral preparation is concentrated by ultracentrifugation. The resulting preparation should have at least $10^8$ t.u./ml, preferably from $10^8$ to $10^{10}$ t.u./ml, more preferably at least $10^9$ t.u./ml. (The titer is expressed in transducing units per ml (t.u./ml) as described in example 6). It has been found that improved dispersion of transgene expression can be obtained by increasing the number of injection sites and decreasing the rate of injection (Horellou and Mallet (1997) as above). Usually between 1 and 10 injection sites are used, more commonly between 2 and 6. For a dose comprising 1-5×$10^9$ t.u./ml, the rate of injection is commonly between 0.1 and 10 µl/min, usually about 1 µl/min.

The virus composition is delivered to each delivery cell site in the target tissue by microinjection, infusion, scrape loading, electroporation or other means suitable to directly deliver the composition directly into the delivery site tissue through a surgical incision. The delivery is accomplished slowly, such as over a period of about 5-10 minutes (depending on the total volume of virus composition to be delivered).

VIII. Viral Vectors

Broadly, gene therapy seeks to transfer new genetic material to the cells of a patient with resulting therapeutic benefit to the patient. Such benefits include treatment or prophylaxis of a broad range of diseases, disorders and other conditions.

Ex vivo gene therapy approaches involve modification of isolated cells (including but not limited to stem cells, neural and glial precursor cells, and foetal stem cells), which are then infused, grafted or otherwise transplanted into the patient. See, e.g., U.S. Pat. Nos. 4,868,116, 5,399,346 and 5,460,959. In vivo gene therapy seeks to directly target host patient tissue in vivo.

Viruses useful as gene transfer vectors include papovavirus, adenovirus, vaccinia virus, adeno-associated virus, herpesvirus, and retroviruses. Suitable retroviruses include the group consisting of HIV, SIV, FIV, EIAV, MoMLV. A further group of suitable retroviruses includes the group consisting of HIV, SIV, FIV, EAIV, CIV. Another group of preferred virus vectors includes the group consisting of alphavirus, adenovirus, adeno associated virus, baculovirus, HSV, coronavirus, Bovine papilloma virus, Mo-MLV, preferably adeno associated virus.

Preferred viruses for treatment of disorders of the nervous system are lentiviruses and adeno-associated viruses. Both types of viruses can integrate into the genome without cell divisions, and both types have been tested in pre-clinical animal studies for indications of the nervous system, in particular the central nervous system.

Methods for preparation of AAV are described in the art, e.g. U.S. Pat. No. 5,677,158. U.S. Pat. No. 6,309,634 and U.S. Pat. No. 6,683,058 describe examples of delivery of AAV to the central nervous system.

Preferably, a lentivirus vector is a replication-defective lentivirus particle. Such a lentivirus particle can be produced from a lentiviral vector comprising a 5' lentiviral LTR, a tRNA binding site, a packaging signal, a promoter operably linked to a polynucleotide signal encoding said fusion protein, an origin of second strand DNA synthesis and a 3' lentiviral LTR. Methods for preparation and in vivo administration of lentivirus to neural cells are described in US 20020037281 (Methods for transducing neural cells using lentiviral vectors).

Retroviral vectors are the vectors most commonly used in human clinical trials, since they carry 7-8 kb and since they have the ability to infect cells and have their genetic material stably integrated into the host cell with high efficiency. See, e.g., WO 95/30761; WO 95/24929. Oncovirinae require at least one round of target cell proliferation for transfer and integration of exogenous nucleic acid sequences into the patient. Retroviral vectors integrate randomly into the patient's genome. Retroviruses can be used to target stem cells of the nervous system as very few cell divisions take place in other cells of the nervous system (in particular the CNS).

Three classes of retroviral particles have been described; ecotropic, which can infect murine cells efficiently, and amphotropic, which can infect cells of many species. The third class includes xenotrophic retrovirus which can infect cells of another species than the species which produced the virus. Their ability to integrate only into the genome of dividing cells has made retroviruses attractive for marking cell lineages in developmental studies and for delivering therapeutic or suicide genes to cancers or tumors.

For use in human patients, the retroviral vectors must be replication defective. This prevents further generation of infectious retroviral particles in the target tissue—instead the replication defective vector becomes a "captive" transgene stable incorporated into the target cell genome. Typically in replication defective vectors, the gag, env, and pol genes have been deleted (along with most of the rest of the viral genome). Heterologous DNA is inserted in place of the deleted viral genes. The heterologous genes may be under the control of the endogenous heterologous promoter, another heterologous promoter active in the target cell, or the retroviral 5' LTR (the viral LTR is active in diverse tissues). Typically, retroviral vectors have a transgene capacity of about 7-8 kb.

Replication defective retroviral vectors require provision of the viral proteins necessary for replication and assembly in trans, from, e.g., engineered packaging cell lines. It is important that the packaging cells do not release replication competent virus and/or helper virus. This has been achieved by expressing viral proteins from RNAs lacking the ψ signal, and expressing the gag/pol genes and the env gene from separate transcriptional units. In addition, in some 2. and 3. generation retroviruses, the 5' LTR's have been replaced with non-viral promoters controlling the expression of these genes, and the 3' promoter has been minimised to contain only the proximal promoter. These designs minimize the possibility of recombination leading to production of replication competent vectors, or helper viruses.

IX. Expression Vectors

Construction of vectors for recombinant expression of NsG33 polypeptides for use in the invention may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory, (NY 1982). Expression vectors may be used for generating producer cells for recombinant production of NsG33 polypeptides for medical use, and for generating therapeutic cells secreting NsG33 polypeptides for naked or encapsulated therapy.

Briefly, construction of recombinant expression vectors employs standard ligation techniques. For analysis to confirm correct sequences in vectors constructed, the genes are sequenced using, for example, the method of Messing, et al., (Nucleic Acids Res., 9: 309-, 1981), the method of Maxam, et al., (Methods in Enzymology, 65: 499, 1980), or other suitable methods which will be known to those skilled in the art.

Size separation of cleaved fragments is performed using conventional gel electrophoresis as described, for example, by Maniatis, et al., (Molecular Cloning, pp. 133-134, 1982).

For generation of efficient expression vectors, these should contain regulatory sequences necessary for expression of the encoded gene in the correct reading frame. Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many genes consists of the promoter and in some cases enhancer or regulator elements (Banerji et al., Cell 27: 299 (1981); Corden et al., Science 209: 1406 (1980); and Breathnach and Chambon, Ann. Rev. Biochem. 50: 349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11: 1855 (1983); Capecchi et al., In: Enhancer and eukaryotic gene expression, Gulzman and Shenk, eds., pp. 101-102, Cold Spring Harbor Laboratories (NY 1991). Other potent promoters include those derived from cytomegalovirus (CMV) and other wild-type viral promoters.

Promoter and enhancer regions of a number of non-viral promoters have also been described (Schmidt et al., Nature 314: 285 (1985); Rossi and deCrombrugghe, Proc. Natl. Acad. Sci. USA 84: 5590-5594 (1987)). Methods for maintaining and increasing expression of transgenes in quiescent cells include the use of promoters including collagen type I (1 and 2) (Prockop and Kivirikko, N. Eng. J. Med. 311: 376 (1984); Smith and Niles, Biochem. 19: 1820 (1980); de Wet et al., J. Biol. Chem., 258: 14385 (1983)), SV40 and LTR promoters.

According to one embodiment of the invention, the promoter is a constitutive promoter selected from the group consisting of: ubiquitin promoter, CMV promoter, JeT promoter (U.S. Pat. No. 6,555,674), SV40 promoter, Elongation Factor 1 alpha promoter (EF1-alpha), RSV, Mo-MLV-LTR. Examples of inducible/repressible promoters include: Tet-On, Tet-Off, Rapamycin-inducible promoter, Mx1.

A group of preferred promoters include CMV, human UbiC, JeT, RSV, Tet-regulatable promoter, Mo-MLV-LTR, Mx1, and EF-1alpha.

In addition to using viral and non-viral promoters to drive transgene expression, an enhancer sequence may be used to increase the level of transgene expression. Enhancers can increase the transcriptional activity not only of their native gene but also of some foreign genes (Armelor, Proc. Natl. Acad. Sci. USA 70: 2702 (1973)). For example, in the present invention collagen enhancer sequences may be used with the collagen promoter 2 (I) to increase transgene expression. In addition, the enhancer element found in SV40 viruses may be used to increase transgene expression. This enhancer sequence consists of a 72 base pair repeat as described by Gruss et al., Proc. Natl. Acad. Sci. USA 78: 943 (1981); Benoist and Chambon, Nature 290: 304 (1981), and Fromm and Berg, J. Mol. Appl. Genetics, 1: 457 (1982), all of which are incorporated by reference herein. This repeat sequence can increase the transcription of many different viral and cellular genes when it is present in series with various promoters (Moreau et al., Nucleic Acids Res. 9: 6047 (1981).

Further expression enhancing sequences include but are not limited to Woodchuck hepatitis virus post-transcriptional regulation element, WPRE, SP163, CMV enhancer, and Chicken [beta]-globin insulator or other insulators.

Transgene expression may also be increased for long term stable expression using cytokines to modulate promoter activity. Several cytokines have been reported to modulate the expression of transgene from collagen 2 (I) and LTR promoters (Chua et al., connective Tissue Res., 25:161-170 (1990); Elias et al., Annals N.Y. Acad. Sci., 580: 233-244 (1990)); Seliger et al., J. Immunol. 141: 2138-2144 (1988) and Seliger et al., J. Virology 62: 619-621 (1988)). For example, transforming growth factor (TGF), interleukin (IL)-I, and interferon (INF) down regulate the expression of transgenes driven by various promoters such as LTR. Tumor necrosis factor (TNF) and TGF 1 up regulate, and may be used to control, expression of transgenes driven by a promoter. Other cytokines that may prove useful include basic fibroblast growth factor (bFGF) and epidermal growth factor (EGF).

Collagen promoter with the collagen enhancer sequence (Coll (E)) may also be used to increase transgene expression by suppressing further any immune response to the vector which may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which downregulates LTR promoter and Coll (E) promoter-enhancer, and reduces transgene expression.

The vector may comprise further sequences such as a sequence coding for the Cre-recombinase protein, and LoxP sequences. A further way of ensuring temporary expression of the NsG33 is through the use of the Cre-LoxP system which results in the excision of part of the inserted DNA sequence either upon administration of Cre-recombinase to the cells (Daewoong et al, Nature Biotechnology 19:929-933) or by incorporating a gene coding for the recombinase into the virus construct (Plück, Int J Exp Path, 77:269-278). Incorporating a gene for the recombinase in the virus construct together with the LoxP sites and a structural gene (an NsG33 in the present case) often results in expression of the structural gene for a period of approximately five days.

X. Biocompatible Capsules

Encapsulated cell therapy is based on the concept of isolating cells from the recipient host's immune system by surrounding the cells with a semipermeable biocompatible material before implantation within the host. The invention includes a device in which cells capable of expressing and secreting NsG33 are encapsulated in an immunoisolatory capsule. An "immunoisolatory capsule" means that the capsule, upon implantation into a recipient host, minimizes the deleterious effects of the host's immune system on the cells in the core of the device. Cells are immunoisolated from the host by enclosing them within implantable polymeric capsules formed by a microporous membrane. This approach prevents the cell-to cell contact between host and implanted tissues, eliminating antigen recognition through direct presentation. The membranes used can also be tailored to control the diffusion of molecules, such as antibody and complement, based on their molecular weight (Lysaght et al., 56 J. Cell Biochem. 196 (1996), Colton, 14 Trends Biotechnol. 158 (1996)). Using encapsulation techniques cells can be transplanted into a host without immune rejection, either with or without use of immunosuppressive drugs. Useful biocompatible polymer capsules usually contain a core that contains cells, either suspended in a liquid medium or immobilized within an immobilizing matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated cells from immune destruction. The semipermeable nature of the capsule membrane also permits the biologically active molecule of interest to easily diffuse from the capsule into the surrounding host tissue.

The capsule can be made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors such as NsG33 polypeptides, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics. Preferably the capsule of this invention will be similar to those described in WO 92/19195 or WO 95/05452, incorporated by reference; or U.S. Pat. Nos. 5,639,275; 5,653,975; 4,892,538; 5,156,844; 5,283,187; or U.S. Pat. No. 5,550,050, incorporated by reference. Such capsules allow for the passage of metabolites, nutrients and therapeutic substances while minimizing the detrimental effects of the host immune system. Components of the biocompatible material may include a surrounding semipermeable membrane and the internal cell-supporting scaffolding. Preferably, the genetically altered cells are seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene teraphthalate, nylon, polyamides, polyurethanes, polybutester, silk, cotton, chitin, carbon, or biocompatible metals. Also, bonded fiber structures can be used for cell implantation (U.S. Pat. No.

5,512,600, incorporated by reference). Biodegradable polymers include those comprised of poly(lactic acid) PLA, poly(lactic-coglycolic acid) PLGA, and poly(glycolic acid) PGA and their equivalents. Foam scaffolds have been used to provide surfaces onto which transplanted cells may adhere (WO 98/05304, incorporated by reference). Woven mesh tubes have been used as vascular grafts (WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fiber membrane. Such membranes, and methods of making them are disclosed by U.S. Pat. Nos. 5,284,761 and 5,158,881, incorporated by reference. The surrounding semipermeable membrane is formed from a polyether sulfone hollow fiber, such as those described by U.S. Pat. No. 4,976,859 or U.S. Pat. No. 4,968,733, incorporated by reference. An alternate surrounding semipermeable membrane material is poly(acrylonitrile/covinyl chloride).

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired.

When macrocapsules are used, preferably between $10^3$ and $10^8$ cells are encapsulated, most preferably $10^5$ to $10^7$ cells are encapsulated in each device. Dosage may be controlled by implanting a fewer or greater number of capsules, preferably between 1 and 10 capsules per patient.

The scaffolding may be coated with extracellular matrix (ECM) molecules. Suitable examples of extracellular matrix molecules include, for example, collagen, laminin, and fibronectin. The surface of the scaffolding may also be modified by treating with plasma irradiation to impart charge to enhance adhesion of cells.

Any suitable method of sealing the capsules may be used, including the use of polymer adhesives or crimping, knotting and heat sealing. In addition, any suitable "dry" sealing method can also be used, as described, e.g., in U.S. Pat. No. 5,653,687, incorporated by reference.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148, incorporated by reference), and the aqueous and vitreous humors of the eye (see, WO 97/34586, incorporated by reference).

Methods and apparatus for implantation of capsules into the CNS are described in U.S. Pat. No. 5,487,739. Methods and apparatus for implantation of capsules into the eye are described in U.S. Pat. No. 5,904,144, U.S. Pat. No. 6,299,895, U.S. Pat. No. 6,439,427, and US 20030031700.

In one aspect the invention relates to a biocompatible capsule comprising: a core comprising living packaging cells that secrete a viral vector for infection of a target cell, wherein the viral vector is a vector according to the invention; and an external jacket surrounding said core, said jacket comprising a permeable biocompatible material, said material having a porosity selected to permit passage of retroviral vectors of approximately 100 mm diameter thereacross, permitting release of said viral vector from said capsule.

Preferably, the core additionally comprises a matrix, the packaging cells being immobilized by the matrix. According to one embodiment, the jacket comprises a hydrogel or thermoplastic material.

Examples of suitable cells for packaging cell lines include HEK293, NIH3T3, PG13, and ARPE-19 cells. Preferred cells include PG13 and 3T3 cells.

Packaging cell lines may be encapsulated and administered using the methods and compositions disclosed in U.S. Pat. No. 6,027,721 and WO 97/01357 hereby incorporated by reference in their entirety.

XI Support Matrix for NsG33 Producing Cells

The present invention further comprises culturing NsG33 producing cells in vitro on a support matrix prior to implantation into the mammalian nervous system. The preadhesion of cells to microcarriers prior to implantation is designed to enhance the long-term viability of the transplanted cells and provide long term functional benefit.

To increase the long term viability of the transplanted cells, i.e., transplanted NsG33 secreting cells, the cells to be transplanted can be attached in vitro to a support matrix prior to transplantation. Materials of which the support matrix can be comprised include those materials to which cells adhere following in vitro incubation, and on which cells can grow, and which can be implanted into the mammalian body without producing a toxic reaction, or an inflammatory reaction which would destroy the implanted cells or otherwise interfere with their biological or therapeutic activity. Such materials may be synthetic or natural chemical substances, or substances having a biological origin.

The matrix materials include, but are not limited to, glass and other silicon oxides, polystyrene, polypropylene, polyethylene, polyvinylidene fluoride, polyurethane, polyalginate, polysulphone, polyvinyl alcohol, acrylonitrile polymers, polyacrylamide, polycarbonate, polypentent, nylon, amylases, natural and modified gelatin and natural and codified collagen, natural and modified polysaccharides, including dextrans and celluloses (e.g., nitrocellulose), agar, and magnetite. Either resorbable or non-resorbable materials may be used. Also intended are extracellular matrix materials, which are well-known in the art. Extracellular matrix materials may be obtained commercially or prepared by growing cells which secrete such a matrix, removing the secreting cells, and allowing the cells which are to be transplanted to interact with and adhere to the matrix. The matrix material on which the cells to be implanted grow, or with which the cells are mixed, may be an indigenous product of RPE cells. Thus, for example, the matrix material may be extracellular matrix or basement membrane material, which is produced and secreted by RPE cells to be implanted.

To improve cell adhesion, survival and function, the solid matrix may optionally be coated on its external surface with factors known in the art to promote cell adhesion, growth or survival. Such factors include cell adhesion molecules, extracellular matrix, such as, for example, fibronectin, laminin, collagen, elastin, glycosaminoglycans, or proteoglycans or growth factors.

Alternatively, if the solid matrix to which the implanted cells are attached is constructed of porous material, the growth- or survival promoting factor or factors may be incorporated into the matrix material, from which they would be slowly released after implantation in vivo.

When attached to the support according to the present invention, the cells used for transplantation are generally on the "outer surface" of the support. The support may be solid or porous. However, even in a porous support, the cells are in direct contact with the external milieu without an intervening membrane or other barrier. Thus, according to the present invention, the cells are considered to be on the "outer surface" of the support even though the surface to which they adhere may be in the form of internal folds or convolutions of the porous support material which are not at the exterior of the particle or bead itself.

The configuration of the support is preferably spherical, as in a bead, but may be cylindrical, elliptical, a flat sheet or strip, a needle or pin shape, and the like. A preferred form of support matrix is a glass bead. Another preferred bead is a polystyrene bead.

Bead sizes may range from about 10 μm to 1 mm in diameter, preferably from about 90 μm to about 150 μm. For a description of various microcarrier beads, see, for example, Fisher Biotech Source 87-88, Fisher Scientific Co., 1987, pp. 72-75; Sigma Cell Culture Catalog, Sigma Chemical Co., St. Louis, 1991, pp. 162-163; Ventrex Product Catalog, Ventrex Laboratories, 1989; these references are hereby incorporated by reference. The upper limit of the bead's size may be dictated by the bead's stimulation of undesired host reactions, which may interfere with the function of the transplanted cells or cause damage to the surrounding tissue. The upper limit of the bead's size may also be dictated by the method of administration. Such limitations are readily determinable by one of skill in the art.

XII. Host Cells

In one aspect the invention relates to isolated host cells genetically modified with the vector according to the invention.

According to one embodiment, the host cells are prokaryotic cells such as *E. coli* which are capable producing recombinant protein in high quantities and which can easily be scaled up to industrial scale. The use of prokaryotic producer cells may require refolding and glycosylation of the NsG33 in order to obtain a biologically active protein. In another embodiment, the host cells are eukaryotic producer cells from non-mammals, including but not limited to known producer cells such as yeast (*Saccharomyces cerevisiae*), filamentous fungi such as *aspergillus*, and insect cells, such as Sf9

According to another embodiment, the cells preferably are mammalian host cells because these are capable of secreting and processing the encoded NsG33 correctly. Preferred species include the group consisting of human, feline, porcine, simian, canina, murine, rat, rabbit, mouse, and hamster.

Examples of primary cultures and cell lines that are good candidates for transduction or transfection with the vectors of the present invention include the group consisting of CHO, CHO-K1, HEI193T, HEK293, COS, PC12, HiB5, RN33b, neuronal cells, foetal cells, ARPE-19, C2C12, HeLa, HepG2, striatal cells, neurons, astrocytes, and interneurons. Preferred cell lines for mammalian recombinant production include CHO, CHO-1, HEI193T, HEK293, COS, PC12, HiB5, RN33b, and BHK cells.

For ex vivo gene therapy, the preferred group of cells include neuronal cells, neuronal precursor cells, neuronal progenitor cells, stem cells and foetal cells.

The invention also relates to cells suitable for biodelivery of NsG33 via naked or encapsulated cells, which are genetically modified to overexpress NsG33, and which can be transplanted to the patient to deliver bioactive NsG33 polypeptide locally. Such cells may broadly be referred to as therapeutic cells.

In a preferred embodiment of the invention, a therapeutic cell line has not been immortalised with the insertion of a heterologous immortalisation gene. As the invention relates to cells which are particularly suited for cell transplantation, whether as naked cells or—preferably as encapsulated cells, such immortalised cell lines are less preferred as there is an inherent risk that they start proliferating in an uncontrolled manner inside the human body and potentially form tumours.

Preferably, the cell line is a contact inhibited cell line. By a contact inhibited cell line is intended a cell line which when grown in 2-D cultures grow to confluency and then substantially stop dividing. This does not exclude the possibility that a limited number of cells escape the 2D layer. Contact inhibited cells may also be grown in 3D, e.g. inside a capsule. Also inside the capsules, the cells grow to confluency and then significantly slow down proliferation rate or completely stop dividing. A particularly preferred type of cells include epithelial cells which are by their nature contact-inhibited and which form stable monolayers in culture.

Even more preferred are retinal pigment epithelial cells (RPE cells). The source of RPE cells is by primary cell isolation from the mammalian retina. Protocols for harvesting RPE cells are well-defined (Li and Turner, 1988, Exp. Eye Res. 47:911-917; Lopez et al., 1989, Invest. Ophthalmol. Vis. Sci. 30:586-588) and considered a routine methodology. In most of the published reports of RPE cell cotransplantation, cells are derived from the rat (Li and Turner, 1988; Lopez et al., 1989). According to the present invention RPE cells are derived from humans. In addition to isolated primary RPE cells, cultured human RPE cell lines may be used in the practice of the invention.

For encapsulation, the cells need to be able to survive and maintain a functional NsG33 secretion at the low oxygen tension levels of the CNS. Preferably the cell line of the invention is capable of surviving at an oxygen tension below 5%, more preferably below 2%, more preferably below 1%. 1% oxygen tension corresponds approximately to the oxygen level in the brain.

To be a platform cell line for an encapsulated cell based delivery system, the cell line should have as many of the following characteristics as possible: (1) The cells should be hardy under stringent conditions (the encapsulated cells should be functional in the vascular and avascular tissue cavities such as in the central nervous system intraparenchymally or within the ventricular or intrathecal fluid spaces or the eye, especially in the intra-ocular environment). (2) The cells should be able to be genetically modified to express NsG33. (3) The cells should have a relatively long life span (the cells should produce sufficient progenies to be banked, characterised, engineered, safety tested and clinical lot manufactured). (4) The cells must be of human origin (which increases compatibility between the encapsulated cells and the host). (5) The cells should exhibit greater than 80% viability for a period of more than one month in vivo in device (which ensures long-term delivery). (6) The encapsulated cells should deliver an efficacious quantity of NsG33 (which ensures effectiveness of the treatment). (7) when encapsulated the cells should not cause a significant host immune reaction (which ensures the longevity of the graft). (8) The cells should be non-tumourigenic (to provide added safety to the host, in case of device leakage).

For encapsulation the preferred cells include retinal pigmented epithelial cells, including ARPE-19 cells; human immortalised fibroblasts; and human immortalised astrocytes.

The ARPE-19 cell line is a superior platform cell line for encapsulated cell based delivery technology and is also useful for unencapsulated cell based delivery technology. The ARPE-19 cell line is hardy (i.e., the cell line is viable under stringent conditions, such as implantation in the central nervous system or the intra-ocular environment). ARPE-19 cells can be genetically modified to secrete a substance of therapeutic interest. ARPE-19 cells have a relatively long life span. ARPE-19 cells are of human origin. Furthermore, encapsulated ARPE-19 cells have good in vivo device viability. ARPE-19 cells can deliver an efficacious quantity of growth factor. ARPE-19 cells elicit a negligible host immune reaction. Moreover, ARPE-19 cells are non-tumorigenic. Methods for culture and encapsulation of ARPE-19 cells are described in U.S. Pat. No. 6,361,771.

In another embodiment the therapeutic cell line is selected from the group consisting of: human fibroblast cell lines, human astrocyte cell lines, human mesencephalic cell line, and human endothelial cell line, preferably immortalised with TERT, SV40T or vmyc.

The method for generating an immortalised human astrocyte cell lines has previously been described (Price T N, Burke J F, Mayne L V. A novel human astrocyte cell line (A735) with astrocyte-specific neurotransmitter function. In Vitro Cell Dev Biol Anim. 1999 May; 35(5):279-88.). This protocol may be used to generate astrocyte cell lines.

The following three modifications of that protocol are preferably made to generate additional human astrocyte cell lines.

Human foetal brain tissue dissected from 5-12 weeks old foetuses may be used instead of 12-16 weeks old tissue.

The immortalisation gene v-myc, or TERT (telomerase) may be used instead of the SV40 T antigen.

Retroviral gene transfer may be used instead of transfection with plasmids by the calcium phosphate precipitation technique.

XII Recombinant Production and Purification of NsG33 Polypeptides of the Invention The NsG33 polypeptides of the invention may be produced using state of the art prokaryotic or eukaryotic expression systems. Examplary methods are described in WO 93/22437 (Innogenetics), which is hereby incorporated by reference. Due to the structural similarity between NsG33 polypeptides and the polypeptides described in WO 93/22437 it is contemplated that NsG33 polypeptides can be produced using the production methods described in this publication. The protocols described in WO 93/22437 describe purification of a protein having a predicted molecular weight of 29 kDa. In the case of expression of NsG33 fragments, which may be considerably shorter due to possible propeptide cleavage, the protocols should be modified to take the difference in molecular weight into consideration.

These examples include expression in E. coli (Example 5 of WO 93/22437), expression in COS1 cells (Example 6 of WO 93/22437), expression in a baculovirus expression system (Example 7 of WO 93/22437), expression in a vaccinia virus system (Example 8 of WO 93/22437). Each of the referenced expression systems resulted in the expression of significant amounts of the polypeptides described in WO 93/22437.

Purification of NsG33 proteins may be performed using the purification method described in WO 93/22437. Briefly, conditioned medium of COS1 cells transfected with the cDNA of the invention is collected after 48 h and filtered over a 0.22 μm filter to remove cell debris. A typical purification starts from 600 to 1000 ml of COS1 transfection medium. To this $MgCl_2$ and dextrane-sulphate 500.000 (Pharmacia, Uppsala, Sweden) is added to a final concentration of 60 mM and 0.02%, respectively. After 1 h incubation at 4° C. the precipitate is pelleted by centrifugation (12.000 g, 30 min., 4° C.). The supernatant fraction, containing the NsG33 is dialysed against 50 mM Hepes pH 7.0, 4 mM EDTA, adjusted to pH 8.0 and loaded at a flowrate of 0.5 ml/minute on a 4 ml Phenylboronate agarose (PBA 30, Amicon, MA, USA) column equilibrated in 50 mM Hepes pH 8.5. The NsG33 is eluted from the matrix by 100 mM Sorbitol.

The Sorbitol eluated peak is then passed at a flowrate of 0.5 ml/minute over a 1 ml FPLC Mono Q anion exchange column (Pharmacia) equilibrated in Hepes pH 8.5 and eluted with a linear salt gradient of 0 to 1 M NaCl at a flowrate of 1 ml/minute.

The eluate is concentrated about 40 fold by Centricon 10.000 (Amicon) and loaded batchwise (3 times 0.25 ml) on a SMART Superdex 75 gel filtration column (Pharmacia) equilibrated against PBS. This protocol may result in elution of protein of high purity.

Other state of the art protein purification protocols may also be used to provide enough pure protein to perform the in vitro and in vivo assays described in the examples.

XIV. In Vitro Uses of NsG33

NsG33 polypeptides and/or NsG33 encoding polynucleotides may be used as growth factors or trophic factors in vitro. This use is based on the finding that NsG33 is a secreted protein with structural features of a growth factor or hormone and on the finding by the present inventors that NsG33 causes the generation and/or survival of neurons and/or proliferation of neural precursors in several in vitro assays. The neuroprotective and/or neurogenesis effect has been found in a neural precursor cell line (hNS1) and in a primary culture (rat striatal culture). In addition an antiapoptotic effect has been found in a cell line with neuronal potential (PC12).

NsG33 may be administered to the culture as a protein composition or the cells may be transduced or transfected with cDNA encoding NsG33. Whether NsG33 would be effective in the treatment of a particular cell type or tissues can be readily determined by one skilled in the art using any of a variety of assays known in the art. For example, with respect to providing trophic support for cells, trophic factors can produce beneficial biochemical and morphological effects and, under some circumstances, can promote cell survival. With respect to neurons, it is known in the art that depriving a neuron of trophic support may result in a decrease in metabolic activity, i.e., glucose uptake, RNA synthesis and protein synthesis, required for normal function and growth. Deckwerth and Johnson, J. Cell Biol. 123:1207-1222, 1993. Removal of trophic support also may result in a reduction in size of the cell body of the neuron.

Presumably as a consequence of the loss of the metabolic effects of trophic factors, trophic factor deprivation may result in a decrease or cessation of process outgrowth and may result in retraction of neuronal processes. In addition to the requirement of trophic factor for these aspects of neuronal biology, the neuron may require the neurotrophic factor to maintain survival; thus, survival assays are a frequently used means to detect or quantitate the actions of a neurotrophic factor. However, trophic support can also be manifest as morphological, biochemical, and functional changes; independent of neuronal number or any effect on survival.

EXAMPLES

Example 1, NsG33 Sequences

SEQ ID NO 1, human NsG33 genomic sequence with 100 extra base pairs added in the ends of 5' and 3'.
SEQ ID NO 2, human NsG33 cDNA
SEQ ID NO 3, human NsG33 full length amino acid sequence
SEQ ID NO 4, human NsG33 protein without signal peptide
SEQ ID NO 5, human NsG33 C-terminal polypeptide
SEQ ID NO 6, mouse NsG33 genomic sequence with 100 extra base pairs added in the ends of 5' and 3'.
SEQ ID NO 7, mouse NsG33 partial cDNA
SEQ ID NO 8, mouse NsG33 partial amino acid sequence
SEQ ID NO 9, mouse NsG33 protein without signal peptide
SEQ ID NO 10, mouse NsG33 C-terminal polypeptide
SEQ ID NO 11, rat NsG33 genomic sequence with 100 extra base pairs added in the ends of 5' and 3'.
SEQ ID NO 12, rat NsG33 cDNA
SEQ ID NO 13, rat NsG33 full length amino acid sequence
SEQ ID NO 14, rat NsG33, protein without signal peptide
SEQ ID NO 15, rat NsG33, C-terminal polypeptide
SEQ ID No 16, nucleotide sequence encoding human C-terminal peptide NsG33
SEQ ID No 17, nucleotide sequence encoding mouse C-terminal peptide NsG33
SEQ ID No 18, nucleotide sequence encoding rat C-terminal peptide NsG33
SEQ ID No 19, human N-terminal peptide
SEQ ID No 20, mouse N-terminal peptide
SEQ ID No 21, rat N-terminal peptide
SEQ ID No 22, human N-terminal peptide
SEQ ID No 23, mouse N-terminal peptide
SEQ ID No 24, rat N-terminal peptide
SEQ ID No 25, mouse cDNA
SEQ ID No 26, mouse full length amino acid sequence In the sequence listing, introns are marked in lowercase and exons in UPPERCASE. In the polypeptide sequences, signal peptides are marked in bold.

```
Human NsG33 genomic nucleotide sequence
(SEQ ID NO 1)
actggccgac acgccgcagg ccccgccccc ttcccgaccc        0050
gctccaaggc ggccccggcg ctggggctgc gcggcaggcg gagcggccgc        0100
gggcttgggg

GCTTCGCCGG GGCCGGGCGG CCGGCGCCCC CGGCTGCTCC        0150
CGCCGCCGCC

CGGACCCGCG CCCCGCCGGG GCAGCGGTGG TGAGAGCCCC        0200
GACTCCCCGG

ACGCCGCCCG CCGTGCCATG GGGTTCCCGG CCGCGGCGCT        0250
GCTCTGCGCG

CTGTGCTGCG GCCTCCTGGC CCCGGCTGCC CGCGCCGGCT        0300
ACTCCGAGGA

GCGCTGCAGC TGGAGGGGCA Ggtacggtcc gggggctgt         0350
ccccgcactt aggacggggt gcgctgcggc taggacccccc caggcgcccc       0400
tcggagcgcg cagagcgctg ggccggtttc cccatccgcg aggcggcctc        0450
gggagggagc gggggctgcg ccgggcgggg acccgccccc gtctcagcgc        0500
cccgtcccgt cctgtcccca gCGGCCTCAC CCAGGAGCCC GGCAGCGTGG        0550
GGCAGCTGGC

CCTGGCCTGT GCGGAGGGCG CGGTTGAGTG GCTGTACCCG        0600
GCTGGGGCGC

TGCGCCTGAC CCTGGGCGGC CCCGATCCCA GAGCGCGGCC        0650
CGGCATCGCC

TGTCTGCGGC CGGTGCGGCC CTTCGCGGGC GCCCAGGTCT        0700
TCGCGGAGCG

CGCAGGGGGC GCCCTGGAGC TGCTGCTGGC CGAGGGCCCG        0750
GGCCCGGCAG

GGGGCCGCTG CGTGCGCTGG GGTCCCCGCA AGCGCCGGGC        0800
CCTCTTCCTG

CAGGCCACGC CGCACCAGGA CATCAGCCGC CGCGTGGCCG        0850
CCTTCCGCTT

TGAGCTGCGC GAGGACGGGC GCCCCGAGCT GCCCCCGCAG        0900
GCCCACGGTC

TCGGCGTAGA CGgtgagtgg cggtctggtt gggacagggt        0950
gggagtcccg aagtcttacc ctgcctgggc ttggcgggaa tgtgccttgt        1000
cggcccact gcagaaggaa aaagtgagct acaagggttg gatgggcttg        1050
tcaggccaca cagcctggga ctgctgggga gggatggcct ccccgccctc        1100
ccttcccgat tcatctctgg aaagagctgg caggggcaga gtggagggaa        1150
ggggaggccg ggcccagcaa tcctgggcct ctggtccctg aacggttggg        1200
ggaagagatg gtggggacag aatcgaagcc tccggccaaa gctgtccggg        1250
gctccctggc ccagcggtga cctctctccc ctcccccagc ccaaccaaca        1300
aaagtccagt gtgcagcccg gtcaccatgg agacgccgct cgcctccctg        1350
cagggcacca ggcccagctc ttgcttggct ctcctggagc ttggcgcctg        1400
accctgaaag ggatgggctc tcgctattct gccccctggc cctgggccag        1450
ggacccagcc
```

```
ccacccttcc tctgccccca cttcctatca ccctagctgg    1500
gctgctgctc ttcagacctc agatccggga aactagaggg gtcccagatg    1550
ctggggtgca tatgtcagat gggagtgcag gagggcggcc caggacagct    1600
gatcgctagg catgcccccc aggcccacgt ctgtgtgcat tcctgccttg    1650
gaggtacgcg cctgcaagtg tgtttcctga gtacaggtgt cgccgagggc    1700
gtgcacatct gctgtgtagc tctctgggac ccccaggtgc catcaggccc    1750
tgagcgtggg ctctgctcat ttgcctgctg cctcctgccg cttgtgcgga    1800
caagggacgg ggcctggggt gatgccggga gagggcaggg cctctcctca    1850
ccacccctc tgcatgccag GTGCCTGCAG GCCCTGCAGC GACGCTGAGC    1900
TGCTCCTGGC CGCATGCACC AGCGACTTCG gtgagtgtcc ccgccatggg    1950
gggagcctgg agcctgcctt cccctgaatg cctaccgcag ccacatgcct    2000
ccccacagTA

ATTCACGGGA TCATCCATGG GGTCACCCAT GACGTGGAGC    2050
TGCAGGAGTC

TGTCATCACT GTGGTGGCCG CCCGTGTCCT CCGCCAGACA    2100
CCGCCGCTGT

TCCAGGCGGG GCGATCCGGG GACCAGGGGC TGACCTCCAT    2150
TCGTACCCCA

CTGCGCTGTG GCGTCCACCC GGGCCCAGGC ACCTTCCTCT    2200
TCATGGGCTG

GAGCCGCTTT GGGGAGGCCC GGCTGGGCTG TGCCCCACGA    2250
TTCCAGGAGT

TCCGCCGTGC CTACGAGGCT GCCCGTGCTG CCCACCTCCA    2300
CCCCTGCGAG

GTGGCGCTGC ACTGAGGGGC TGGGTGCTGG GGAGGGGCTG    2350
GTAGGAGGGA

GGGTGGGCCC ACTGCTTTGG AGGTGATGGG ACTATCAATA    2400
AGAACTCTGT

TCACGCAAgc tgctgtggac ctggtctcct gtgtccagcc    2450
cagccttggg cctgcctcgc agctgtgagg atggctccaa ttcctgcctc    2500
ctggcgggag actgaggc Human NsG33 (1109 bp; CDS = 118-999) (SEQ ID NO 2)
>gi|34147349|ref|NM_024042.2|Homo sapiens
hypothetical protein MGC2601 (MGC2601), mRNA
GCTTCGCCGGGGCCGGGCGGCCGGCGCCCCGGCTGCTCCCGCCGCCGCC

CGGACCCGCGCCCCGCCGGGGCAGCGGTGGTGAGAGCCCCGACTCCCCGG

ACGCCGCCCGCCGTGCCATGGGGTTCCCGGCCGCGGCGCTGCTCTGCGCG

CTGTGCTGCGGCCTCCTGGCCCCGGCTGCCCGCGCCGGCTACTCCGAGGA

GCGCTGCAGCTGGAGGGGCAGCGGCCTCACCCAGGAGCCCGGCAGCGTGG

GGCAGCTGGCCCTGGCCTGTGCGGAGGGCGCGGTTGAGTGGCTGTACCCG

GCTGGGGCGCTGCGCCTGACCCTGGGCGGCCCCGATCCCAGAGCGCGGCC

CGGCATCGCCTGTCTGCGGCCGGTGCGGCCCTTCGCGGGCGCCCAGGTCT

TCGCGGAGCGCGCAGGGGGCGCCCTGGAGCTGCTGCTGGCCGAGGGCCCG

GGCCCGGCAGGGGCCGCTGCGTGCGCTGGGGTCCCCGCGAGCGCCGGGC

CCTCTTCCTGCAGGCCACGCCGCACCAGGACATCAGCCGCCGCGTGGCCG

CCTTCCGCTTTGAGCTGCGCGAGGACGGGCGCCCCGAGCTGCCCCCGCAG

GCCCACGGTCTCGGCGTAGACGGTGCCTGCAGGCCCTGCAGCGACGCTGA

GCTGCTCCTGGCCGCATGCACCAGCGACTTCGTAATTCACGGGATCATCC

ATGGGGTCACCCATGACGTGGAGCTGCAGGAGTCTGTCATCACTGTGGTG

GCCGCCCGTGTCCTCCGCCAGACACCGCCGCTGTTCCAGGCGGGGCGATC

CGGGGACCAGGGGCTGACCTCCATTCGTACCCCACTGCGCTGTGGCGTCC

ACCCGGGCCCAGGCACCTTCCTCTTCATGGGCTGGAGCCGCTTTGGGGAG

GCCCGGCTGGGCTGTGCCCCACGATTCCAGGAGTTCCGCCGTGCCTACGA

GGCTGCCCGTGCTGCCCACCTCCACCCCTGCGAGGTGGCGCTGCACTGAG

GGGCTGGGTGCTGGGGAGGGGCTGGTAGGAGGGAGGGTGGGCCCACTGCT

TTGGAGGTGATGGGACTATCAAAGAACTCTGTTCACGCAAAAAAAAAAAA
AAAAAAAA

Nucleotide sequence encoding human NsG33 C-terminal
polypeptide (SEQ ID NO 16)
GCCCTCTTCCTGCAGGCCACGCCGCACCAGGACATCAGCCGCCGCGTGGC

CGCCTTCCGCTTTGAGCTGCGCGAGGACGGGCGCCCCGAGCTGCCCCCGC

AGGCCCACGGTCTCGGCGTAGACGGTGCCTGCAGGCCCTGCAGCGACGCT

GAGCTGCTCCTGGCCGCATGCACCAGCGACTTCGTAATTCACGGGATCAT

CCATGGGGTCACCCATGACGTGGAGCTGCAGGAGTCTGTCATCACTGTGG

TGGCCGCCCGTGTCCTCCGCCAGACACCGCCGCTGTTCCAGGCGGGGCGA

TCCGGGGACCAGGGGCTGACCTCCATTCGTACCCCACTGCGCTGTGGCGT

CCACCCGGGCCCAGGCACCTTCCTCTTCATGGGCTGGAGCCGCTTTGGGG

AGGCCCGGCTGGGCTGTGCCCCACGATTCCAGGAGTTCCGCCGTGCCTAC

GAGGCTGCCCGTGCTGCCCACCTCCACCCCTGCGAGGTGGCGCTGCAC

Human NsG33 full length amino acid sequence
(SEQ ID NO 3)
>IPI00031531.1 REFSEQ_NP:NP_076947 TREMBL:Q9UJH9
ENSEMBL:ENSP00000219542 Tax_Id = 9606 C380A1.2.1
(Novel protein)
MGFPAAALLC ALCCGLLAPA ARAGYSEERC SWRGSGLTQE

PGSVGQLALA CAEGAVEWLY PAGALRLTLG GPDPRARPGI

ACLRPVRPFA GAQVFAERAG GALELLLAEG PGPAGGRCVR

WGPRERRALF LQATPHQDIS RRVAAFRFEL REDGRPELPP

QAHGLGVDGA CRFCSDAELL LAACTSDFVI HGIIHGVTHD

VELQESVITV VAARVLRQTP PLFQAGRSGD QGLTSIRTPL

RCGVHPGPGT FLFMGWSRFG EARLGCAPRF QEFRRAYEAA

RAAHLPCEV ALH

Human NsG33, protein without signal peptide
(SEQ ID NO 4)
GYSEERCSWR GSGLTQEPGS VGQLALACAE GAVEWLYPAG

ALRLTLGGPD PRARPGIACL RPVRPFAGAQ VFAERAGGAL
```

-continued

ELLLLAEGPGP AGGRCVRWGP RERRALFLQA TPHQDISRRV

AAFRFELRED GRPELPPQAH GLGVDGACRP CSDAELLLAA

CTSDFVIHGI IHGVTHDVEL QESVITVVAA RVLRQTPPLF

QAGRSGDQGL TSIRTPLRCG VHPGPGTFLF MGWSRWGEAR

LGCAPRFQEF RRAYEAARAA HLHPCEVALH

Human NsG33, C-terminal polypeptide (SEQ ID NO 5)
ALFLQATPHQ DISRRVAAFR FELPEDGRPE LPPQAHGLGV

DGACRPCSDA ELLLAACTSD FVIHGIIHGV THDVELQESV

ITVVAARVLR QTPPLFQAGR SGDQGLTSIR TPLRCGVHPG

PGTFLFMGWS RFGEARLGCA PRFQEFRRAY EAARAAHLHP

CEVALH

Human N-terminal peptide (SEQ ID No 19)
GYSEERCSWR GSGLTQEPGS VGQLALACAE GAVEWLYPAG

ALRLTLGGPD PRARPGIACL RPVRPFAGAQ VEAERAGGAL

ELLLAEGPGP AGGRCVRWGP RERR

Human N-terminal peptide (SEQ ID No 22)
GYSEERCSWR GSGLTQEPGS VGQLALACAE GAVEWLYPAG

ALRLTLGGPD PRARPGIACL RPVRPFAGAQ VFAERAGGAL

ELLLAEGPGP AGGRCVR

Mouse NsG33 genomic nucleotide sequence
(SEQ ID NO 6)
Genomic chr17 (reverse strand):
nnnnnnnnnn nnnnnnnnnn nnnnnnnnnn nnnnnnnnnn    0050
nnnnnnnnnn nnnnnnnnnn nnnnnnnnnn nnnnnnnncc cctaaccatg    0100
ctggtagcca

CGCTTCTTTG CGCGCTCTGT TGCGGCCTCC TGGCCGCGTC    0150
CGCTCACGCT

GGCTACTCGG AAGACCGCTG CAGCTGGAGG GGCAGgtacc    0200
aggagggact gcggggaggg ttgtgggttt atttatttat ttattttatt    0250
ttatttactt cttgggttgg agggttccct cccacttgga actgaggaaa    0300
cgcagacttc aatgtcctgt tacacagagt agaagcagat gttggtagcc    0350
gcgggaaaag ggatgagcgg gctagggaac gagggtcacc cacctgagaa    0400
ccaccgtcct gtccccagCG GTTTCACCCA GGAGCCTGGC AGCGTGGGGC    0450
AGCTGACCCT

GGACTGTACT GAGGGCGCTA TCGAGTGGCT GTACCCAGCT    0500
GGGGCGCTGC

GCCTGACCCT GGGCGGCCCC GATCCGGGCA CACGGCCCAG    0550
CATCGTCTGT

CTGCGCCCAG AGCGGCCCTT CGCTGGTGCC CAGGTCTTCG    0600
CTGAACGTAT

GACCGGCAAT CTAGAGTTGC TACTGGCCGA GGGCCCGGAC    0650
CTGGCTGGGG

GCCGCTGCAT GCGCTGGGGT CCCCGCGAGC CGCGAGCCCT    0700
TTTCCTGCAG

GCCACACCAC ACCGCGACAT CAGCCGCAGA GTTGCTGCCT    0750
TCCGTTTTGA

ACTGCACGAG GACCAACGTG CAGAAATGTC TCCCCAGGCT    0800
CAAGGTCTTG

GTGTGGATGg tgagtgatta tgagactggc tgggtgtcag    0850
aaattggccc tccacactga cctgatggga ctgggccttg ccacccccatt    0900
gcatggagag tccttctgta gcttgacaga ggccactccg gtggagagca    0950
tagtggcttc caggtcgtaa ggaggtgagt tggaagtgcc cccgcctttc    1000
tctcctcctc ctcttaaaag attcggttta ggaaaagagc aggaggggggc    1050
aaatgcccga gaggccagcc ctgggtctct ggtttctgaa ggattggggg    1100
aagggttaag ctgaggcaga atcaaagcct atggccaagg ctgtccaggg    1150
ctccctggcc tggtggtgac ctccttcccc tccccccaag cccagccaac    1200
aaaagtccag tgtgcctctt cgtcaccatg gagactgcct gccctgcctc    1250
cctgcagggc accaggccca gtgctttgct cttctggaac ttgtagcctg    1300
accctgcagg gaatgaatgg ctctctgact gttctgccct agctagagac    1350
ccccccgaac tggagtccac tagaatatcc ctagctagag ctgggaggtc    1400
acagaacgtt tcccagtgtt agtctgagtt tatgagatgg taccaagcct    1450
gtgtatgagg cactgaggtg cccatcagta ggcatgtacc tgcagggtgt    1500
cttcaggcta taggatgctg ggagaagggt ttagtctctt gctcctgtac    1550
cttttcctct tgggaggagc tgtgggctcg tgctgagaga tcacaggcct    1600
ggctgatgac ctgccttgca tgctagGTGC CTGCAGGCCC TGCAGTGATG    1650
CCGAGCTCCT CCTGGCTGCA TGCACCAGTG ATTTTGgtga gtgtttctgt    1700
tgcgggagag cttagggtct gcctcacatt cccacgtgcc caccactggc    1750
caccatgtct cctcgtagTG ATCCACGGGA CCATCCATGG GGTCGCCCAT    1800
GACACAGAGC

TGCAAGAATC AGTCATCACT GTGGTGGTTG CTCGTGTCAT    1850
CCGCCAGACA

CTGCCACTGT TCAAGGAAGG GAGCTCGGAG GGCCAAGGCC    1900
GGGCCTCCAT

TCGTACCTTG CTGCGCTGTG GTGTGCGTCC TGGCCCAGGC    1950
TCCTTCCTCT

TCATGGGCTG GAGCCGATTT GGCGAAGCTT GGCTGGGCTG    2000
TGCTCCCCGC

TTCAAGAGT TCAGCCGTGT CTATTCAGCT GCTCTCACGA    2050
CCCATCTCAA

```
CCCATGTGAG ATGGCACTGG ACTGAGAGAC CTGGGAGCAA    2100
GCCCTGGATG

GACCTTCTTC TGGAGATGGG GTGTTGGGGA GGGTGATGGG    2150
AGGGTGGGTG

AGAAGGGTGT GGCTCGGATG GCATCCTGGT ACCCACAGTG    2200
AGCTGGTAGA

ATACTAAGTA ATCTGGACCA TAccagccac tgtagtcatg    2250
gtcttctgtg gcaggcagca tacccagctc tgtgcctgcc tcactttgtc    2300
tactctccag tctgctgccc ttctaaccct tc
```

Mouse NsG33 partial cDNA (1048 bp; CDS = <2-886)
(SEQ ID NO 7)
```
CCACGCGTCCGCCCACGCGTCGCGCGCTTCTTTGCGCGCTCTGTTGCGGCC
TCCTGGCCGCGTCCGCTCACGCTGGCTACTCGGAAGACCGCTGCAGCTGG
AGGGGCAGCGGTTTGACCCAGGAGCCTGGCAGCGTGGGGCAGCTGACCCT
GGACTGTACTGAGGGCGCTATCGAGTGGCTGTACCCAGCTGGGGCGCTGC
GCCTGACCCTGGGCGGCCCCGATCCGGGCACACGGCCCAGCATCGTCTGT
CTGCGCCCAGAGCGGCCCTTCGCTGGTGCCCAGGTCTTCGCTGAACGTAT
GACCGGCAATCTAGAGTTGCTACTGGCCGAGGGCCCGGACCTGGCTGGGG
GCCGCTGCATGCGCTGGGGTCCCCGCGAGCGCCGAGCCCTTTTCCTGCAG
GCCACACCACACCGCGACATCAGCCGCAGAGTTGCTGCCTTCCGTTTTGA
ACTGCACGAGGACCAACGTGCAGAAATGTCTCCCCAGGCTCAAGGTCTTG
GTGTGGATGGTGCCTGCACGCCCTGCACTGATGCCGAGCTCCTCCTGGCT
GCATGCACCAGTGATTTTGTGATCCACGGGACCATCCATGGGGTCGCCCA
TGACACAGAGCTGCAAGAATCAGTCATCACTGTGGTGGTTCCTCGTGTCA
TCCGCCAGACACTGCCACTGTTCAAGGAAGGGAGCTCGGAGGGCCAAGGC
CGGGCCTCCATTCGTACCTTGCTGCGCTGTGGTGTGCGTCCTGGCCCAGG
CTCCTTCCTCTTCATGGGCTGGAGCCGATTTGGCGAAGCTTGGCTGGGCT
GTGCTCCCCGCTTCCAAGAGTTCAGCCGTGTCTATTCAGCTGCTCTCACG
ACCCATCTCAACCCATGTGAGATGGCACTGGACTGAGAGACCTGGGAGCA
AGCCGTGGATGGACCTTCTTCTGGAGATGGGGTGTTGGGGAGGGTGATGG
GAGGGTGGGTGAGAAGGGTGTGGCTCGGATGGCATCCTGGTACCCACAGT
GAGCTGGTAGAATACTAGTAATCTGGACCATAAAAAAAAAAAAAAAAAA
```

Mouse NsG33 cDNA, 1363 bp, CDS 84 . . . 959
(SEQ ID NO 25)
NM_133719. *Mus musculus* meteorin. [gi:56550040]
```
gggcagccgc ccgcgggct gctcgcgctg cggccccgac
cctcccgggg cagcagtccg aggccccggc gcgtcccccta
accatgctgg tagccacgct tctttgcgcg ctctgttgcg
gcctcctggc cgcgtccgct cacgctggct actcggaaga
ccgctgcagc tggagggggca gcggtttgac ccaggagcct
ggcagcgtgg ggcagctgac cctggactgt actgagggcg
ctatcgagtg gctgtaccca gctggggcgc tgcgcctgac
cctgggcggc cccgatccgg gcacacggcc cagcatcgtc
tgtctgcgcc cagagcggcc cttcgctggt gcccaggtct
tcgctgaacg tatgaccggc aatctagagt tgctactggc
cgagggcccg gacctggctg ggggccgctg catgcgctgg
ggtccccgcg agcgccgagc ccttttcctg caggccacac
cacaccgcga catcagccgc agagttgctg ccttccgttt
tgaactgcac gaggaccaac gtgcagaaat gtctccccag
gctcaaggtc ttggtgtgga tggtgcctgc aggccctgca
gtgatgccga gctcctcctg gctgcatgca ccagtgattt
tgtgatccac gggaccatcc atggggtcgc ccatgacaca
gagctgcaag aatcagtcat cactgtggtg gttgctcgtg
tcatccgcca gacactgcca ctgttcaagg aagggagctc
ggagggccaa ggccgggcct ccattcgtac cttgctgcgc
tgtggtgtgc gtcctggccc aggctccttc ctcttcatgg
gctggagccg atttggcgaa gcttggctgg gctgtgctcc
ccgcttccaa gagttcagcc gtgtctattc agctgctctc
acgacccatc tcaacccatg tgagatggca ctggactgag
agacctggga gcaagccctg gatggacctt cttctggaga
tggggtgttg gggagggtga tgggagggtg ggtgagaagg
gtgtggctcg gatggcatcc tggtacccac agtgagctgg
tagaatacta gtaatctgga ccataccagc cactgtagt
catggtcttc tgtggcaggc agcatacccca gctctgtgcc
tgcctcactt tgtctactct ccagtctgct gcccttctaa
cccttcttag cctgctgacc agtgagctca tgttttcctc
gaattccagg gtgctgctgg ggttcagagc aaccgtgccg
tagtttggaa gacttgagct aattgttttt tttttgtttg
tttttttgtt tgtttaaagg tggcctgggg ggggcggcaa
aca
```

Nucleotide sequence encoding mouse C-terminal
polypeptide NsG33 (SEQ ID No 17)
```
GCCCTTTTCCTGCAGGCCACACCACACCGCGACATCAGCCGCAGAGTTGC
TGCCTTCCGTTTTGAACTGCACGAGGACCAACGTGCAGAAATGTCTCCCG
AGGCTCAAGGTCTTGGTGTGGATGGTGCCTGCAGGCCCTGCAGTGATGCC
GAGCTCCTCCTGGCTGCATGCACCAGTGATTTTGTGATCCACGGGACCAT
CCATGGGGTCGCCCATGACACAGAGCTGCAAGAATCAGTCATCACTGTGG
TGGTTGCTCGTGTCATCCGCCAGACACTGCCACTGTTCAAGGAAGGGAGC
TCGGAGGGCCAAGGCCGGGCCTCCATTCGTACCTTGCTGCGCTGTGGTGT
GCGTCCTGGCCCAGGCTCCTTCCTCTTCATGGGCTGGAGCCGATTTGGCG
AAGCTTGGCTGGGCTGTGCTCCCCGCTTCCAAGAGTTCAGCCGTGTCTAT
TCAGCTGCTCTCACGACCCATCTCAACCCATGTGAGATGGCACTGGAC
```

Mouse NsG33 partial NsG33 (SEQ ID NO 8), i.e.
missing N-terminal
>gi|23274274|gb|AAH37181.1|1810034B16Rik protein
[*Mus musculus*]
HASAHASALL CALCCGLLAA SAHAGYSEDR CSWRGSGLTQ

EPGSVGQLTL DCTEGAIEWL YPAGALRLTL GGPDPGTRPS

IVCLRPERPF AGAQVFAEPM TGNLELLLAE QFDLAGGRCM

RWGPPERRAL FLQATPHRDI SPRVAAFRFE LHEDQRAEMS

PQAQGLGVDG ACRPCSDAEL LLAACTSDFV IHGTIHGVAH

DTELQESVIT VVVARVIRQT LPLFKEGSSE GQGRASIRTL

LRCGVRPGPG SFLFMGWSRF GEAWLGCAPR FQEFSRVYSA

ALTTHLNPCE MALD

Mouse NsG33 full length amino acid sequence
(SEQ ID NO 26)
ref|NP_598480.1|meteorin [*Mus musculus*]
MLVATLLCAL CCGLLAASAH AGYSEDRCSW RGSGLTQEPG

SVGQLTLDCT EGAIEWLYPA GALRLTLGGP DPGTRPSIVC

LRPERPFAGA QVFAEPMTGN LELLLAEGPD LAGGRCNRWG

PREPRALFLQ ATPHRDISPR VAAFRFELHE DQRAEMSPQA

QGLGVDGACR PCSDAELLLA ACTSDFVIHG TIBGVAHDTE

LQESVITVVV ARVIRQTLPL FKEGSSEGQG RASIRTLLRC

GVRPGPGSFL FMGWSRFGEA WLGCAPRFQE FSRVYSAALT

THLNPCEMAL D

Mouse NsG33 protein without signal peptide
(SEQ ID NO 9)
GYSEDRCSWR GSGLTQEPGS VGQLTLDCTE GAIEWLYPAG

ALRLTLGGPD PGTRPSIVCL RPERPFAGAQ VFAERMTGNL

ELLLAEGPDL AGGRCMRWGP WEPRALFLQA TPHRDISWRV

AAFRFEZHED QRAEMSPQAQ GLGVDGACRP CSDAELLLAA

CTSDFVIHGT IHGVAHDTEZ QESVITVVVA RVIRQTLPLF

KEGSSEGQGR ASIRTLLRCG VRPGPGSFLF MGWSRFGEAW

LGCAPRFQEF SRVYSAALTT HLNPCEMALD

Mouse NsG33, C-terminal polypeptide
(SEQ ID No 10)
ALFLQATPHR DISRRVAAFR FELHEDQRAE MSPQAQGLGV

DGACRPCSDA ELLLAACTSD FVIHGTIHGV AHDTELQESV

ITVVVARVIR QTLPLFKEGS SEGQGRASIR TLLRCGVRPG

PGSFLFMGWS RFGEAWLGCA PRFQEFSRVY SAALTTHLNP

CEMALD

Mouse NsG33, N-terminal polypeptide (SEQ ID No 20)
GYSEDRCSWR GSGLTQEPGS VGQLTLDCTE GAIEWLYPAG

ALRLTLGGPD PGTRPSIVCL RPERPFAGAQ VFAERMTGWL

ELLLAEGPDL AGGRCMRWGP REER

Mouse NsG33, N-terminal polypeptide (SEQ ID No 23)
GYSEDRCSWR GSGLTQEPGS VGQLTLDCTE GATEWLYPAG

ALRLTLGGPD PGTRFSIVCL RPERPFAGAQ VFAERMTGNL

ELLLAEGPDL AGGRCMR

Rat NsG33 genomic sequence with 100 extra
basepairs added in the ends of 5' and 3' (SEQ
ID NO 11). Genomic chr10 (reverse strand):

```
tccccggttg tggggannnn nnnnnnnnnn      15064142
nnnnnnnnnn nnnnnnnnnn nnnnnnnnnn nnnnnnggca gcagcccgag      15064092
ccccggcgcg tccctaacc

ATGCTGGTAG CGGCGCTTCT CTGCGCGCTG      15064042
TGCTGCGGCC TCTTGGCTGC

GTCCGCTCGA GCTGGCTACT CCGAGGACCG      15063992
CTGCAGCTGG AGGGGCAGgt acccaggaga gattttgggg aggattttttg     15063942
ttatttgtgt tttaaattga aatcttgggt tggagggctc cctcccactt      15063892
ggaactgagg aagcgcagac ctcaatgtcc tgttccagag ggtggacgca      15063842
ggtgttggtg gccgcgggaa aagggttgag cgggctaggg aaatgagggc      15063792
cacccacctg agaaccaccg tcctgtcccc agCGGTTTGA CCCAGGAACC      15063742
TGGCAGCGTG GGGCAGCTGA

CCCTGGATTG TACTGAGGGT GCTATCGAGT      15063692
GGCTGTATCC AGCTGGGGCG

CTGCGCCTGA CTCTAGGCGG CTCTGATCCG      15063642
GGCACGCGGC CCAGCATCGT

CTGTCTGCGC CCAACACGGC CCTTCGCTGG      15063592
TGCCCAGGTC TTCGCTGAAC

GGATGGCCGG CAACCTAGAG TTGCTACTGG      15063542
CCGAGGGCCA AGGCCTGGCT

GGGGGCCGCT GCATGCGCTG GGGTCCTCGC      15063492
GAGCGCCGAG CCCTTTTCCT

GCAGGCCACG CCACACCGGG ACATCAGCCG      15063442
CAGAGTTGCT GCCTTCCAAT

TTGAACTGCA CGAGGACCAA CGTGCAGAAA      15063392
TGTCTCCCCA GGCCCAAGGT

TTTGGTGTCG ATGgtgagtg actagactgg      15063342
ctggggcgga gctgggtgtc agaaactggc cctctacact ggcctgatcc      15063292
gaatgggcct tgcctcccca ctgcaccgaa agccctgtag cttgacggag      15063242
gctactctgg tggagaacac agtggcttcc aggtcatagg gaggtgagtt      15063192
gagagttctc cctcctttct ctcctcctct tcaaggttcg gtttaggaaa      15063142
agagcgggag ggggcagatg ccagagaggc cagccttggg tctctggttt      15063092
ctgaagggtt gggggggaagg gttgggctgg ggcagaatca aagcctatgg     15063042
ccgaagctgt ccagggctcc ctggccttgt ggtgacctcc ttcccctccc      15062992
cctagcccaa ccaacaaaag tccagtgtgc ctcttcgtca ccatggagac      15062942
tgcctgccct gcctcccggc agggcaccag gcccagtgct ttgctcttct      15062892
ggaacttgtc tcctgaccct
```

```
gcagggaatg gctctctgac tgctctgcca         15062842
tagacagaga ccccagaagc agagtccact agaatatccc tggctggacc         15062792
tgggaggcag ctctgggagg ttacagaaag ttccccagtg ttggtctgag         15062742
tttctgagat gggtgtgcag gaatgtgtcc gaggcactga ggggcccatg         15062692
agtagtcttc aggcagtgtg atgctgggag aagggtttag tcgccagctc         15062642
ctgtaccttc tcctactgtg gggagctgtg ggcttgtgct gagagatcac         15062592
aggcctgcct gatgacctgc cttgcatgct agGTGCCTGC AGGCCCTGCA         15062542
GTGATGCCGA GCTCCTTCTG ACTGCATGCA CCAGTGACTT TGgtgagtgt         15062492
ttccgtcttg ggagagctta gggtctgccc cacattccca cgtgcccacc         15062442
actggccacc atgtctcttc gtagTGATCC ATGGGACCAT CCATGGGGTC         15062392
GTCCATGACA TGGAGCTGCA

AGAATCAGTC ATCACTGTGG TGGCCACTCG         15062342
TGTCATCCGC CAGACACTGC

CACTGTTCCA GGAAGGGAGC TCGGAGGGCC         15062292
GGGGCCAGGC CTCCGTTCGT

ACCTTGTTGC GCTGTGGTGT GCGTCCTGGC         15062242
CCAGGCTCCT TCCTCTTCAT

GGGCTGGAGC CGATTTGGCG AAGCTTGGCT         15062192
GGGCTGCGCT CCCCGCTTCC

AAGAGTTCAG CCGTGTCTAT TCAGCTGCTC         15062142
TCGCGGCCCA CCTCAACCCA

TGTGAGGTGG CACTGGACTG AGAGACCTGG         15062092
GAGCAAGCCC TGGATGGATC

TTCCTCTGGG GATGGGGTGT TGGGGAGGGG         15062042
TGATAGGAGG GTGGGTGGGA

AGGGTGTGGC TCAGATGGCA TCCTGGTACC         15061992
CACAGTGAGG TGGTAGAATA

CTAAATAACC TGGATCACAC Cagccactgt         15061942
agacatggtc ttctgtgaca ggcaggctca ctcagctctg ctcctgcctc         15061892
actttaccta ctctccagtc tgctgcccctt ctgacccttc t SEQ ID NO 12, rat NsG33 (1026 bp; CDS = 1-876)
>gi|34870570|ref|XM_213261.2|Rattus norvegicus
similar to 1810034B16Rik protein (LOC287151), mRNA
ATGCTGGTAGCGGCGCTTCTCTGCGCGCTGTGCTGCGGCCTCTTGGCTGC

GTCCGCTCGAGCTGGCTACTCCGAGGACCGCTGCAGCTGGAGGGGCAGCG

GTTTGACCCAGGAACCTGGCAGCGTGGGGCAGCTGACCCTGGATTGTACT

GAGGGTGCTATCGAGTGGCTGTATCCAGCTGGGGCGCTGCGCCTGACTCT

AGGCGGCTCTGATCCGGGCACGCGGCCCAGCATCGTCTGTCTGCGCCCAA

CACGGCCCTTCGCTGGTGCCCAGGTCTTCGCTGAACGGATGGCCGGCAAC

CTAGAGTTGCTACTGGCCGAGGGCCAAGGCCTGGCTGGGGGCCGCTGCAT

GCGCTGGGGTCCTCGCGAGCGCCGAGCCCTTTTCCTGCAGGCCACGCCAC
```

ACCGGGACATCAGCCGCAGAGTTGCTGCCTTCCAATTTGAACTGCACGAG

GACCAACGTGCAGAAATGTCTCCCCAGGCCCAAGGTTTTGGTGTGGATGG

TGCCTGCAGGCCCTGCAGTGATGCCGAGCTCCTTCTGACTGCATGCACCA

GTGACTTTGTGATCCATGGGACCATCCATGGGGTCGTCCATGACATGGAG

CTGCAAGAATCAGTCATCACTGTGGTGGCCACTCGTGTCATCCGCCAGAC

ACTGCCACTGTTCCAGGAAGGGAGCTCGGAGGGCCGGGGCCAGGCCTCCG

TTCGTACCTTGTTGCGCTGTGGTGTGCGTCCTGGCCCAGGCTCCTTCCTC

TTCATGGGCTGGAGCCGATTTGGCGAAGCTTGGCTGGGCTGCGCTCCCCG

CTTCCAAGAGTTCAGCCGTGTCTATTCAGCTGCTCTCGCGGCCCACCTCA

ACCCATGTGAGGTGGCACTGGACTGAGAGACCTGGGAGCAAGCCCTGGAT

GGATCTTCCTCTGGGGATGGGGTGTTGGGGAGGGGTGATAGGAGGGTGGG

TGGGAAGGGTGTGGCTCAGATGGCATCCTGGTACCCACAGTGAGGTGGTA

GAATACTAAATAACCTGGATCACACC

Rat C-terminal polypeptide NsG33 coding sequence
(SEQ ID NO 18)
GCCCTTTTCCTGCAGGCCACGCCACACCGGGACATCAGCCGCAGAGTTGC

TGCCTTCCAATTTGAACTGCACGAGGACCAACGTGCAGAAATGTCTCCCC

AGGCCCAAGGTTTTGGTGTGGATGGTGCCTGCAGGCCCTGCAGTGATGCC

GAGCTCCTTCTGACTGCATGCACCAGTGACTTTGTGATCCATGGGACCAT

CCATGGGGTCGTCCATGACATGGAGCTGCAAGAATCAGTCATCACTGTGG

TGGCCACTCGTGTCATCCGCCAGACACTGCCACTGTTCCAGGAAGGGAGC

TCGGAGGGCCGGGGCCAGGCCTCCGTTCGTACCTTGTTGCGCTGTGGTGT

GCGTCCTGGCCCAGGCTCCTTCCTCTTCATGGGCTGGAGCCGATTTGGCG

AAGCTTGGCTGGGCTGCGCTCCCCGCTTCCAAGAGTTCAGCCGTGTCTAT

TCAGCTGCTCTCGCGGCCCACCTCAACCCATGTGAGGTGGCACTGGAC

Rat NsG33 full length amino acid sequence
(SEQ ID NO 13)
>IPI00369281.1|REFSEQ_XP:XP_213261|
ENSEMBL:ENSRNOP00000026676
MLVAALLCAL CCGLLAASAR AGYSEDRCSW RGSGLTQEPG

SVGQLTLDCT EGAIEWLYPA GALRLTLGGS DPGTRPSIVC

LRPTRPFAGA QVFAERMAGN LELLLAEGQG LAGGPCMRWG

PPERRALFLQ ATPHRDISRR VAAFQFELHE DQPAEMSPQA

QGFGVDGACR PCSDAELLLT ACTSDFVIHG TIHGVVHDME

LQESVITVVA TRVIRQTLPL FQEGSSEGRG QASVRRLLRC

GVRPGPGSFL FMGWSRFGEA WLGCAPRFQE FSRVYSAALA

AELNPCEVAL D

Rat NsG33, protein without signal peptide
(SEQ ID No 14)
(ASARA)GYSED RCSWRGSGLT QEPGSVGQLT

LDCTEGAIEW LYPAGALRLT LGGSDPGTRP SIVCLRPTRP

FAGAQVFAER MAGNLELLLA EGQGLAGGRC MRWGPRERRA

LFLQATPHRD ISRRVAAFQF ELHEDQRAEM SPQAGFGVD

GACRPCSDAE LLLTACTSDF VIHGTIHGVV HDMELQESVI

```
                                                  -continued
TVVATRVIRQ TLPLFQEGSS EGRGQASVRT LLRCGVRPGP

GSFLFMGWSR FGEAWLGCAP RFQEFSRVYS AALAAHLNPC

EVALD

Rat NsG33, C-terminal polypeptide
(SEQ ID No 15)
ALFLQATPHR DISRRVAAFQ FELHEDQRAE MSPQAQGFGV

DGACRPCSDA ELLLTACTSD FVIHGTIHGV VHDMELQESV

ITVVATRVIR QTLPLFQEGS SEGRGQASVR TLLRCGVRPG

PGSFLFMGWS RFGEAWLGCA PRFQEFSRVY SAALAAHLWP

CEVALD

Rat NsG33, N-terminal polypeptide
(SEQ ID No 21)
(ASARA)GYSED RCSWRGSGLT QEPGSVGQLT LDCTEGAIEW

LYPAGALRLT LGGSDPGTRP SIVCLRPTRP FAGAQVFAER

MAGNLELLLA EGQGLAGGRC MRWGPRERR

Rat NsG33, N-terminal polypeptide (SEQ ID No 24)
(ASARA)GYSED RCSWRGSGLT QEPGSVGQLT LDCTEGAIEW

LYPAGALRLT LGGSDPGTRP SIVCLRPTRP FAGAQVFAER

MAGNLELLLA EGQGLAGGRC MR
```

Example 2, Bioinformatics Analysis

General Description:

Human NsG33 is a secreted growth factor protein expressed espressed as a 293 amino acid precursor at high levels in the central nervous system and subregions thereof, in the peripheral nervous system, in the retina, and in the human developing Mesenphalon. The mouse (SEQ ID No 8) and rat (SEQ ID No 13) homologues have full lengths of 294 and 291 amino acids and the % identities are 80.3 and 80.2, respectively.

Protein Processing:

Human NsG33 contains an N-terminal signal peptide sequence of 23 amino acids which is cleaved at the sequence motif ARA-GY (SEQ ID NO: 41). This signal peptide cleavage site is predicted by the SignalP method (Nielsen et al., 1997) and the output graph shown in FIG. 1. A signal peptide cleavage site is found at a similar location in the mouse NsG33 (pos. 24) and rat NsG33 (pos. 16 or 21). The most likely cleavage of rat NsG33 is at position 21 as this corresponds to the predicted cleavage position in both human and mouse NsG33. This means that the most likely N-terminal of SEQ ID No. 14, 21, and 24 is GYSEDRCS (SEQ ID NO: 44) and not the ASARAGYSED (SEQ ID NO: 45) shown in the sequence listing.

The signal peptide prediction in mouse NsG33 provides the same cleavage site for the partial NsG33 sequence (SEQ ID No. 8) as for the mouse full length NsG33 sequence (SEQ ID No 26).

Proprotein Processing:

General-type proprotein cleavage is predicted in human NsG33 (SEQ ID No 3) by the ProP method at pos. 127 with a score of 0.831, sequence motif 'WGPRERR-AL' (SEQ ID NO: 421 Similarly, a cleavage site is predicted in mouse NsG33 (SEQ ID No 8) at pos. 128 with a score of 0.831, sequence motif 'WGPRERR-AL' (SEQ ID NO: 42) and in rat NsG33 (SEQ ID No 13) at pos. 125 with a score of 0.831 and the sequence motif 'WGPRERR-AL' (SEQ ID NO: 42).

Protein Function:

NsG33 belongs to the category of proteins acting as growth factors. This notion is supported by predictions by the ProtFun protein function prediction server (Jensen et al., 2002 & 2003), which provides odds scores above 1 for exactly this type of category as shown in FIG. 2. The ProtFun method predicts protein function based on sequence-derived features as opposed to sequence similarity. Features which are important for discriminating between the 'growth factor' classes versus all other classes are: protein sorting potential, protein targeting potential, signal peptide potential, low complexity regions, secondary protein structure, number of negative residues and number of atoms (Jensen et al., 2003).

The sequence identity calculations below have been made with the align0 program, using a BLOSUM50 matrix and gap penalties −12/−2.

TABLE 1 shows the % sequence identity between full length human NsG33 versus mouse and rat sequences.

| Sequence | % id |
| --- | --- |
| human | — |
| mouse | 80.3 |
| rat | 80.2 |

TABLE 2 shows the % sequence identity between human NsG33 versus mouse and rat sequences after removal of N-terminal signal peptide.

| Sequence | % id |
| --- | --- |
| human | — |
| mouse | 81.9 |
| rat | 79.6 |

References:
ProP: Prediction of proprotein convertase cleavage sites. Peter Duckert, Søren Brunak and Nikolaj Blom. Protein Engineering, Design and Selection: 17: 107-112, 2004
SignalP: Identification of prokaryotic and eukaryotic signal peptides and prediction of their cleavage sites. Henrik Nielsen, Jacob Engelbrecht, Søren Brunak and Gunnar von Heijne, Protein Engineering 10, 1-6 (1997).
ProtFun: Ab initio prediction of human orphan protein function from post-translational modifications and localization features. L. Juhl Jensen, R. Gupta, N. Blom, D. Devos, J. Tamames, C. Kesmir, H. Nielsen, H. H. Stærfeldt, K. Rapacki, C. Workman, C. A. F. Andersen, S. Knudsen, A. Krogh, A. Valencia and S. Brunak. J. Mol. Biol., 319:1257-1265, 2002.
Prediction of human protein function according to Gene Ontology categories, L. J. Jensen, R. Gupta, H. H. Stærfeldt, S. Brunak, Bioinformatics, 19, 635-642 (2003).
align0 Optimal alignments in linear space. Myers, E. W. and Miller, W. Comput. Appl. Biosci., 4, 11-17 (1998).

Example 3, Gene-Chip Experiments

The human material came from discarded tissue pieces obtained from electively terminated pregnancies using the regular vacuum aspiration technique. The collection of residual tissue for the study was approved by the Human Ethics Committee of the Huddinge University Hospital, Karolinska Institute (Diary Nr. 259/00) and Lund University (970401), and was in accordance with the guidelines of the Swedish National Board of Health and Welfare (Socialstyrelsen), including an informed consent from the pregnant women seeking abortions. Recovered nervous tissue was micro-dissected within 2 hours of surgery and appropriate tissue fragments were further dissociated for cell isolation.
RNA Isolation:

Human fetal tissue (8 weeks) was obtained in two rounds, both 8-weeks gestation age. Dissected VM and DM regions were used for total RNA isolation with good results and yields.

Total RNA was isolated with the Trizol extraction following the manufacturer's instruction (Invitrogen) from ventral and dorsal mesencephalic regions subdissected from human fetal tissue, 8 weeks gestational age. To concentrate RNA and to remove traces of chromosomal DNA, Rneasy columns combined with with the RNase-Free DNase Set are used following the manufacturer's instructions.

From 5 µg of total RNA, biotinylated cRNA was prepared and fragmented as described in Affymetrix protocols (GeneChip Expression Analysis, Technical Manual 2000) and hybridized (15 µg) to Affymetrix Human U133B GeneChips (containing approximately 22,000 genes) according to manufacturer's instructions. Scanned images were analyzed and converted to expression index values using the GenePublisher analysis software package (Knudsen S, Workman C, Sicheritz-Ponten T, Friis C. (2003) "GenePublisher: Automated analysis of DNA microarray data.", Nucleic Acids Res. 31(13):3471-6.).

Using Affymetrix U133 GeneChips the expression of human NsG33 was analysed (acc. 232269_x_at on U133 B and acc. 219051_x_at on U133 A GeneChip; Affymetrix, Inc., Santa Clara, Calif.). Expression of human NsG33 was observed in human 8-weeks fetal mesencephalon (midbrain) tissue samples indicating that human NsG33 may play a role in early fetal brain development. Expression of a growth factor in the human mesencephalon during embryo development is predictive of a possible therapeutic function in the treatment of Parkinson's Disease.

Example 4, Obtaining a Full Length Coding Sequence

NsG33 was PCR amplified from an IMAGE clone (The I.M.A.G.E. Consortium: "An integrated molecular analysis of genomes and their expression", Lennon, Auffray, Polymeropoulos, and Soares, [1996], Genomics 33: 151-152) obtained from RZPD, Berlin, Germany (RZPD clone ID: IRALp962D105Q2) using the following primers:

```
5' primer:5'-GCGGATCCAGCGGTGGTGAGAGCCCCGAC-3'   (SEQ ID NO: 46)

3' primer:5'-TATACTCGAGGCCCACCCTCCCTCCTACCAG-   (SEQ ID NO: 47)
            3'
```

Three identical PCR reactions were set up with 50 ng/µl of the RZPD clone as DNA template in a 50 µl reaction volume. A proofreading polymerase (pfu-turbo polymerase, Stratagene) was applied for the PCR amplification, with the following amplification profile: pre-denaturation step: 95° C., 1' followed by 35 3-step cycles: denaturation step: 95° C., 30"; annealing step: 57° C., 30"; elongation step: 72° C., 90". Then an elongation step: 72° C., 2' followed by cooling to 4° C.

PCR reactions were pooled and the 988 bp NsG33 PCR fragment was agarose gel-purified and cut with BamHI and XhoI. The now 976 bp BamHI/XhoI-restricted NsG33 PCR fragment was gel-purified. Five µg of a lentiviral transfer vector, pHsCXW, (GenBank accession #: AY468486) was digested with BamHI and XhoI and the vector backbone was gel purified.

The BamHI/XhoI NsG33 PCR fragment was ligated into the BamHI and XhoI sites of the pHsCXW lentiviral transfer vector followed by transformation into XL1-B electrocompetent cells.

Example 5, Real Time PCR on NsG33

The tissues investigated for NsG33 expression were total RNA from Retina, Whole brain, Putamen, Substantia nigra, Ganglion, Fetal liver, Cerebellum, Whole brain, Fetal liver, Heart, Kidney, Lung, Placenta, Prostate, Salivary gland, Skeletal muscle, Spleen, Testis, Thymus, Trachea, Uterus, Colon, Small intestine, Spinal cord, Stomach, Pancreas, Fetal brain.

First strand cDNA was prepared from total RNA using Superscript II Reverse Transcriptase (Life Technologies) and a HT11V primer using standard procedures. For real-time PCR expression analysis product from the Reverse Transcription equivalent to 20 ng of each RNA, was used as template in real-time PCR reactions.

Real-time PCR was performed in an Opticon-2 thermocycler (MJ Research), using LightCycler-FastStart DNA Master SYBR Green I kit (Roche). Studies were carried out in duplicates using primers 5'-CCAGCGACTTCGTAAT-TCAC-3' (5' primer) (SEQ ID NO: 48) and 5'-AGCCCAT-GAAGAGGAAGG-3' (3' primer) (SEQ ID NO: 49). For Real-Time PCR, a standard curve was prepared by serial dilution of a gel-purified PCR product, prepared using the above primers. The standard curve was used to verify that crossing-point values (CT) of all samples were within the exponential range of the PCR reaction and to calculate final expression levels. All RT-PCR amplifications were performed in a total volume of 10 µl containing 3 mM $MgCl_2$, 12% sucrose and 1× reaction buffer included in the Light-Cycler kit. PCR cycling profile consisted of a 10 minutes pre-denaturation step at 98° C. and 35 three-step cycles at 98° C. for 10 seconds, at 62° C. for 20 seconds and at 72° C. for 20 seconds. Following the extension step of each cycle, a plate reading step was added (80° C., 2 seconds) to quantify the newly formed PCR products. The specificity of the amplification reaction was determined by performing a melting curve analysis of the PCR fragments by slowly raising the temperature from 52° C. to 95° C. with continuous data acquisition.

For normalization purposes, all cDNAs were subjected to real-time PCR using primers for $β_2$-microglobulin (B2M, 5'-TGTGCTCGCGCTACTCTCTC-3' (SEQ ID NO: 50) and 5'-CTGAATGCTCCACTTTTTCAATTCT-3' (SEQ ID NO: 51). Standard curves for $β_2$-microglobulin were prepared similar to NsG33. Housekeeping gene real-time PCR was done using the same kit as for the target gene, except that optimal annealing temperatures were used for the housekeeping gene.

Housekeeping expression pattern was determined from the respective standard curves and the relative expression levels were used to normalize expression levels of the target genes in the tissues that were analyzed. Following normalization with the $\beta_2$-microglobulin, relative expression levels of the target gene were calculated using the tissue with the lowest expression as a reference. Results normalised with respect to $\beta_2$-microglobulin should be interpreted with caution, since $\beta_2$-microglobulin may not be expressed at the same level in all tested tissues.

Analysis of Total RNA Samples (Shown in FIGS. 4A and B)
High Expression (C(T) Values<22)
    Putamen, Substantia Nigra, Spinal Cord
Intermediate Expression (22<C(T) Values<24)
    Whole brain, Cerebellum, retina, DRG
Low Expression (24<C(T) Values<26)
    Heart, Kidney, lung, prostate, salivary gland, skeletal muscle, testis, stomach, pancreas, fetal brain
Very Low or no Expression (C(T) Values>26)
    Fetal Liver, Placenta, thymus, trachea, spleen, uterus, colon, small intestine Based on the tissue specific expression, and the fact that NsG33 is predicted to be a secreted growth factor (see example 2), NsG33 is contemplated for use in treating disorders of the nervous system in general (based on the nervous-system specific expression), in particular Parkinson's disease (based on the expression in substantia nigra), Huntington's disease (based on expression in Putamen), cerebellar disorders (based on expression in cerebellum), Spinal Cord injury and ALS (based on expression in the spinal cord), peripheral neuropathies (based on expression in dorsal root ganglion), retinopathies (based on expression in retina). The function for the various indications can be verified in in vitro and in vivo assays as described below.

Example 6: Testing for General Neuroprotective Effect (PC-12 Assay)

Generation of Virus Stock:

NsG33 coding sequence was subcloned into pHsCXW using appropriate restriction sites as described in Example 4. To generate virus stocks, the resulting lentiviral transfer vector was cotransfected into 293T cells with two helper plasmids (pMD.G and pBR8.91) providing the necessary viral genes, gag-pol and env, respectively, in trans. Briefly, $2 \times 10^6$ 293T cells were seeded in each of 20 T75 culture flasks. The next day, each T75 flask was transfected with 15 µg ppBR8.91, 5 µg pMD.G and 20 µg of transfer vector using Lipofectamine+ following the manufacturer's instructions (Invitrogen). Virus-containing medium was harvested 2-3 days after the transfection and filter-sterilized through a 0.45 µm cellulose acetate or polysulphonic filter. The virus was pelleted by double ultracentrifugation at 50,000×g for 90 minutes at 4° C. and then resuspended in DMEM medium. Virus was titrated using a reverse transcriptase (RT) assay (Current Protocols in Molecular Biology, Editors: Ausubel et al., Willey). The number of transducing units (TU)/ml was calculated from the resulting RT activity and frequency of fluorescent cells obtained by transduction of 293T cells with an equivalent GFP lentivirus. The virus stock was stored in aliquots at −80° C. until use.

Transduction of PC12 Cells:

PC12 cells (ATCC accession number: CRL-1721) adapted to DMEM medium were used for testing. PC12 cells are cultured in Dulbecco's modified Eagle's medium (DMEM) with 4.5 g/l glucose and glutamax (Life Technologies #32430-027) with 7.5% donor horse serum (Life Technologies #16050-098) and 7.5% FBS (Life Technologies #10099-141) in the presence of 5% $CO_2$ at 37° C. Medium is changed every 2-3 days and cells are subcultured 1:3-1:6 twice a week by tapping the flask and dispensing into new flasks. The day before transduction, cells were seeded in 6-well plates coated with collagen. Virus was added from the stock solution to 1 ml cell culture medium together with or without 5 µg/ml (final conc.) polybrene. The virus was incubated with the cells for at least 3 hours in a $CO_2$ incubator. GFP retrovirus was added to a parallel culture to estimate transduction efficiency and to serve as control.

Effect on PC12 Differentiation:

Cultures in 6-well plates were followed and scored for the number of neurite bearing cells after 2-5 days.

Effect on PC12 Survival:

Transduced cells from 6-well plates were reseeded in 96-well plates coated with collagen in culture medium. The following day, medium was changed to serum-free DMEM and cell viability was measured after 24-72 hr using the MTS assay following the manufacturer's instructions (Promega). Results from an experiment are shown in FIG. 9. The MTS activity in PC12 cells transduced with a lenti-virus containing full-length NsG33 cDNA was significantly increased as compared to control PC12 cells transduced with a lenti-virus carrying a marker-gene (EGFP). MTS is a measure of the metabolic activity in the total cell population. Thus, the increase in MTS activity in the rLV-NsG33 relative to the control culture may reflect the presence of an increased number of viable cells in the culture and/or increased viability of the surviving cells.

A positive effect in either the neurite outgrowth and/or the survival assay is indicative of a potential therapeutic effect of the NsG33 protein in treating neurodegenerative disorders.

Example 7: Protection of Cerebellar Granule Cells from Glutamate Toxicity

Testing for survival effects is carried out by transducing cultures of cerebellar granule cells that subsequently is exposed to toxic concentrations of glutamate essentially as described (Daniels and Brown, 2001; J. Biol. Chem. 276: 22446-22452).

Cerebellar granule neurons (CGN) are dissected from 7-8 days old mouse pups. Cells are dissociated from freshly dissected cerebella by enzymatic disruption in the presence of trypsin and DNase and then plated in poly-D-lysine-precoated 24-well plates (Nunc) at a density of $1-2 \times 10^6$ cells/cm$^2$ in DMEM medium supplemented with 10% heat-inactivated fetal calf serum. Cells are cultured at 37° C. in a humidified atmosphere and Cytosine arabinoside (10 µM) is added to the culture medium after 24 hr to arrest the growth of non-neuronal cells.

Cultures are transduced with an NsG33 containing lenti-virus prepared as described in Example 6 on DIV1 by the addition of virus stock solution to DMEM medium containing 10% Fetal bovine serum and 4 µg/ml Polybrene. Parallel control cultures are transduced with a Green Fluorescent Protein (GFP) lentivirus. Five hours after the transduction, medium is replaced with medium preconditioned on CGNs.

At DIV5, glutamate (0.1-1 mM) is added the the culture and after two additional days cell survival is assayed using the MTT assay. The extent of MTT reduction to formazane is measured spectrophotometrically at 570 nm. Briefly, culture medium is removed, and cells are washed in sodium saline solution (140 mM NaCl, 5 mM KCl, 1 mM $MgCl_2.6H_2O$, 1 mM $NaH_2PO_4$, 1.5 mM $CaCl_2$, 5.6 mM glucose, 20 mM HEPES, pH 7.4). MTT (final concentration 0.5 mg/ml), prepared just before using and maintained in the dark in sodium saline solution, is then added to the cells. After a 3 h incubation at 37° C., an equal volume of acid-isopropanol (0.04 M HCl in isopropanol) is added and mixed thoroughly at room temperature until all formazan crystals were dissolved. Cell viability is expressed as a percentage of the optical density of control cells. Parallel cultures are left untreated.

This assay can be considered as a general assay for testing of protection against excitotoxic damage as well as an assay predictive for factors with therapeutic potential in the treatment of cerebellar disorders.

Example 8, Protection of Cerebellar Granule Cells from Apoptosis Induced by Potassium Deprivation Testing for survival effects is carried out by transducing cerebellar granule cells deprived of potassium essentially as described (Nomura et al., 2001; Dev. Neurosci. 23: 145-152).

Cerebellar granule neurons (CGN) are dissected from 8-d-old Sprague-Dawley rat pups. Cells are dissociated from freshly dissected cerebella by enzymatic disruption in the presence of trypsin and DNase and then plated in poly-L-lysine-precoated 96-well plates (Nunc) at a density of $3.5 \times 10^5$ cells/cm$^2$ in Eagle's basal medium containing 25 mM KCl and supplemented with 10% heat-inactivated fetal calf serum, 2 mM glutamine. Cells are cultured at 37° C. in a humidified atmosphere and Cytosine arabinoside (10 µM) is added to the culture medium after 24 hr to arrest the growth of non-neuronal cells.

Cultures are transduced with an NsG33 containing lentivirus prepared as described in Example 6 ["Testing in PC12 cells"] on DIV1 by the addition of virus stock solution to DMEM medium containing 10% Fetal bovine serum and 4 µg/ml Polybrene. Parallel control cultures are transduced with a GFP lentivirus. Five hours after the transduction, medium is replaced with medium preconditioned on CGNs.

At DIV2, apoptosis is induced in immature cultures by switching the cells to serum-free medium containing 5 mM KCl, while the untreated cells received conditioned medium containing 25 mM KCl. Survival is measured on DIV3, using the MTS assay.

At DIV8, apoptosis is induced in differentiated (neuronal) cultures by switching the cells to serum-free medium containing 5 mM KCl, while the untreated cells received conditioned medium containing 25 mM KCl. Survival is measured after 24-72 hr, using the MTS assay.

The MTS assay is carried out using the The CellTiter 96® AQ$_{ueous}$ Non-Radioactive Cell Proliferation Assay (Promega) following the manufacturer's instructions.

This assay can be considered as a general assay for neuroprotective effects as well as an assay predictive for factors with therapeutic potential in the treatment of cerebellar disorders.

Example 9, Effect on DRG Cultures

Preparation of Conditioned Media from Transduced ARPE-19 Cells.

To transduce ARPE-19 cells with a lentivirus containing cDNA encoding the NsG33 gene, cells are plated at a density of $1 \times 10^5$ cells/well in a 6-well plate in DMEM/F12 medium supplemented with 10% Fetal Bovine Serum. Next day virus is added from the stock solution to the cell culture medium together with 5 µg/ml (final conc.) polybrene. The virus is incubated with the cells overnight in a CO$_2$ incubator. GFP lentivirus is added to a parallel culture. The next day, cultures are changed to serum-free UltraCULTURE medium (1 ml/well) and conditioned media are harvested after two additional days of incubation.

Isolation and Culture of P1 DRG Cells. DRGs from all spinal levels are removed from P1 (post-natal day 1) Sprague-Dawley. Tissues are enzymatically dissociated in 125-250 U/ml type 1 collagenase (Worthington, Freehold, N.J.) at 37° C. for 30 minutes. Samples are triturated with fire-polished Pasteur pipettes and filtered though 70 µm sterile mesh to produce single cell suspensions. Cells are pre-plated on non-coated tissue-culture-ware dishes for 2 hours to remove non-neuronal cells. Non adherent cells are plated at 15,000 cells/well in 24-well tissue culture dishes that had been coated with poly-d-ornithine (Life Technologies) and laminin (Collaborative Biomedical). Negative controls are cultured in UltraCULTURE™ serum-free media, (BioWhittaker, Walkersville, Md.) containing 2.5 µg/ml sheep-neutralizing anti-NGF pAb (Chemicon, Temecula, Calif.). NGF-treated positive controls lacked the neutralizing anti-NGF pAb. Different dilutions of conditioned medium collected from NsG33-transduced or GFP-transduced ARPE-19 cells are added to the cultures after centrifugation and filtering through a 0.4 µm sterilfilter. Cultures are fed every second day by replacing the media.

Immunocytochemistry.

After seven days in culture, cells are fixed in 4% formaldehyde in PBS for 10 minutes at room temperature. Cells are pre-blocked in 4% goat serum, 0.1% NP40 for 30 minutes at room temperature and then incubated with mouse anti-βIII tubulin (1:100) overnight at 4° C. After rinsing in pre-block solution, the cultures are incubated with a secondary Cy-3 coupled anti-murine antibody for 1 hour at room temperature. Following a final rinse in pre-block solution, cells from a strip through the middle of each well are counted using fluorescence optics. All βIII-tubulin positive cells are scored as neurons and survival is determined by the number of neurons counted per well. All antibodies are diluted in pre-block solution.

Interpretation of Results

Protective effects in this assay indicates therapeutic potential in peripheral neuropathies and neuropathic pain Example 10, Effect on Motoneuron Cultures Testing for survival effects on motoneuron cultures is carried out using NsG33 containing lentivirus essentially as described in Cisterni et al. 200 (J. Neurochem. 74, 1820-1828). Briefly, ventral spinal cords of embryonic day 14.5 (E14.5) Sprague Dawley rat embryos are dissected and dissociated. Motoneurons are purified using a protocol based on the immunoaffinity purification of motoneurons with antibodies against the extracellular domain of the neurotrophin receptor, p75, followed by cell sorting using magnetic microbeads (Arce et al. 1999). Purified motoneurons are seeded on 4-well tissue culture dishes precoated with poly-ornithine/laminin at density of 500 cells per well. Culture medium is Neurobasal culture medium (Life Technologies) supplemented with the B27 supplement (Life Technologies), horse serum (2% v/v), L-glutamine (0.5 mM), and 2-mercaptoethanol (25 µM). L-Glutamate (25 µM) is added to the medium during the first 4 d of culture and subsequently omitted.

Motoneurons cultured for 16 h are transduced with an NsG33 containing lenti-virus prepared as described above by the addition of virus stock solution to the culture medium (corresponding to MOI=4). Parallel control cultures are transduced with a GFP lentivirus. Eight hours after the transduction, medium is replaced with fresh medium (DIV1).

Motoneuron survival is quantified at DIV3 by counting the number of large phase-bright neurons with long axonal processes in a predetermined area of 1.5 cm$^2$ in the center of duplicate dishes.

Interpretation of Results

Protective effects in this assay indicates therapeutic potential in motoneuron diseases including ALS, Spinal Cord injury, SMA (spinal muscular atrophy), DMD (Duchenne muscular dystrophy).

Example 11: Bioassay for Dopaminergic Neurotrophic Activities

Culture Conditions:

Dissociated mesencephalic cell cultures are prepared as previously described (Friedman and Mytilineou 1987 Neurosci. Lett. 79:65-72), with minor modifications. Briefly, rostral mesencephalic tegmentum from brains of Sprague-Dawley rat embryos, at the 13$^{th}$-16th day of gestation, are dissected under the microscope in sterile conditions, collected in Ca$^{2+}$- and Mg$^{2+}$-free Dulbecco's phosphate buffered saline (Gibco, Gaithersburg, Md.) and dissociated mechanically by mild trituration. The cells are plated in 100 µl per well onto 16-mm diameter tissue culture wells (Falcon, Lincoln Park, N.J., 24-well plate) containing 400 µl medium to give a density of 2.5-3.5×10$^5$ cells per well. The culture wells have been previously exposed to 0.1 mg/ml solution of poly L-ornithine in 10 mM sodium borate, pH 8.4, for 3 hours at 37° C., washed 3 times in milli-Q H$_2$O and once in Earle's balanced salt solution (Gibco). The feeding medium (10/10) consists of minimal essential medium (MEM, Gibco) supplemented with glucose (33 mM), sodium bicarbonate (24.5 mM), glutamine (2 mM), HEPES (15 mM), penicillin G (5 U/ml), streptomycin (5 µg/ml), 10% heat-inactivated fetal calf serum (Gibco) and 10% heat inactivated horse serum (Gibco). The cultures are kept at 37° C. in a water-saturated atmosphere containing 6.5% CO$_2$. After 3 hours, when most of the cells have adhered to the bottom of the well, the medium is replaced with 500 µl of fresh medium. At this time, a serial dilution of the sample to be assayed for dopaminergic neurotrophic activity (conditioned medium) is added to each well in duplicate and the plates are incubated in the 37° C. incubator. After a week, the cultures are treated for 24 hours with fluorodeoxyuridine (13 µg/ml) and uridine (33 µg/ml) to prevent excessive glial proliferation and subsequently fed with the above medium without fetal calf serum. The feeding medium is changed weekly.

Alternatively, chemically defined serum-free medium is used in which serum is replaced by a mixture of proteins, hormones and salts. The defined medium (DM) consists of a mixture of MEM and F12 nutrient mixture (both Gibco, 1:1; vol/vol) with glucose (33 mM), glutamine (2 mM) NaHCO$_3$ (24.5 mM), HEPES (15 mM), supplemented with transferrin (100 µg/ml), insulin (25 µg/ml), putrescine (60 µM), progesterone (20 nM), sodium selenite (30 nM), penicillin G (5 U/ml) and streptomycin (5 µg/ml). The osmolarity of the DM is adjusted to 325 by the addition of milli-Q H$_2$O. (110-125 ml H$_2$O/l).

The functional status of the dopaminergic neurons may be assayed in these cultures by measuring dopamine uptake through specific "scavenger" transporters in the dopaminergic neurons and by counting the number of neurons positive for the dopamine synthetic enzyme tyrosine hydroxylase using immunohistochemistry as described in Karlsson et al, 2002, Brain Res. 2002 Nov. 15; 955(1-2):268-80.

Sample Preparation:

Prior to being assayed for dopaminergic neurotrophic activity in the mesencephalic cell cultures, all the samples of conditioned medium are desalted as follows. One hundred µl of the medium 10/10 (as a carrier) is added to a Centricon-10 (Amicon) and allowed to sit for 10 minutes. Aliquots of the sample to be assayed are added to the Centricon, followed by 1 ml of Dulbecco's high glucose Modified Eagle medium, without bicarbonate, but containing 10 mM HEPES, pH 7.2 (solution A), and centrifuged at 5,000×g for 70 minutes. The retentate (about 0.1 ml) is brought back to 1.1 ml with fresh solution A and reconcentrated twice. The sample is filtered through a 0.11 µm Ultrafree-MC sterile Durapore unit (Millipore, Bedford Mass.) prior to being added to the culture well.

$^3$H-Dopamine Uptake:

Uptake of tritiated dopamine ($^3$H-DA) is performed in cultures at day 6 or day 7 as described previously (Friedman and Mytilineou (1987) Neurosci. Lett. 79:65-72) with minor modifications, and all the solutions are maintained at 37° C. Briefly, the culture medium is removed, rinsed twice with 0.25 ml of the uptake buffer which consists of Krebs-Ringer's phosphate buffer, pH 7.4, containing 5.6 mM glucose, 1.3 mM EDTA, 0.1 mM ascorbic acid and 0.5 mM pargyline, an inhibitor of monoamine oxidase. The cultures are incubated with 0.25 ml of 50 nM $^3$H-DA (New England Nuclear, Boston, Mass. sp. act 36-37 Ci/mmol) for 15 minutes at 37° C. $^3$H-DA uptake is stopped by removing the incubation mixture and cells are then washed twice with 0.5 ml of the uptake buffer. In order to release $^3$H-DA from the cells, the cultures are incubated with 0.5 ml of 95% ethanol for 30 min at 37° C., and then added to 10 ml of EcoLite (ICN, Irvine, Calif.) and counted on a scintillation counter. Blank values are obtained by adding to the uptake buffer 0.5 mM GBR-12909 (RBI), a specific inhibitor of the high-affinity uptake pump of the dopamine neurons (Heikkila et al. 1984 Euro J. Pharmacol. 103:241-48).

An increase in the number of TH positive neurons and/or an increase in 3H-dopamine uptake compared to a control treatment is an indication of a possible function of NsG33 in the treatment of Parkinson's disease.

Example 12: Assessment of Neuroprotection of Nigral Dopamine Neurons in Vivo in the Instrastriatal 6-OHDA Lesion Model VSV-G pseudotyped (rLV) vectors are produced as described previously (Zufferey et al., 1997, J. Virol, 73:2886-2892; Rosenblad et al. In vivo protection of nigral dopamine neurons by lentiviral gene transfer of the novel GDNF-family member neublastin/artemin. Mol Cell Neurosci. 2000 February; 15(2):199-214.). Briefly, the transfer plasmids pHR'CMV-W carrying the cDNA for green fluorescent protein (GFP) or NsG33 is co-transfected with the helper plasmids pMD.G and pCMVDR8.91 into 293T cells. Virion containing supernatants are collected on days 2 and 3 after transfection and concentrated at 116 000 g by ultracentrifugation. The titer of rLV-GFP vector stock is 1.1×10$^8$ TU/ml as determined by serial dilution of the concentrated supernatant on 293T cells. The viral particle titre is determined for rLV-NsG33 and rLV-GFP virus stocks using an RNA slot blot technique as described previously (von Schwedler et al. Vif is crucial for human immunodeficiency virus type 1 proviral DNA synthesis in infected cells. Virol. 1993 August; 67(8):4945-55.) and from the ratio between TU and viral particle titre obtained for rLV-GFP, the titre of the rLV-NsG33 vector is estimated to be $1.2\times10^8$ TU/ml All work involving experimental animals are conducted according to the guidelines set by the Ethical Committee for Use of Laboratory Animals at Lund University. Animals are housed in 12:12 hour light/dark cycle with access to rat chow and water. Female Sprague Dawley rats (~220 g by the time of surgery) are used. For stereotaxic surgery animals are anesthetized using halothane and a total of two microliters rLV-GFP (n=8) or rLV-NsG33 of a 1:2 viral stock ($1.0-1.2\times10^5$ TU) are injected into two tracts in the right striatum at the following coordinates: (1) AP=+1.0 mm, ML=−2.6 mm, DV=−5.0 and −4.5 mm, Tb=0.0 and (2) AP=0.0 mm, ML=−3.7 mm, DV=−5.0 and −4.5 mm, Tb=0.0. After two weeks the animals are again anesthetized and placed in the stereotaxic frame. An injection of 6-hydroxydopamine (20 μg [calculated as free base] per 3 μl vehicle [saline with 0.2% ascorbic acid]) is made into the right striatum at the following coordinates: AP=+0.5 mm, ML=−3.4 mm, DV=−5.0 and −4.5 mm, Tb=0.0.

At four weeks post-lesion the animals are deeply anesthetized with pentobarbital (70 mg/kg, Apoteksbolaget, Sweden), and transcardially perfused with 50 ml saline at room temperature, followed by 200 ml ice-cold phosphate-buffered 4% paraformaldehyde (pH 7.2-7.4). The brains are postfixed for 3-6 hours in the same fixative, transferred to 30% sucrose for 24 hours and cut into 6 series of 40 μm thick sections on a freezing microtome.

Immunohistochemistry for detection of tyrosine hydroxylase-immunoreactive, in the substanita nigra is performed as described previously (Rosenblad et al. In vivo protection of nigral dopamine neurons by lentiviral gene transfer of the novel GDNF-family member neublastin/artemin. Mol Cell Neurosci. 2000 February; 15(2):199-214.). The number of TH-IR and VMAT-IR nigral neurons is assessed by counting under microscope all immunoreactive neurons lateral to the medial terminal nucleus of the accessory optic tract in three consecutive sections through the SN, as described previously (Sauer & Oertel, 1994, Neuroscience 59:401-415).

An increase in the number of TH-IR compared to the GFP control is a strong indication of a function in the treatment of Parkinson's disease. An increase in the number of VMAT-IR further strengthens the conclusion.

Example 13: Real-Time PCR Analysis of NsG33 in Developing Murine CNS Tissues Materials & Methods:
Primers:
The following primers were used for real-time PCR:

```
mNsG33:
mNsG33 introns-        5'-GTCTTCGCTGAACGTATGAC-3' (SEQ ID NO: 52)
pan bp284 5':

mNsG33 introns-        5'-CTGATTCTTGCAGCTCTGTG-3' (SEQ ID NO: 53)
pan bp623 3':

GAPDH:
mGAPDH-s904:           5'-AACAGCAACTCCCACTCTTC-3' (SEQ ID NO: 54)

mGAPDH-as1067:         5'-TGGTCCAGGGTTTCTTACTC-3' (SEQ ID NO: 55)
```

Tissue from different brain regions of developing and adult mice was isolated and RNA prepared by Trizol extraction. Subsequent on-column DNAse treatment using RNeasy spin columns was done to remove traces of gDNA and to further clean the RNA. Aliqouts of 2.5 μg RNA was used as template for cDNA synthesis with an RNAseH deficient reverse transcriptase derived from MOMLV (SuperScript) and poly-dT pimer. cDNA from all samples were synthesised at the same time using the same mastermix to avoid variations. The final volume of the cDNA reaction was 120 μl, which was stored in aliquots at −80° C. to avoid repeated thawing and freezing. To analyse the developmental expression of NsG33 in developing Spinal Cord (SC), cDNAs derived from tissues from 10.5, 11.5 and 13.5 days old embryos (E10.5, E11.5 and E13.5, respectively) in addition to tissue from adult mice were prepared. Developmental regulation of NsG33 expression in the cerebellum (Cb) and Cortex (CTX) was analysed using cDNAs derived from P1 and adult tissue.

For real-time PCR expression analysis, approximately 20 ng of each cDNA was used as template. Real-time PCR was performed in an Opticon-2 thermocycler (MJ Research), using LightCycler-FastStart DNA Master SYBR Green I kit (Roche). Studies were carried out in duplicates using the primers described above. For real-time PCR, a standard curve was prepared by serial dilution of a gel-purified PCR product, prepared using the above primers. The standard curve was used to verify that crossing-point values (CT) of all samples were within the exponential range of the PCR reaction and to calculate final expression levels. All real-time PCR amplifications were performed in a total volume of 10 μl containing 3 mM $MgCl_2$, 12% sucrose and 1× reaction buffer included in the LightCycler kit. PCR cycling profile consisted of a 10 minutes pre-denaturation step at 98° C. and 35 three-step cycles at 98° C. for 10 seconds, at 62° C. (mGAPDH) or 60° C. (mNsG33) for 20 seconds and at 72° C. for 20 seconds. Following the extension step of each cycle, a plate reading step was added (80° C., 2 seconds) to quantify the newly formed PCR products. The specificity of the amplification reaction was determined by performing a melting curve analysis of the PCR fragments by slowly raising the temperature from 52° C. to 95° C. with continuous data acquisition.

For normalization purposes, all cDNAs were subjected to real-time PCR using primers for the housekeeping gene GAPDH. Real-time PCR analysis of GAPDH was done as for the target genes. Housekeeping expression pattern was determined from the respective standard curves and the relative expression levels were used to normalize expression levels of the target genes in the tissues that were analysed. Following normalization with GAPDH, relative expression levels of the target genes were calculated using the tissue with the lowest expression as a reference.

Results:

The relative GAPDH expression varied no more than between 1.0 and 1.3 among the different ages and tissues showing that GAPDH could be used for normalisation.

The real-time PCR results for mouse NsG33 are shown in FIGS. 10A and 10B. CT values ranged from 17 to 22. From FIG. 10A, it is apparent that NsG33 expression is regulated during development of the Spinal Cord peaking around E11.5. From FIG. 10B, it is apparent that NsG33 is regulated during the postnatal development in Cerebellum but not in Cortex.

NsG33 is a secreted molecule that is highly conserved across species with features of a growth factor or hormone with an expression pattern that in combination with its other features strongly predicts a therapeutic use for the treatment of neurological disorders.

The temporal expression pattern in Spinal Cord indicates a role in proliferation, differentiation and/or survival of the neural progenitors in this region of the CNS. This is consistent therapeutic relevance for treatment of neurodegenerative diseases and injuries in the Spinal Cord including Spinal Cord Injury, ALS, and spinal muscular atrophy. Furthermore this expression profile indicates a potential as in vitro reagent for expansion and/or differentiation of neural progenitors derived from the Spinal Cord.

The up-regulation of NsG33 expression in the adult Cerebellum indicates a role for this factor in maintenance and/or survival of one or more cerebellar cell types. This is consistent with therapeutic relevance for cerebellar disorders including including but not limited to sensory ataxia, multiple sclerosis, neurodegenerative spinocerebellar disorders, hereditary ataxia, cerebellar atrophies (such as Olivo-pontocerebellar Atrophy (OPCA), Shy-Drager Syndrome (multiple systems atrophy)), and alcoholism.

Example 14: The Effect of hNsG33 on Differentiation of a Human Neural Progenitor Cells Generation of Conditioned Media Cells secreting hNsG33 were generated by transducing ARPE-19 cells with a lenti-viral construct containing hNsG33 cDNA, LV-sC.NsG33.W. Briefly, cells were seeded in 6-well plates at 50-70% confluency ($1\times10^5$ cells/well) in DMEM/F12 (1:1) supplemented with 10% FCS. After an overnight incubation, polybrene (5 µg/ml) and virus was added to the cells. The following day, cells were passaged to T25 flasks. Aliquots of transduced cells were frozen after an additional passage.

To collect conditioned medium from the transduced and parental (control) ARPE-19 cultures, cells were seeded in T25 flasks. After 4 days of incubation, cultures were changed to serum-free HSC medium. After additional 24 h the conditioned media from control and NsG33 ARPE-19 cells were collected, and processed by centrifugation at 3000×g for 5 min before addition to hNS1 cultures.

Testing in hNS1 Cells hNS1 (formerly called HNSC.100) is an embryonic forebrain-derived, multipotent, clonal cell line of neural stem cells that has previously been described (Villa et al., Exp Neurol, 2000, 161(1):67-84). Villa et al 2004, Exp Cell Res. April 1; 294(2):559-70). Cells were obtained from Alberto Martinez Serrano, Department of Molecular Biology, Center of Molecular Biology Severo Ochoa, Autonomous University of Madrid-CSIC, Campus Cantoblanco, Madrid, 28049, Spain. hNS1 cultures were expanded in poly-Lysine coated TC flasks at 5% $CO_2$ and 37° C. in serum-free HSC medium supplemented with 20 ng/ml of EGF and bFGF. HSC medium consisted of DMEM/F12 (1:1) supplemented with N2 and 1% BSA. For differentiation experiments, hNS1 cells were seeded onto coverslips precoated with 50 µg/ml poly-lysine in mitogen-free, 0.5% FBS containing HSC medium at a density of $10^5$ cells/cm². One day after seeding, the differentiation medium was changed to 100% conditioned medium collected from either parental ARPE-19 cells (Mc C) or ARPE-19 cells transduced with lenti-viral hNsG33 (Mc 33). A control culture received unconditioned HSC medium. Two-third of the medium was replaced the next day and then every second or third day. Four days after plating, cultures were fixed for 10 min in 4% paraformaldehyde and stained by immunohistochemistry.

Immunohistochemistry

After blocking in 10% normal horse serum, Cultures were incubated with primary antibodies to GFAP (pAb rabbit anti-cow, 1:1000, DAKO) and β-tubulin (mAb clone SCL: 3D10, 1:1000, Sigma). After being rinsed, cultures were incubated with secondary antibodies biotinylated horse-anti-mouse (Vector Laboratories, 1:200) followed by detection using Strep-Cy3 (Jackson InmunoResearch, 1/200) and Alexa Fluor 488-labelled goat anti-rabbit (Molecular Probes, 1:200), respectively. Cell nuclei were counterstained with Hoechst 33258 at 0.2 µg/ml. (Villa et al., 2004). For the analysis the total number of cells (nuclei) in addition to the GFAP and β-tubulin positive cells were counted by confocal microscopy using a 63× objective.

Results

As shown in FIG. 11A, the addition of conditioned medium from and ARPE-19 cells transduced with a lenti-viral construct containing hNsG33 cDNA (Cm 33) increased the percentage of β-III-tubulin positive neurons 73% relative to control cultures (hNS1) whereas conditioned medium from control ARPE-19 cells (Cm C) had no effect. The increase observed with Cm 33 medium relative to both hNS1 medium and Cm C medium was statistically significant in a t-test ($P<0.05$).

Conditioned media from NsG33 transduced ARPE-19 cells also appeared to increase the number of GFAP positive glial cells compared to hNS1 medium significantly (17 vs. 11%, respectively). However, a similar increase was observed with control conditioned (Cm C) medium (16 vs. 11%, respectively) although this was not statistically significant. The addition of conditioned media from control ARPE-19 cells (Cm C) and ARPE-19 cells transduced with a lenti-viral construct containing hNsG33 cDNA did not alter the total number of cells significantly as shown in FIG. 11B.

The increased neuronal number may result from increased differentiation of neuronal progenitor cells present in the cultures and/or a survival effect on the differentiated neurons. These data are consistent with a neuroprotective and regenerative potential of NsG33.

Example 15: Testing the Effect of NsG33 on Striatal Cultures

Preparation of Conditioned Media for Testing

Conditioned media were prepared from ARPE-19 and HEK293T cells transiently transfected with an expression construct containing hNsG33 cDNA (pHsC.NsG33.W) in addition to MOCK transfected ARPE-19 and HE293T cells.

ARPE-19 cells were seeded in 6-well plates ($1\times10^5$ cells/well) in DMEM:F12 (1:1) supplemented with 10% FCS. After overnight incubation, cells were transfected with Fugene using 3 µg DNA/well according to the manufacturers instructions (Roche).

HE293T cells were seeded in 6-well plates ($3\times10^5$ cells/well) in DMEM supplemented with 10% FCS. After overnight incubation, cells were transfected with Lipofectamine+ using 2 µg DNA/well according to the manufacturers instructions (Invitrogen).

The day after transfection, the medium was changed to serum-free DMEM:F12 medium. After 24 h of conditioning, media were collected from the transfected cells and processed by centrifugation at 3000×g for 5 min. The cleared conditioned media were diluted with DMEM:F12 (6:16) before addition to striatal cultures. Expression of NsG33 mRNA was analysed by quantitative RT-PCR using specific primers for hNsG33 cDNA.

Quantitative RT-PCR

Total RNA was prepared from the transfected cultures by Trizol extraction followed by on-column DNAse treatment using RNeasy spin columns to remove traces of gDNA and to further clean the RNA. cDNA was synthesized using Reverse Transcriptase and each cDNA corresponding to approximately 20 ng total RNA was used as template for real-time PCR expression analysis with hNsG33 primers as described in Example 5.

For normalization purposes, all cDNAs were subjected to real-time PCR using primers 4842 and 4843 for the housekeeping gene GAPDH [4842: 5'-GGAAGGTGAAGGTCG-GAGTCAA-3' (SEQ ID NO: 56) and 4843: 5% GATCTCGCTCCTGGAAGATGGT-3] (SEQ ID NO: 57). Following normalization with GAPDH, relative expression levels of the target genes were calculated using cDNA samples with the lowest hNsG33 expression as a reference.

Generation and Testing of Striatal Cultures

Cell cultures of embryonic rat striatum were prepared essentially as previously described (Nakao et al., 1996 Exp. Neurol. 138, 144-157). Briefly, the lateral and medial ganglionic eminences were selectively dissected out from E14.5 rat embryos (Sprague-Dawley, B&K Universal, Sweden). Tissue pieces were incubated with trypsin/DNAse at 37°, rinsed and dissociated mechanically. Dissociated cells were plated onto four well chamber slides (100,000 cells/cm²) precoated with 50 µg/ml poly-l-lysine and 10 ug/µl laminin in DMEM medium supplemented with 15 mM HEPES, 1 mM sodium pyruvate and 10% FCS. After 2 days in vitro, medium was changed to serum-free DMEM:F12 (1:1) supplemented with 1.5 mM HEPES, 1 mM Sodium pyruvate and B27 (1:50), unconditioned or conditioned by NsG33- or MOCK transfected HEK293T cells or ARPE-19 generated as described above. After 4 days of incubation in serum-free media, cultures were processed for immunohistochemistry.

Immunohistochemistry

Briefly, cell cultures were fixed for 20 min in 4% paraformaldehyde. After preincubation in 5% blocking serum, cultures were incubated overnight at room temperature with anti-β-III-tubulin antibody (Sigma, 1:333). After being rinsed, cultures were incubated with secondary antibody FITC-conjugated donkey-anti-mouse (1:200, Jackson Lab) for two hours, RT. Cell nuclei were counterstained with DAPI. For the analysis, the total number of cells (nuclei) and number of β-III-tubulin positive cells were counted in 16 random fields per condition (average total cell number=260) using the 40× magnification.

Results

The expression of hNsG33 mRNA in transiently transfected cultures was confirmed using quantitative Reverse Transcription PCR. In HEK293T cultures transiently transfected with the pHsC.NsG33.W, normalized levels of hNsG33 mRNA 40-6000 times higher than in untransfected cultures were determined by qRT-PCR. Also in transfected ARPE-19 cultures a higher level of hNsG33 mRNA was detected (30-35 times the control level in MOCK transfected cultures).

As shown in FIG. 12, the addition of conditioned media from ARPE-19 cells transfected with an expression construct containing hNsG33 cDNA increased the percentage of β-III-tubulin positive neurons with 49% in the striatal cultures relative to cultures receiving conditioned media from MOCK transfected ARPE-19 cells (48% vs. 32%). The increase was statistically significant in a t-test (P<0.05).

Similarly, a 34% statistically significant increase in the percentage of neurons was observed in cultures receiving conditioned medium from HEK293T cells transfected with the hNsG33 construct relative to MOCK transfected HEK293T cultures (50% vs. 37%).

No effect on of addition of conditioned media from any of the MOCK transfected cultures was observed relative to control cultures receiving unconditioned medium (UCM). The increase in neuronal percentages was not due to an increase in total number of cells determined from counting nuclei stained with DAPI but an increased number of neurons in the cultures receiving media containing hNsG33. The increased neuronal number may result from increased differentiation of neuronal progenitor cells present in the cultures and/or a survival effect on the differentiated striatal neurons. These data are consistent with general neuroprotective and regenerative effect of NsG33 and specifically a therapeutic potential of NsG33 in Huntington's disease.

The invention claimed is:

1. A method of treating Huntington's disease in a human subject in need thereof comprising providing trophic support to striatal neurons by administering to the subject a therapeutically effective amount of a neurotrophic polypeptide comprising an amino acid sequence:

having at least 90% identity to the amino acid sequence of SEQ ID NO: 4;

having cysteine residues at positions 7, 28, 59, 95, 148, 151, 161, 219, 243, and 265 relative to the amino acid sequence of SEQ ID NO:4; and further comprising all amino acid residues marked in FIG. 3a as fully conserved (*).

2. The method of claim 1, wherein any substitution of an amino acid residue marked in FIG. 3a as strongly conserved (:) is made within the following conserved groups: serine, threonine, and alanine; asparagine, glutamic acid, glutamine, and lysine; asparagine, histidine, glutamine, and lysine; asparagine, glutamic acid, aspartic acid, and glutamine; glutamine, histidine, arginine, and lysine; methionine, isoleucine, leucine, and valine; methionine, isoleucine, leucine, and phenylalanine; histidine and tyrosine; and phenylalanine, tyrosine, and tryptophan.

3. The method of claim 1, wherein the neurotrophic polypeptide comprises the amino acid sequence of SEQ ID NO:4.

4. A method of treating Huntington's disease in a human subject in need thereof comprising providing trophic support to striatal neurons by administering to the striatum of the subject a therapeutically effective amount of a neurotrophic polypeptide comprising an amino acid sequence having at least 90% identity to the amino acid sequence of SEQ ID NO: 4 and which further comprises the amino acid sequence of SEQ ID NO: 60.

5. The method of claim 4, wherein the neurotrophic polypeptide comprises the amino acid sequence of SEQ ID NO:4.

6. A method of providing trophic support to striatal neurons in a human subject in need thereof, comprising administering to the striatum of the subject a therapeutically effective amount of a neurotrophic polypeptide comprising an amino acid sequence having at least 90% identity to the amino acid sequence of SEQ ID NO: 4 and which further comprises the amino acid sequence of SEQ ID NO: 60.

7. The method of claim 6, wherein the neurotrophic polypeptide comprises the amino acid sequence of SEQ ID NO:4.

* * * * *